United States Patent
Kozlov et al.

(10) Patent No.: US 9,958,454 B2
(45) Date of Patent: May 1, 2018

(54) PEPTIDE CONSTRUCTS AND ASSAY SYSTEMS

(71) Applicant: Prognosys Biosciences, Inc., San Diego, CA (US)

(72) Inventors: Igor A. Kozlov, San Diego, CA (US); Mark S. Chee, Encinitas, CA (US); Petr Capek, San Diego, CA (US); David A. Routenberg, San Diego, CA (US)

(73) Assignee: Prognosys Biosciences, Inc., San Diego, CA (US)

( * ) Notice: Subject to any disclaimer, the term of this patent is extended or adjusted under 35 U.S.C. 154(b) by 161 days.

(21) Appl. No.: 14/068,921

(22) Filed: Oct. 31, 2013

(65) Prior Publication Data

US 2014/0051589 A1     Feb. 20, 2014

Related U.S. Application Data

(63) Continuation of application No. 13/442,637, filed on Apr. 9, 2012.

(60) Provisional application No. 61/473,709, filed on Apr. 8, 2011.

(51) Int. Cl.
    *G01N 33/543*      (2006.01)
    *G01N 33/68*      (2006.01)
    *C12N 15/10*      (2006.01)

(52) U.S. Cl.
    CPC ..... *G01N 33/6803* (2013.01); *C12N 15/1062* (2013.01); *C12N 15/1075* (2013.01)

(58) Field of Classification Search
None
See application file for complete search history.

(56) References Cited

U.S. PATENT DOCUMENTS

| | | |
|---|---|---|
| 5,002,882 A | 3/1991 | Lunnen et al. |
| 5,512,439 A | 4/1996 | Hornes et al. |
| 6,210,894 B1 | 4/2001 | Brennan |
| 6,258,558 B1 | 7/2001 | Szostak et al. |
| 6,261,804 B1 | 7/2001 | Szostak et al. |
| 6,281,804 B1 | 8/2001 | Haller et al. |
| 6,344,316 B1 | 2/2002 | Lockhart |
| 6,416,950 B1 | 7/2002 | Lohse et al. |

(Continued)

FOREIGN PATENT DOCUMENTS

| | | |
|---|---|---|
| EP | 1712623 | 10/2006 |
| JP | 2011-182702 | 6/2011 |

(Continued)

OTHER PUBLICATIONS

Shults et al (ChemBioChem 2007, vol. 8, pp. 933-942).*

(Continued)

*Primary Examiner* — Celine Qian
(74) *Attorney, Agent, or Firm* — Morrison & Foerster LLP

(57) ABSTRACT

The present invention provides methods for constructing peptide construct sets and methods of use of these peptide construct sets in assay systems for peptide analysis, and in particular for use in high throughput peptide analysis. The methods allow for analysis of large sets of peptide constructs in a cost-effective manner, employing molecular biological techniques that are both robust and easily parallelized. Thus, the methods allow for the construction of peptide construct sets encompassing, e.g., the human proteome.

24 Claims, 16 Drawing Sheets

(56) References Cited

U.S. PATENT DOCUMENTS

| | | |
|---|---|---|
| 6,485,982 B1 | 11/2002 | Charlton |
| 6,518,018 B1 | 2/2003 | Szostak et al. |
| 6,579,695 B1 | 6/2003 | Lambalot et al. |
| 6,632,641 B1 | 10/2003 | Brennan et al. |
| 6,800,453 B2 | 10/2004 | Labaer et al. |
| 6,878,515 B1 | 4/2005 | Landegren |
| 7,118,883 B2 | 10/2006 | Inoue et al. |
| 7,192,735 B2 | 3/2007 | Lambalot et al. |
| 7,229,769 B2 * | 6/2007 | Kozlov et al. ............... 435/6.16 |
| 7,270,950 B2 | 9/2007 | Szostak et al. |
| 7,378,242 B2 | 5/2008 | Hurt |
| 7,393,665 B2 | 7/2008 | Brenner |
| 7,407,757 B2 | 8/2008 | Brenner |
| 7,537,897 B2 | 5/2009 | Brenner et al. |
| 7,544,473 B2 | 6/2009 | Brenner |
| 7,579,153 B2 | 8/2009 | Brenner et al. |
| 7,635,566 B2 | 12/2009 | Brenner |
| 7,666,612 B2 | 2/2010 | Johnsson et al. |
| 7,674,752 B2 | 3/2010 | He et al. |
| 7,776,547 B2 | 8/2010 | Roth |
| 7,858,321 B2 | 12/2010 | Glezer et al. |
| 8,207,093 B2 | 6/2012 | Szostak et al. |
| 8,337,851 B2 | 12/2012 | Aukerman et al. |
| 8,343,500 B2 | 1/2013 | Wraith et al. |
| 9,085,798 B2 | 7/2015 | Chee |
| 2003/0087232 A1 | 5/2003 | Christians et al. |
| 2003/0096323 A1 | 5/2003 | James |
| 2003/0113713 A1 | 6/2003 | Glezer et al. |
| 2003/0138879 A1 | 7/2003 | Lambalot et al. |
| 2003/0162216 A1 | 8/2003 | Gold et al. |
| 2003/0224419 A1 | 12/2003 | Corcoran et al. |
| 2003/0232382 A1 | 12/2003 | Brennan et al. |
| 2003/0235852 A1 | 12/2003 | Roberts et al. |
| 2004/0112442 A1 | 6/2004 | Maerkl |
| 2005/0003431 A1 | 1/2005 | Wucherpfennig |
| 2005/0026188 A1 | 2/2005 | Van Kessel et al. |
| 2005/0048580 A1 | 3/2005 | Labaer et al. |
| 2005/0164292 A1 | 7/2005 | Faroqui et al. |
| 2005/0255548 A1 | 11/2005 | Lipovsek et al. |
| 2005/0260653 A1 | 11/2005 | Labaer et al. |
| 2006/0003394 A1 | 1/2006 | Song et al. |
| 2006/0046313 A1 | 3/2006 | Roth et al. |
| 2006/0134669 A1 | 6/2006 | Casasanta |
| 2006/0199207 A1 | 9/2006 | Matysiak |
| 2006/0216721 A1 | 9/2006 | Kozlov et al. |
| 2006/0216775 A1 | 9/2006 | Burkhart et al. |
| 2006/0228758 A1 | 10/2006 | Muchhal |
| 2006/0275799 A1 | 12/2006 | Banerjee et al. |
| 2007/0014810 A1 | 1/2007 | Baker et al. |
| 2007/0020625 A1 | 1/2007 | Duchaud et al. |
| 2007/0020669 A1 | 1/2007 | Ericsson |
| 2007/0026430 A1 | 2/2007 | Andersen et al. |
| 2007/0172893 A1 | 7/2007 | Clemeston |
| 2008/0071071 A1 | 3/2008 | LaBaer et al. |
| 2008/0108804 A1 | 5/2008 | Hayashizaki et al. |
| 2008/0220981 A1 | 9/2008 | McGregor |
| 2008/0293591 A1 | 11/2008 | Taussig et al. |
| 2008/0312103 A1 | 12/2008 | Nemoto et al. |
| 2009/0280487 A1 | 11/2009 | Hung et al. |
| 2009/0291854 A1 | 11/2009 | Wiesinger-Mayr et al. |
| 2010/0069263 A1 | 3/2010 | Shendure et al. |
| 2010/0099103 A1 | 4/2010 | Hsieh et al. |
| 2010/0113302 A1 | 6/2010 | Williams |
| 2010/0159446 A1 | 6/2010 | Haff |
| 2010/0173384 A1 | 7/2010 | Johnsson et al. |
| 2010/0184614 A1 | 7/2010 | Ye et al. |
| 2011/0245101 A1 | 10/2011 | Chee et al. |
| 2011/0245111 A1 | 10/2011 | Chee |
| 2012/0065081 A1 | 3/2012 | Chee |
| 2012/0129248 A1 | 5/2012 | Chee et al. |
| 2012/0195810 A1 | 8/2012 | Cohen et al. |
| 2012/0270748 A1 | 10/2012 | Chee et al. |
| 2013/0096033 A1 | 4/2013 | Routenberg |
| 2013/0109595 A1 | 5/2013 | Routenberg |
| 2013/0296174 A1 | 11/2013 | Peumans |
| 2015/0087027 A1 | 3/2015 | Makarov |
| 2016/0024576 A1 | 1/2016 | Chee |
| 2016/0333403 A1 | 11/2016 | Chee |
| 2017/0058339 A1 | 3/2017 | Chee |
| 2017/0058340 A1 | 3/2017 | Chee |
| 2017/0058345 A1 | 3/2017 | Chee |
| 2017/0088881 A1 | 3/2017 | Chee |

FOREIGN PATENT DOCUMENTS

| | | |
|---|---|---|
| WO | WO-2003/010176 | 2/2003 |
| WO | WO 2004/028955 | 4/2004 |
| WO | WO-2005/026387 | 3/2005 |
| WO | WO 2006/117541 | 11/2006 |
| WO | WO-2007/041689 | 4/2007 |
| WO | WO-2007/060599 | 5/2007 |
| WO | WO-2007/073171 | 6/2007 |
| WO | WO-2007/076726 | 7/2007 |
| WO | WO-2007/145612 | 12/2007 |
| WO | WO-2009/032167 | 3/2009 |
| WO | WO-2010/019826 | 2/2010 |
| WO | WO 2010/027870 | 3/2010 |
| WO | WO-2010/127186 | 11/2010 |
| WO | WO-2011/014879 | 2/2011 |
| WO | WO-2011/071943 | 6/2011 |
| WO | WO-2011/127006 | 10/2011 |
| WO | WO-2011/127099 | 10/2011 |
| WO | WO 2012/022975 | 2/2012 |
| WO | WO 2012/071428 | 5/2012 |
| WO | WO-2012/139110 | 10/2012 |
| WO | WO-2014/210223 | 12/2014 |
| WO | WO-2014/210225 | 12/2014 |

OTHER PUBLICATIONS

Condina et al (Proteomics 2009, vol. 9, pp. 3047-3057).*
O'Shannessy et al (Analytical Biochemistry, vol. 229, pp. 119-124).*
Response to Office Action for U.S. Appl. No. 13/266,568, dated Jun. 26, 2014, 11 pages.
Response to Office Action for U.S. Appl. No. 13/080,616, dated Aug. 11, 2014, 22 pages.
Examination Report for European Patent Application No. EP 10836568.5, dated Mar. 12, 2014, 3 pages.
Response to Examination Report for European Patent Application No. EP 10836568.5, dated Jul. 10, 2014, 1 page.
Second Examination Report for Chinese Patent Application No. CN 201180017696.3, dated Jul. 3, 2014, 11 pages.
Response to Search Report for European Patent Application No. EP 11766613.1, dated Jul. 11, 2014, 1 page.
Examination Report issued in European Patent Application No. 10836568.5, dated Mar. 12, 2014, 3 pages.
Mizusawa and Ward, "A bacteriophage lambda vector for cloning with BamHI and Sau3A," Gene (1982) 20(3):317-322.
Notice of Acceptance issued in Australian Patent Application No. Au 2011237729, dated Mar. 20, 2014, 6 pages.
Office Action for U.S. Appl. No. 13/266,568, dated Mar. 26, 2013, 9 pages.
Office Action for U.S. Appl. No. 13/080,616, dated Apr. 9, 2014, 8 pages.
Office Action for CA 2794522, dated May 22, 2014, 10 pages.
Patent Examination Report for AU 2010278710, dated Feb. 11, 2014, 4 pages.
Shoemaker et al., "Quantitative phenotypic analysis of yeast deletion mutants using a highly parallel molecular bar-coding strategy," (1996) Nat Genet 14(4):450-456.
Worthington et al., "Cloning of random oligonucleotides to create single-insert plasmid libraries," Anal Biochem (2001) 294(2):169-175.
Final Office Action for U.S. Appl. No. 13/080,616, dated Oct. 21, 2014.
Response to final Office Action for U.S. Appl. No. 13/080,616, filed Feb. 23, 2015.

(56) References Cited

OTHER PUBLICATIONS

Advisory Action for U.S. Appl. No. 13/080,616, dated Mar. 17, 2015.
Response to Office Action for CA 2794522, dated Sep. 17, 2014.
Response to Second Examination Report for CN 201180017696.3, filed Sep. 17, 2014.
Third Examination Report for CN 201180017696.3, dated Jan. 27, 2015.
Response to Third Examination Report for CN 201180017696.3, filed Apr. 13, 2015.
European Examination Report for EP 11766613.1, dated Aug. 22, 2014.
Response to European Examination Report for EP 11766613.1, filed Jan. 8, 2015.
Office Action for U.S. Appl. No. 13/442,637, dated Jan. 22, 2015.
Extended European Search Report for EP 12767937.1-1403, dated Nov. 18, 2014.
International Search Report and Written Opinion of PCT/US14/29691, dated Aug. 19, 2014.
International Search Report and Written Opinion of PCT/US14/44191, dated Nov. 7, 2014.
International Search Report and Written Opinion of PCT/US14/44196, dated Nov. 7, 2014.
International Search Report and Written Opinion of PCT/US14/64588, dated Mar. 11, 2015.
Non-final Office Action in U.S. Appl. No. 14/723,332, dated Feb. 23, 2016.
Final Office Action in U.S. Appl. No. 14/723,332, dated Nov. 29, 2016.
Non-final Office Action in U.S. Appl. No. 14/723,332, dated Mar. 28, 2017.
Non-final Office Action in U.S. Appl. No. 15/224,253, dated Dec. 9, 2016.
Non-final Office Action in U.S. Appl. No. 15/224,253, dated May 18, 2017.
Final Office Action in U.S. Appl. No. 15/224,253, dated Jul. 3, 2017.
Patent Examination Report No. 1 for AU 2014203638, dated Oct. 1, 2015.
Office Action for U.S. Appl. No. 13/442,637, dated Oct. 8, 2015.
Extended European Search Report for EP 16183356.1, dated Apr. 24, 2017.
Restriction Requirement in U.S. Appl. No. 14/776,537, dated Jan. 6, 2017.
Non-final Office Action in U.S. Appl. No. 14/776,537, dated May 2, 2017.
First Examination Report in CN 201480028069.3, dated Aug. 26, 2016 (Including English translation).
Second Examination Report in CN 201480028069.3, dated Jul. 10, 2017 (Including English translation).
Extended European Search Report for EP 14765026.1, dated Sep. 26, 2016.
Non-final Office Action in U.S. Appl. No. 14/900,602, dated Jan. 9, 2017.
Extended European Search Report for EP 14816674.7, dated Feb. 3, 2017.
Non-final Office Action in U.S. Appl. No. 14/900,604, dated Feb. 7, 2017.
Extended European Search Report for EP 14818012.8, dated Feb. 3, 2017.
Cerutti et al., "Generation of sequence-specific, high affinity anti-DNA antibodies," Journal of Biological Chemistry (2001) 276(16):12769-12773.
Chen et al., "DNA hybridization detection in a microfluidic Channel using two fluorescently labelled nucleic acid probes", Biosensors and Bioelectronics (2008) 23:1878-1882.
Cujec et al. "Selection of v-abl tyrosine kinase substate sequences from randomnized peptide and cellular proteomic libraries using mRNA display," Chemistry and Biology (2002) 9:253-264.

Eldridge et al. "An in vitro selection strategy for conferring protease resistance to ligand binding peptides," Protein Eng Des Sel (2009) 22(11):691-698.
Osada et al., "Epitope mapping using ribosome display in a resconstituted cell-free protein synthesis system," Journal of Biochemistry, 2009, 145(5):693-700.
Rountenberg et al., "Microfluidic probe: a new tool for integrating microfluidic environments and electronic wafer-probing," Lab Chip, Oct. 29, 2009, 10: 123-127.
Sergeeva et al., "Display technologies: Application for the discovery of drug and gene delivery agents," Advanced Drug Delivery Reviews (2006) 58(15):1622-1654.
Tian et al., "Antigen peptide-based immunosensors for rapid detection of antibodies and antigens," Anal Chem (2009) 81:5218-5225.
Valencia et al., "mRNA-display-based selections for proteins with desired functions: A protease-substrate case study," Biotechnology Progress, 2008, 24(3): 561-569.
Weichhart et al., "Functional selection of vaccine candidate peptides from *Staphylococcus aureus* whole-genome expression libraries in vitro," Infection and Immunity, 2003, 71(8):4333-4641.
Yonezawa et al., "DNA display for in vitro selection of diverse peptide libraries", Nucleic Acids Research (2003) 31(19):e118.
Office Action for U.S. Appl. No. 13/266,568, dated Mar. 29, 2013.
Response to Office Action for U.S. Appl. No. 13/266,568, filed Aug. 29, 2013.
Final Office Action for U.S. Appl. No. 13/266,568, dated Dec. 5, 2013.
Office Action for U.S. Appl. No. 13/388,229, dated Dec. 24, 2012.
International Search Report and Written Opinion for PCT/US2010/033064, dated Jul. 30, 2010.
International Preliminary Report on Patentability Chapter I for PCT/US2010/033064, dated Nov. 1, 2011.
International Search Report and Written Opinion for PCT/US2010/044134, dated Mar. 18, 2011.
International Preliminary Report on Patentability Chapter I for PCT/US2010/044134, dated Jan. 31, 2012.
Communication Pursuant to Art. 94(3) EPC for EP 10747097.3, dated Jul. 26, 2013.
Patent Examination Report No. 1 for AU 2010278710, dated Jul. 11, 2013.
Restriction Requirement for U.S. Appl. No. 13/514,045, dated Nov. 23, 2012.
Response to Restriction Requirement for U.S. Appl. No. 13/514,045, filed Dec. 19, 2012.
Office Action for U.S. Appl. No. 13/514,045, dated Feb. 21, 2013.
Response to Office Action for U.S. Appl. No. 13/514,045, filed Jun. 17, 2013.
Response to Office Action for U.S. Appl. No. 13/514,045, filed Jun. 27, 2013.
Final Office Action for U.S. Appl. No. 13/514,045, dated Oct. 18, 2013.
International Search Report and Written Opinion for PCT/US2010/059327, dated Mar. 29, 2011.
International Preliminary Report on Patentability Chapter I for PCT/US2010/059327, dated Jun. 12, 2012.
Patent Examination Report No. 1 for AU 2010328226, dated May 9, 2013.
First Office Action for CN 201080055351.2, dated Jul. 23, 2013.
Supplemental European Search Report for EP 10836568.5, dated Feb. 13, 2013.
Response to Supplemental European Search Report for EP 10836568.5, dated Sep. 10, 2013.
First Examination Report for EP 10836568.5, dated Oct. 1, 2013.
Response to First Examination Report for EP 10836568.5-1403, dated Feb. 17, 2014.
Restriction Requirement for U.S. Appl. No. 13/080,616, dated Dec. 17, 2013.
Response to Restriction Requirement for U.S. Appl. No. 13/080,616, filed Jan. 16, 2014.
International Search Report and Written Opinion for PCT/US2011/031308, dated Jun. 7, 2011.
International Preliminary Report on Patentability Chapter I for PCT/US2011/031308, dated Oct. 9, 2012.

(56) References Cited

OTHER PUBLICATIONS

Patent Examination Report No. 1 for AU 2011237729, dated Jul. 9, 2013.
Voluntary Amendment and Observation for CN 201180017696.3, filed Jul. 25, 2013.
First Examination Report for CN 201180017696.3, dated Oct. 18, 2013.
Rule 161/162 Communication for EP 11766613.1, dated Nov. 14, 2012.
Response to Rule 161/162 Communication for EP 11766613.1, filed May 17, 2013.
European Search Report for EP 11766613.1, dated Jan. 15, 2014.
Office Action for U.S. Appl. No. 13/079,878, dated Aug. 13, 2012.
International Search Report and Written Opinion for PCT/US2011/031163, dated May 23, 2011.
International Preliminary Report on Patentability Chapter I for PCT/US2011/031163, dated Oct. 9, 2012.
International Search Report and Written Opinion for PCT/US20120/032759, dated Sep. 28, 2012.
International Preliminary Report on Patentability Chapter I for PCT/US2012/032759, dated Oct. 8, 2013.
Invitation to Pay Additional Fees and, Where Applicable, Protest Fee for PCT/US2012/032759, dated Jul. 16, 2012.
Anderson et al., "Microarrayed Compound Screening to Identify Activators and Inhibitors of AMP-Activated Protein Kinase," J. of Biomolecular Screening (2004) 9:112 POI: 0.1177/1087057103260592.
Angenendt et al., "Cell-free expression and functional assay in a nanowell chip format," Analytical Chemistry (2004) 76(7):1844-49.
Angenendt et al.,"Generation of High Density Protein Microarrays by Cell-free in Situ Expression of Unpurified PCR Products," Molecular and Cellular Proteomics, (2006) Ch. 5.9, pp. 1658-1666.
Atkinson, Overview of Translation: Lecture Manuscript, U of Texas (2000) pp. 6.1-6.8.
Blokzijl et al., "Profiling protein expression and interactions: proximity ligation as a tool for personalized medicine," J Intern Med (2010) 268:232-245.
Burns et al., "Well-less, gel-permeation formats for ultra-HTS," DDT (2001) 6(12):S40-S47.
Carlson et al., "Formylglycine-generating Enzyme," J. of Biological Chemistry (2008) 283(29):20117-125.
Cha and Tilly, "Specificity, Efficiency and Fidelity of PCR," Genome Res. (1993) 3:518-29.
Chandra et al., "Cell-free synthesis-based protein microarrays and their applications," Proteomics ePub (2009) 5(6):717-30.
Chatterjee et al., "Microarray System," PLos One (2008) 3(9):e3265.
Cheng et al., "Sensitive Detection of Small Molecules by Competitive Immunomagnetic-Proximity Ligation Assay," Anal Chem (2012) 84:2129-2132.
Darmanis, et al., "ProteinSeq: High-Performance Proteomic Analyses by Proximity, Ligation and Next Generation Sequencing", PLos One (2011) 6(9):e25583 doi1 0.1371/journal.pone.0025583 20 1.
Ellington et al., "Antibody-based protein multiplex platforms: technical and operational challenges," Clin Chem (2010) 56(2):186-193.
Flanigon et al., "Multiplex protein detection with DNA readout via mass spectrometry," N Biotechnol (2013) 30(2):153-158.
Fredriksson et al., "Protein detection using proximity-dependent DNA ligation assays," Nature Biotech. (2002) 20:473-77.
Fredriksson et al., "Multiplexed protein detection by proximity ligation for cancer detection," Nature Methods (2007) 4(4):327-29.
Fredriksson et al., "Multiplexed proximity ligation assays to profile putative plasma biomarkers relevant to pancreatic and ovarian cancer," Clin. Chem. (2008) 5(3): 582-89.
Frese and Dierks, "Formylglycine Aldehyde Tag-Protein Engineering through a Novel Posttranslational Modification," ChemBioChem (2009) 10:425-27.
Fu et al., "Counting individual DNA molecules by the stochastic attachment of diverse labels," PNAS (2011) 108:9026-9031.
Gu et al., "Protein tag-mediated conjugation of oligonucleotides to recombinant affinity binders for proximity ligation," N Biotechnol (2013) 30(2):144-152.
Hammond et al., "Profiling cellular protein complexes by proximity ligation with dual tag microarray readout," (2012) 7(7):e40405.
He, "Cell-free protein synthesis: applications in proteomics and biotechnology," (2008) New Biotechnology 25:126-132.
He et al. , "In situ synthesis of protein arrays," Current Opinion in Biotechnology (2008) 19:4-9.
He et al. , "In situ synthesis of protein arrays," Current Opinion in Biotechnology (2008) 19:4-9 (Supplementary figures).
He et al., "Printing protein arrays from DNA arrays," Nature Methods (2008) 5:175-77.
Hedskog et al., "Dynamics of HIV-1 Quasispecies during Antiviral Treatment Dissected using Ultra-Deep Pyrosequencing," PLoS One (2010) 5(7)e11345.
Hendrickson et al., "High sensitivity multianalyte immunoassay using covalent DNA-labeled antibodies and polymerase chain reaction," Nucl. Acid Res. (1995) 23(9):522-529.
Hiatt et al., "Parallel, tag-directed assembly of locally-derived short sequence reads," Nature Methods (2010) 7(2):119-25.
Kozlov et al., "A High-Complexity Multiplexed Solution-Phase Assay for Profiling Protease Activity on Microarrays," Comb. Chem. and High Throughput (2008) 11:24-35.
Kozlov et al., "A Highly Scalable Peptide-Based Assay System for Proteomics," PLoS ONE (2012) 7(6):e37441.
Kozlov et al., "A Method for Rapid Protease Substrate Evaluation and Optimization," Comb. Chem. and High Throughput (2006) 9:481-487.
Kurz et al. , "cDNA-Protein Fusions: Covalent Protein-Gene Conjugates for the In Vitro Selection of Peptides and Proteins," Chem BioChem (2001) 2:666-672.
Larman et al., "Autoantigen discovery with a synthetic human peptidome", Nat Biotechnol (2011) 29(6):535-541.
Lundberg et al.,"Homogeneous antibody-based proximity extension assays provide sensitive and specific detection of low-abundant proteins in human blood", Nucleic Acids Res.(2011) 39(15):e1 02 (Abstract).
Lundberg et al., "Multiplexed homogeneous proximity ligation assays for high-throughput protein biomarker research in serological material," Mol Cell Proteomics (2011) 10(4):M110.004978.
Mir et al., "Sequencing by cyclic ligation and cleavage (CycLiC) directly on a microarray captured template," Nucleic Acids Research (2009) 37(1):e5-1.
Ng et al., "Massively parallel sequencing and rare disease," Human Molec. Genetics (2010) 19(2):R119-R124.
Niemeyer, "The developments of semisynthetic DNA/protein conjugates," Trends Biotechnol (2002) 20(9):395-401.
Proseek® Multiplex 96×96 User Manual (2013) Olink Bioscience, Uppsala, Sweden, 20 pages.
Ramachandran et al., "Next-generation high-density self-assembling functional protein arrays," Nature Methods (2008) 5(6):535-38.
Roberts and Szostak , "RNA-peptide fusions for the in vitro selection of peptides and proteins," PNAS USA(1997) 94:12297-12302.
Rouillard et al., "OligoArray 2.0: design of oligonucleotide probes for DNA microarrays using a thermodynamic approach," Nuc. Acid Research (2003)31 (12):3057-62.
Rush and Bertozzi, "New Aldehyde Tag Sequences Identified by Screening Formylglycine Generating Enzymes in Vitro and in Vivo," J. of American Chemical Society (2008) 130: 12240-41.
Rush and Bertozzi, "New Aldehyde Tag Sequences Identified by Screening Formylglycine Generating Enzymes in Vitro and in Vivo," J. of American Chemical Society (2008) 130: 12240-41 (2008) Supplement.
Schmitt et al., "Detection of ultra-rare mutations by next-generation sequencing," PNAS (2012) 109:14508-14523.
Takahashi and Roberts, "In Vitro Selection of Protein and Peptide Libraries Using mRNA Display," Nucleic Acid and Peptide Aptamers: Methods and Protocols (2009) 535:293-314.

(56) References Cited

OTHER PUBLICATIONS

Tolbert and Wong, "New methods for proteomic research: preparation of proteins with N-terminal cysteines for labeling and conjugation," Angew Chem Int Ed Engl (2002) 41(12):2171-2174.

Vogelstein and Kinzler, "Digital PCR," PNAS USA (1999) 96:9236-41.

Waichman et al., "Functional Immobilization and Patterning of Proteins by an Enzymatic Transfer Reaction", Anal Chem (2010) 82:1478-85.

Wong et al. "Direct Site-Selective Covalent Protein Immobilization Catalyzed by a Phosphopantetheinyl Transferase," J Am Chem Soc (2008) 130:12456-12464.

Xiao et al., "Direct determination of haplotypes from single DNA molecules," Nature Methods(2009) 6(3):199-01.

Yin et al., "Genetically encoded short peptide tag for versatile protein labeling by Sfp phosphopantetheinyl transferase," PNAS (2005) 102(44):15815-15820.

Zhang et al., "Assembling DNA through Affinity Binding to Achieve Ultrasensitive Protein Detection," Angew Chem Int Ed (2013) 52:2-10.

Zhang et al., "Binding-induced DNA assembly and its application to yoctomole detection of proteins," Anal Chem (2012) 84(2):877-884.

Zhou et al., "Genetically Encoded Short Peptide Tags for Orthogonal Protein Labeling by Sfp and AcpS Phosphopentetheinyl Transferases," ACS Chemical Biology (2007) 2(5):37-46.

Zlobec et al., "Next-generation tissue microarray (ngTMA) increases the quality of biomarker studies: an example using CD3, CD8, and CD45RO in the tumor microenvironment of six different solid tumor types," Journal of Translational Medicine (2013) 11:104.

Response to Patent Examination Report No. 1 for AU 2011237729, filed Mar. 3, 2014.

Response to First Examination Report for CN 201180017696.3, filed Mar. 3, 2014.

Response After Final Office Action for U.S. Appl. No. 13/266,568, filed Mar. 4, 2014.

Restriction Requirement for U.S. Appl. No. 13/442,637, dated May 17, 2012.

Response to Restriction Requirement for U.S. Appl. No. 13/442,637, filed Jun. 5, 2012.

Supplemental Response and Amendment for U.S. Appl. No. 13/442,637, filed Jun. 6, 2012.

Office Action for U.S. Appl. No. 13/442,637, dated Aug. 9, 2012.

Response to Office Action for U.S. Appl. No. 13/442,637, filed Oct. 9, 2012.

Final Office Action for U.S. Appl. No. 13/442,637, dated Dec. 20, 2012.

Response to Final Office Action for U.S. Appl. No. 13/442,637, filed Mar. 20, 2013.

Advisory Action for U.S. Appl. No. 13/442,637, dated Apr. 1, 2013.

Preliminary Amendment and remarks with filing of RCE for U.S. Appl. No. 13/442,637, filed Apr. 17, 2013.

Oleinikov et al. "Self-assembling protein arrays using electronic semiconductor microchips and in vitro translation," Journal of Proteome Research (2003) 2:313-319.

\* cited by examiner

FIG. 10

PEPTIDE CONSTRUCTS AND ASSAY SYSTEMS

CROSS-REFERENCE TO RELATED APPLICATIONS

The present application is a continuation of pending U.S. Ser. No. 13/442,637, filed Apr. 9, 2012, which claims priority to U.S. Ser. No. 61/473,709, filed Apr. 8, 2011, the contents of which are incorporated herein by reference.

NOTICE OF GOVERNMENT FUNDING

This invention was made with the support of the Federal Government under Grants GM090392; GM085884; and HG004284. The Federal Government may have rights in this invention.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 699932001101SeqList.txt, date recorded: Oct. 6, 2017, size: 8,812 bytes).

FIELD OF THE INVENTION

This invention relates to methods of producing such sets of peptide constructs and methods of using the peptide constructs sets in assay systems and other analyses.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Rapid advances in DNA sequencing have created a pressing need for new technologies that enable the translation of genomic sequence information into information about protein function at the level of the proteome. Proteomics, the study of the function, structure and interaction of proteins, requires the ability to produce and study proteins in a high throughput manner. Traditionally, one approach has been to use combinatorial chemical synthesis methods to make large collections of peptides. However, these methods provide a random sampling of all possible n-mers, and are therefore inefficient for generating compact collections of protein sequences that are enriched for sequences of high biological relevance, such as peptides representing the human proteome. Highly specific and sensitive high-throughput methods for assaying proteins as a large collection are also lacking. Protein microarrays are a useful tool for such high throughput analysis of proteins, but the availability of microarray technology for large scale proteomics studies is still very limited due to the difficulty and cost of protein production (see Henderson and Bradley, Curr. Opin. Biotechnol., 18(4):326-30 (2007), Epub 2007 Aug. 6; and Tapia, Methods Mol. Biol., 570:3-17 (2009)).

Traditionally, peptide arrays are made by spotting pre-synthesized peptides on a surface (Salisbury, et al, J. Am. Chem. Soc. 124(50):14868-70 (2002)) or by synthesizing peptides in spots on cellulose filter sheets using standard solid phase peptide synthesis, also known as the SPOT method (Frank, J. Immunol. Methods, 267(1):13-26 (2002)). However, the cost of generating arrays with tens of thousands or more spotted peptides is very high. This is a major impediment to the use of large arrays of peptides for most applications, and severely limits accessibility of large arrays to researchers. Several methods enable direct chemical synthesis of peptides in microarray format, which reduces costs, but these methods still have the major drawback of variability in the quality of the synthesized peptides (Antohe and Cooley, Methods Mol. Biol., 381:299-312 (2007)). Moreover, the direct fabrication process can be very slow and inefficient (Hilpert, et al., Nat. Protoc., 2:1333-49 (2007)).

Recently, methods for peptide array fabrication by in vitro translation have been developed, including protein in situ array (PISA) production (He and Taussig, Nucleic Acids Res., 29: e73 (2001)), nucleic acid programmable protein array (NAPPA) production (Ranachandran, et al., Science, 305:86-90 (2004)), DNA to protein array (DAPA) construction (He, Nat. Methods, 5:175-177 (2008), and arraying of proteins using in situ puromycin capture (Tao and Zhu, Nat. Biotech, 24:1253-1254 (2006)).

These approaches require individually synthesized nucleic acid templates, however, and the cost of these templates is higher than the cost of individual peptides arrayed by traditional methods. In addition, analysis of the peptides is limited to substrate-based systems.

The ability to manufacture large, high-quality, sequence-diverse peptide sets in solution, coupled with labeling methods and techniques compatible with high-throughput analysis of such large peptide sets, would enable high-throughput binding and enzymatic activity profiling studies having important applications in research, diagnostics and therapeutic development. The present invention addresses this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The methods of the present invention allow for production and analysis of large sets of peptide constructs in a cost-effective manner, employing molecular biological techniques that are both robust and easily parallelized. Rather than analyzing peptides directly, nucleic acids that identify the peptides are sequenced, allowing for rapid and inexpensive digital readout analysis. Moreover, in contrast to combinatorial methods used to date to generate peptide libraries, the peptide constructs of the present invention are designed to comprise specific peptide sequences of interest, and thus may be enriched for peptides that are biologically significant or relevant. Further, the methods of the present invention allow the construction of custom peptide construct sets encompassing hundreds, thousands, and millions of proteins; that is, peptide construct sets comprising the entire human proteome are well within the scope of the present invention, and can be manufactured at low cost.

Thus, in one embodiment the present invention provides a pool of custom-content peptide constructs comprising a nucleic acid portion and a peptide portion, wherein the custom-content peptide constructs are made from a pool of custom-designed oligonucleotides that have been synthesized by parallel synthesis on a solid support. In some aspects of this embodiment, the custom-designed oligonucleotides are synthesized by parallel synthesis on a solid support by sequence-directed synthesis.

In one embodiment, the invention provides a set of at least 5,000 distinct peptide constructs, each comprising a peptide portion and an identifying oligonucleotide portion, wherein the peptide portions are encoded by oligonucleotide sequences that are custom-designed so that at least 10% of the set of peptide constructs produced contain contiguous peptide sequences of at least 12 amino acids that have more than 80% amino acid identity to protein sequences encoded by up to 100 different species of organism. In some aspects at least 15%, 20%, 25%, 50%, or 75% or more of the set of peptide constructs produced contain contiguous peptide sequences of at least 13, 14, 15, 16, 17, 18, 19, 20 or more amino acids that have more than 85%, 90%, 95%, 97%, 99% or more amino acid identity to protein sequences encoded by up to 100 different species of organisms. In some aspects there are at least 500, 1,000, 2,500, or 4,000 distinct peptide constructs in the set, or 10,000, 25,000, 50,000, 100,000, 500,000, 1,000,000 or more distinct peptide constructs are in the set.

In some aspects of this embodiment, the species are eukaryotic species, and in some aspects of this embodiment, the species are mammalian species. In other aspects of this embodiment, the species are bacterial species. In some aspects, the species are human pathogens.

In various aspects, the peptide sequences of the peptide constructs are grouped into one or more sets of partially overlapping sequences. In some aspects, the peptide portion of the peptide construct is dissociated from the ribosome before being linked to the identifying nucleic acid. In some aspects of this embodiment, the set of peptide constructs comprises at least 100,000 distinct peptide constructs, each comprising a peptide portion of at least 10, 11, 12, 13, 14, 15 or more amino acids and an identifying oligonucleotide portion, wherein the peptide portions are encoded within oligonucleotide sequences that are custom-designed such that at least 90%, 95%, 97%, 99% or more of the sequences contain no more than one in-frame codon that can function as a stop codon in the translation system used to make the peptide constructs.

Yet another embodiment of the invention provides a set of at least 5,000 distinct peptide constructs, each comprising a peptide portion and an identifying oligonucleotide portion, wherein the peptide portions are encoded by oligonucleotide sequences that are custom-designed such that the peptide sequence diversity is no less than 1% of the encoding oligonucleotide sequence diversity. In some aspects of this embodiment, the peptide sequence diversity of the set of peptide constructs is no less than 10% of the encoding oligonucleotide sequence diversity, and in some aspects, the peptide sequence diversity of the set of peptide constructs is no less than 15%, 25%, or 50% of the encoding oligonucleotide sequence diversity.

In some aspects of this embodiment of the invention, the oligonucleotide sequences are first produced by parallel synthesis. In some aspects, the size of the set is at least 100,000 distinct peptide constructs, and in other aspects, the size of the set is at least 250,000, 500,000, 750,000, 1,000,000, 1,500,000, 2,500,000 or more distinct peptide constructs.

The present invention also provides in one embodiment a method for analyzing a sample using a set of peptide constructs, each peptide construct comprising a custom-designed peptide portion and an identifying nucleic acid portion, comprising the steps of performing an assay on the set of peptide constructs, where some of the peptide constructs are acted upon (reacted, modified or transformed) by assay agents; separating the peptide constructs that are acted upon (reacted, modified or transformed) by the assay agents from the peptide constructs that are not acted upon (unreacted, unmodified or untransformed) by the assay agents; and determining the identities of substantially all of the peptide constructs of either the peptide constructs that were acted upon by the assay agents or the peptide constructs that were not acted upon by the assay agents by analyzing the nucleic acid portion of the peptide constructs.

In some aspects of this embodiment, the action of the assay agents results in some of the peptide constructs being modified permanently or non-permanently. In some aspects of this method embodiment, the sequences of the nucleic acid portions of the custom-content peptide constructs are determined in parallel; and in some aspects, the analyzing step is performed by digital sequencing, and in yet other aspects, the analyzing step is performed by hybridization to a microarray. In some aspects of this method embodiment, the sequences of at least one thousand nucleic acid portions of the custom-content peptide constructs are determined in parallel; and in other aspects, the sequences of at least one hundred thousand nucleic acid portions of the custom-content peptide constructs are determined in parallel, and in other aspects the sequences of at least one million nucleic acid portions of the peptide constructs are determined in parallel.

In some aspects, at least 50,000, 100,000, 250,000, 500,000 or 750,000 different peptide constructs are assayed. In other aspects, at least 1,000,000, 1,250,000, 1,500,000, 2,000,000 or more different peptide constructs are assayed.

In addition, the invention provides a research tool comprising a set of at least 5,000 distinct peptide constructs, each comprising a peptide portion and an identifying oligonucleotide portion, wherein the peptide portions are encoded by oligonucleotide sequences that are custom-designed such that the peptide sequence diversity is no less than 1% of the encoding oligonucleotide sequence diversity. In some aspects of this embodiment, the peptide sequence diversity of the set of peptide constructs is no less than 10% of the encoding oligonucleotide sequence diversity, and in some aspects, the peptide sequence diversity of the set of peptide constructs is no less than 15%, 25%, or 50% of the encoding oligonucleotide sequence diversity.

In other embodiments, the invention provides a system for analyzing a sample where a set of peptide constructs is provided by a user, where each peptide construct comprises a custom-designed peptide portion and an identifying nucleic acid portion; performing an assay on the set of peptide constructs, where some of the peptide constructs are acted upon (reacted, modified or transformed) by assay agents; separating the peptide constructs that are acted upon (reacted, modified or transformed) by the assay agents from the peptide constructs that are not acted upon (unreacted, unmodified or untransformed) by the assay agents; determining the identities of substantially all of the peptide constructs of either the peptide constructs that were acted upon by the assay agents or the peptide constructs that were not acted upon by the assay agents by analyzing the nucleic acid portion of the peptide constructs; and reporting the results of the determining step to the user.

In yet another embodiment there is provided a method of preparing a set of peptide constructs comprising: providing a substrate having partitioned reaction volumes where the reaction volumes comprise DNA oligonucleotides, where the DNA oligonucleotides comprise a promoter, a ribosome binding site and a region coding for a peptide of interest and an amino acid capture tag sequence that is a substrate for a peptide modifying enzyme; providing to the reaction volumes an adaptor comprising a first nucleic acid ligation region, a second nucleic acid ligation region and a capture moiety; and a reaction mix comprising an RNA polymerase, nucleotides and cofactors for transcription; RNA ligase, a splint sequence, and cofactors for ligation; ribosomes, amino acids, and cofactors for translation; and an enzyme that catalyzes the attachment of the capture tag on a translated peptide to the capture moiety of the adaptor; providing reaction conditions to the reaction volumes to allow transcription of the DNA oligonucleotide to form RNA, ligation of the adaptors to the RNA, translation of the RNA to produce peptides, and attachment of the capture tag on the peptides to the capture moieties of the adaptors to form peptide constructs; and pooling the peptide constructs from the reaction volumes.

In preferred aspects of this embodiment, the reaction volumes contain DNA oligonucleotides that code for different peptides of interest, and in preferred aspects, at least a portion of the DNA oligonucleotides are constructed using parallel chemical synthesis on the substrate. In some aspects, the coding regions of for the DNA oligonucleotides are synthesized using parallel chemical synthesis on the substrate, and the promoter and ribosome binding site regions are synthesized separately and added via ligation to the coding regions, and in other aspects, the promoter, ribosome binding site and coding regions of the DNA oligonucleotides are synthesized using parallel chemical synthesis on the substrate.

In preferred embodiments, phosphopantetheinyl transferase catalyzed site-specific attachment is employed. In some aspects of this embodiment, the capture moiety is coenzyme A, the amino acid capture tag is an S6 tag or ybbR tag and the enzyme that catalyzes the attachment of the S6 capture tag to coenzyme A is SFP synthase.

These and other method for producing peptide constructs and utilizing such peptide constructs in assay systems are described in more detail herein.

DESCRIPTION OF THE FIGURES

FIG. 10 illustrates the relative sequencing counts for overlapping 8-mer peptides representing a part of HCV polyprotein.

Figure 1:
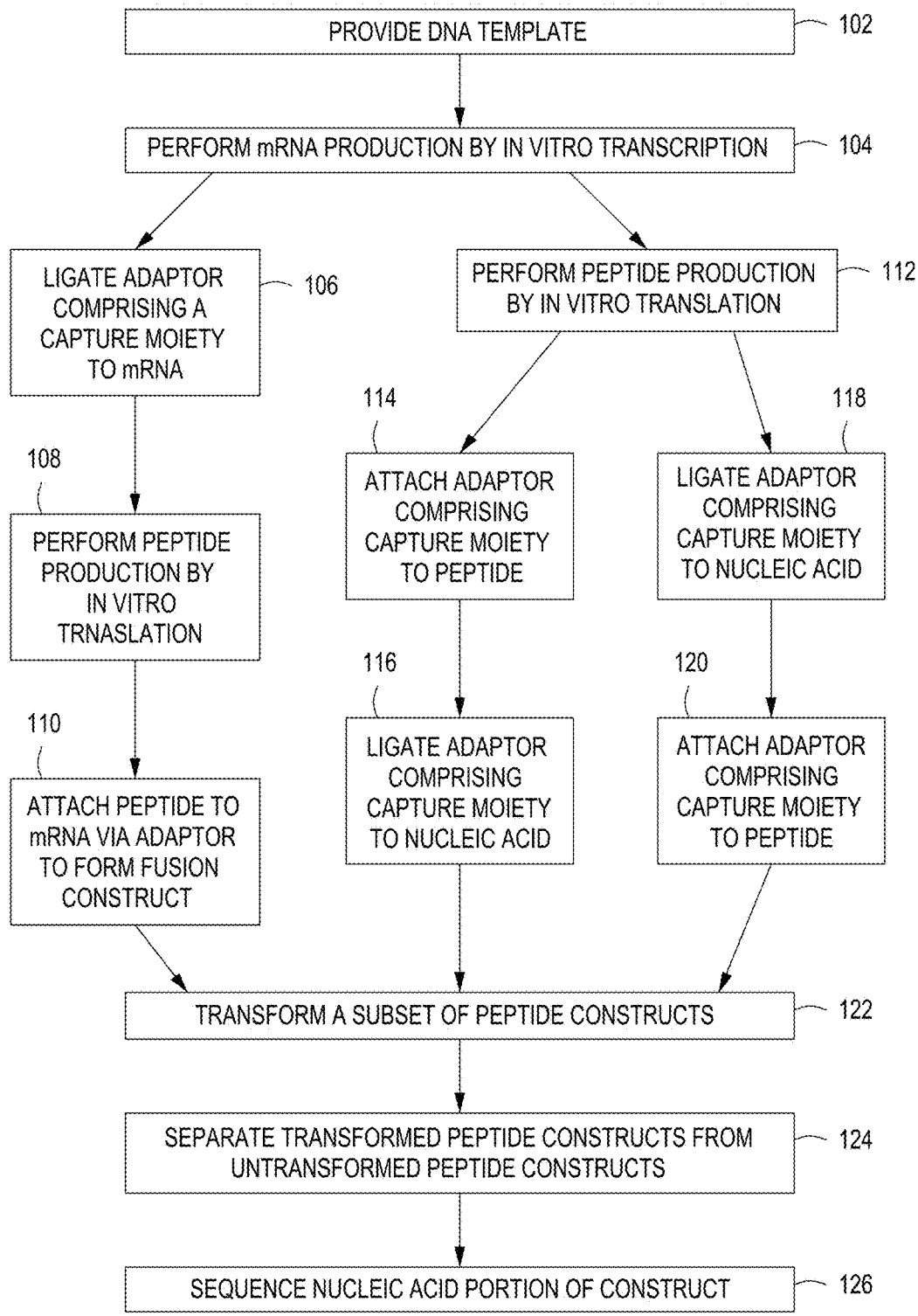
FIG. 1 illustrates alternative embodiments of the inventive method for creating peptide constructs according to the present invention.

It should be noted that the features of the various peptide fusion constructs, oligonucleotides, binding agents, C-terminus binding moiety, amino acid capture tag, and various other regions within the oligonucleotides, adaptors and peptide fusion constructs (such as, for example, coding regions, primer sites, ligation sites, capture agents, binding agents, and the like) are not drawn to scale; rather, the features are presented in a representational manner only.

Definitions

The terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated.

The term "affinity tag" or "affinity capture agent" as used herein refers to one member of a binding pair that selectively binds to a capture agent.

The term "antibody" as used herein is intended to refer to an entire immunoglobulin or antibody or any functional fragment of an immunoglobulin molecule which is capable of specific binding to an antigen (antibodies and antigens are "binding partners" as defined herein). "Antibody" as used herein is meant to include the entire antibody as well as any antibody fragments capable of binding the antigen or antigenic fragment of interest. Examples of such peptides include complete antibody molecules, antibody fragments, such as Fab, F(ab')2, CDRS, VL, VH, and any other portion of an antibody that is capable of specifically binding to an antigen. Antibodies for assays of the invention are immunoreactive or immuno specific for, and therefore specifically and selectively bind to, proteins either detected (i.e., biological targets) or used for detection (i.e., probes) in the assays of the invention.

The term "binding pair" means any two molecules that are known to selectively bind to one another. In the case of two proteins, the molecules selectively bind to one another as described in more detail herein. Such binding may include covalent and/or non-covalent binding. Examples include, but are not limited to, biotin and avidin; biotin and streptavidin; an antibody and its particular epitope; and the like.

The term "capture agent" as used herein refers to any moiety that allows capture of a peptide construct via binding to or linkage with an affinity tag of the peptide construct. The binding between the capture agent and its affinity tag may be a covalent bond and/or a non-covalent bond. A capture agent includes, e.g., a member of a binding pair that selectively binds to an affinity tag on a fusion peptide, a chemical linkage that is added by recombinant technology or other mechanisms, co-factors for enzymes and the like. Capture agents can be associated with a construct using conventional techniques including hybridization, crosslinking (e.g., covalent immobilization using a furocoumarin such as psoralen), ligation, attachment via chemically-reactive groups, introduction through post-translational modification and the like.

The term "complementary" refers to the topological compatibility or interactive structure of interacting surfaces of a nucleic acid binding pair. Preferred complementary structures have binding affinity for each other and the greater the degree of complementarity the nucleic acids have for each other the greater the hybridization between the structures.

The term "C-terminus binding moiety" or "C-terminus binding entity" refers to any catalytic activity of the ribosomal peptidyl transferase function. Typically, such molecules contain (i) a nucleotide or nucleotide-like moiety (for example, adenosine or an adenosine analog (di-methylation at the N-6 amino position is acceptable)), (ii) an amino acid or amino acid-like moiety (for example, any of the 20 D- or L-amino acids or any amino acid analog thereof (for example, O-methyl tyrosine or any of the analogs described by Ellman, et al., Meth. Enzymol. 202:301 (1991)), and (iii) a linkage between the two (for example, an ester, amide, or ketone linkage at the 3' position or, less preferably, the 2' position); preferably, this linkage does not significantly perturb the pucker of the ring from the natural ribonucleotide conformation. C-terminus binding moieties may also possess a nucleophile, which may be, without limitation, an amino group, a hydroxyl group, or a sulfhydryl group. In addition, C-terminus binding moieties may be composed of nucleotide mimetics, amino acid mimetics, or mimetics of the combined nucleotide-amino acid structure. By C-terminus binding moiety being positioned "at the 3' end" of a protein coding sequence is meant that C-terminus binding moiety is positioned after the final codon of that protein coding sequence. This term includes, without limitation, a C-terminus binding moiety that is positioned precisely at the 3' end of the protein coding sequence as well as one which is separated from the final codon by intervening coding or non-coding sequence (for example, a sequence corresponding to a pause site). This term also includes constructs in which coding or non-coding sequences follow (that is, are 3' to) the C-terminus binding moiety. In addition, this term encompasses, without limitation, a C-terminus binding moiety that is covalently bonded (either directly or indirectly through intervening nucleic acid sequence) to the protein coding sequence, as well as one that is joined to the protein coding sequence by some non-covalent means, for example, through hybridization using a second nucleic acid sequence that binds at or near the 3' end of the protein coding sequence and that itself is bound to a C-terminus binding moiety.

The term "custom-content" or "custom-design" refers to designing sequences for a pool of chemical moieties, e.g., oligonucleotides or peptides, where at least a portion of the coding region of the oligonucleotide or peptide is designed in a substantially non-combinatorial manner, i.e., resulting in sequence diversity that is not substantially random in nature.

"Hybridization" refers to the process in which two single-stranded polynucleotides bind non-covalently to form a stable double-stranded polynucleotide. The resulting (usually) double-stranded polynucleotide is a "hybrid" or "duplex." "Hybridization conditions" will typically include salt concentrations of approximately less than 1M, often less than about 500 mM and may be less than about 200 mM. A "hybridization buffer" is a buffered salt solution such as 5% SSPE, or other such buffers known in the art. Hybridization temperatures can be as low as 5° C., but are typically greater than 22° C., and more typically greater than about 30° C., and typically in excess of 37° C. Hybridizations are often performed under stringent conditions, i.e., conditions under which a primer will hybridize to its target subsequence but will not hybridize to the other, non-complementary sequences. Stringent conditions are sequence-dependent and are different in different circumstances. For example, longer fragments may require higher hybridization temperatures for specific hybridization than short fragments. As other factors may affect the stringency of hybridization, including base composition and length of the complementary strands, presence of organic solvents, and the extent of base mismatching, the combination of parameters is more important than the absolute measure of any one parameter alone. Generally stringent conditions are selected to be about 5° C. lower than the $T_m$ for the specific sequence at a defined ionic strength and pH. Exemplary stringent conditions include a salt concentration of at least 0.01M to no more than 1M sodium ion concentration (or other salt) at a pH of about 7.0 to about 8.3 and a temperature of at least 25° C. For example, conditions of 5×SSPE (750 mM NaCl, 50 mM sodium phosphate, 5 mM EDTA at pH 7.4) and a temperature of approximately 30° C. are suitable for allele-specific hybridizations, though a suitable temperature depends on the length and/or GC content of the region hybridized.

The term "oligonucleotide" is used herein to mean a linear polymer of nucleotide monomers. As used herein, the term may refer to single-stranded or double-stranded forms. Monomers making up nucleic acids and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like, to form duplex or triplex forms. Such monomers and their internucleosidic linkages may be naturally occurring or may be analogs thereof, e.g., naturally occurring or non-naturally occurring analogs. Non-naturally occurring analogs may include peptide nucleic acids, locked nucleic acids, phosphorothioate internucleosidic linkages, bases containing linking groups permitting the attachment of labels, such as fluorophores, or haptens, and the like. Whenever the use of an oligonucleotide or nucleic acid requires enzymatic processing, such as extension by a polymerase, ligation by a ligase, or the like, one of ordinary skill would understand that oligonucleotides or nucleic acids in those instances would not contain certain analogs of internucleosidic linkages, sugar moieties, or bases at any or some positions, when such analogs are incompatible with enzymatic reactions. Nucleic acids typically range in size from a few monomeric units, e.g., 5-300, when they are usually referred to as "oligonucleotides," to several hundred thousand or more monomeric units. Whenever a nucleic acid or oligonucleotide is represented by a sequence of letters (upper or lower case), such as "ATGCCTG," it will be understood that the nucleotides are in 5' to 3' order from left to right and that "A" denotes deoxyadenosine, "C" denotes deoxycytidine, "G" denotes deoxyguanosine, and "T" denotes deoxythymidine, "I" denotes deoxyinosine, "U" denotes uridine, unless otherwise indicated or obvious from context. Usually nucleic acids comprise the natural nucleosides (e.g., deoxyadenosine, deoxycytidine, deoxyguanosine, deoxythymidine for DNA or their ribose counterparts for RNA) linked by phosphodiester linkages; however, they may also comprise non-natural nucleotide analogs, e.g., modified bases, sugars, or internucleosidic linkages. To those skilled in the art, where an enzyme has specific oligonucleotide or nucleic acid substrate requirements for activity, e.g., single-stranded DNA, RNA/DNA duplex, or the like, then selection of appropriate composition for the oligonucleotide or nucleic acid substrates is well within the knowledge of one of ordinary skill, especially with guidance from treatises, such as Sambrook et al., *Molecular Cloning*, 2d Ed. (1989) (Cold Spring Harbor Laboratory, New York), and like references.

The terms "peptide", "polypeptide," and the like are used interchangeably herein, and refer to a polymeric form of amino acids of any length, chemically or biochemically modified or derivatized amino acids, and polypeptides having modified peptide backbones.

The term "peptide construct" as used herein, refers to a peptide of any length attached to an identifying oligonucleotide. The attachment may be via an intervening linker and the attachment may be covalent or non-covalent. The identifying oligonucleotide may be the message that was translated to form the peptide portion of the construct, or it may be any other sequence that is known and can be used to identify the attached peptide by sequencing. 'Peptide construct sets' refer to a pool of peptide constructs generated from a custom-designed set of oligonucleotides. The sets may contain as few as one copy per species of peptide construct but typically contain many copies of each peptide construct.

The term "research tool" as used herein refers to any composition or assay of the invention used for scientific enquiry, academic or commercial in nature, including the development of pharmaceutical and/or biological therapeutics and diagnostics. The research tools of the invention are not intended to be therapeutic or to be subject to regulatory approval; rather, the research tools of the invention are intended to facilitate research and aid in such development activities, including any activities performed with the intention to produce information to support a regulatory submission.

The term "selectively binds", "selective binding" and the like as used herein, when referring to a binding partner (e.g., protein, nucleic acid, antibody, etc.), refers to a binding reaction of two or more binding partners with high affinity and/or complementarity to ensure selective hybridization under designated assay conditions. Typically, signal that is due to specific binding will be at least three times the standard deviation of the background signal. Thus, under designated conditions the binding partner binds to its particular "target" molecule and does not bind in a significant amount to other molecules present in the sample.

"Sequencing", "sequence determination" and the like means determination of information relating to the nucleotide base sequence of a nucleic acid. Such information may include the identification or determination of partial as well as full sequence information of the nucleic acid. Sequence information may be determined with varying degrees of statistical reliability or confidence. In one aspect, the term includes the determination of the identity and ordering of a plurality of contiguous nucleotides in a nucleic acid. "High throughput digital sequencing" or "next generation sequencing" means sequence determination using methods that determine many (typically thousands to billions) of nucleic acid sequences in an intrinsically parallel manner, i.e. where DNA templates are prepared for sequencing not one at a time, but in a bulk process, and where many sequences are read out preferably in parallel, or alternatively using an ultra-high throughput serial process that itself may be parallelized. Such methods include but are not limited to pyrosequencing (for example, as commercialized by 454 Life Sciences, Inc., Branford, Conn.); sequencing by ligation (for example, as commercialized in the SOLiD™ technology, Life Technology, Inc., Carlsbad, Calif.); sequencing by synthesis using modified nucleotides (such as commercialized in TruSeq™ and HiSeq™ technology by Illumina, Inc., San Diego, Calif., HeliScope™ by Helicos Biosciences Corporation, Cambridge, Mass., and PacBio RS by Pacific Biosciences of California, Inc., Menlo Park, Calif.), sequencing by ion detection technologies (Ion Torrent, Inc., South San Francisco, Calif.); sequencing of DNA nanoballs (Complete Genomics, Inc., Mountain View, Calif.); nanopore-based sequencing technologies (for example, as developed by Oxford Nanopore Technologies, LTD, Oxford, UK), and like highly-parallelized sequencing methods.

The term "$T_m$" is used in reference to the "melting temperature." The melting temperature is the temperature at which a population of double-stranded nucleic acid molecules becomes half dissociated into single strands. Several equations for calculating the $T_m$ of nucleic acids are well known in the art. As indicated by standard references, a simple estimate of the $T_m$ value may be calculated by the equation, $T_m=81.5+0.41$ (% G+C), when a nucleic acid is in aqueous solution at 1M NaCl (see, e.g., Anderson and Young, Quantitative Filter Hybridization, in *Nucleic Acid Hybridization* (1985)). Other references (e.g., Allawi and SantaLucia, Jr., Biochemistry 36:10581-94 (1997)) include alternative methods of computation that take structural and environmental, as well as sequence characteristics, into account for the calculation of $T_m$.

DETAILED DESCRIPTION OF THE INVENTION

The practice of the techniques described herein may employ, unless otherwise indicated, conventional techniques and descriptions of organic chemistry, polymer technology, molecular biology (including recombinant techniques), cell biology, biochemistry, and sequencing technology, which are within the skill of those who practice in the art. Such conventional techniques include polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds., *Genome Analysis: A Laboratory Manual Series* (Vols. I-IV) (1999); Weiner, Gabriel, Stephens, Eds., *Genetic Variation: A Laboratory Manual* (2007); Dieffenbach, Dveksler, Eds., *PCR Primer: A Laboratory Manual* (2003); Bowtell and Sambrook, *DNA Microarrays: A Molecular Cloning Manual* (2003); Mount, *Bioinformatics: Sequence and Genome Analysis* (2004); Sambrook and Russell, *Condensed Protocols from Molecular Cloning: A Laboratory Manual* (2006); and Sambrook and Russell, *Molecular Cloning: A Laboratory Manual* (2002) (all from Cold Spring Harbor Laboratory Press); Stryer, *Biochemistry* (4th Ed.) (1995) W.H. Freeman, New York N.Y.; Gait, "*Oligonucleotide Synthesis: A Practical Approach*" (2002) IRL Press, London; Nelson and Cox, *Lehninger, Principles of Biochemistry* (2000) $3^{rd}$ Ed., W. H. Freeman Pub., New York, N.Y.; and Berg, et al., *Biochemistry* (2002) $5^{th}$ Ed., W.H. Freeman Pub., New York, N.Y., all of which are herein incorporated in their entirety by reference for all purposes.

Note that as used herein and in the appended claims, the singular forms "a," "an," and "the" include plural referents unless the context clearly dictates otherwise. Thus, for example, reference to "a construct" refers to one or more copies of such construct, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, formulations and methodologies that may be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

The Invention In General

The methods of the present invention allow for production and analysis of large sets of peptide constructs in a cost-effective manner, employing molecular biological techniques that are both robust and easily parallelized. For example, in preferred embodiments a set of in silico-designed oligonucleotide templates, capable of producing a custom set of peptide sequences, is generated by employing low cost microarray-based oligonucleotide synthesis of the variable or unique portions of each template while portions of the oligonucleotide that are common among many templates are generated by other methods, such as bulk synthesis, and then coupled to the unique portions via, e.g., ligation.

The set of oligonucleotide templates is used to produce a set of peptide constructs in a parallel fashion by one or more biochemical reactions that would ordinarily include translation or coupled transcription and translation, as well as covalent or non-covalent binding of the peptides to identifying oligonucleotides. In some most-preferred embodiments the binding is accomplished via an adaptor molecule which includes a capture moiety capable of binding a specific region, or capture tag, on the peptide. Also, rather than analyzing the peptides directly, nucleic acids that identify the peptides in a peptide construct are sequenced, allowing for rapid and inexpensive digital readout and analysis. Moreover, in contrast to combinatorial methods used to generate peptide libraries of all possible n-mers—which provide a random sampling rather than a targeted sampling of peptides—the peptide constructs of the present invention are designed to comprise specific peptide sequences of interest, and thus are enriched for peptides that are biologically significant or relevant. Importantly, the peptide constructs of the invention can be engineered to include functional peptides, including entire proteins, peptide domains, active sites, and the like, including functional proteins that are generally difficult to isolate from in vivo sources, e.g., insoluble proteins such as prions or beta amyloid peptides.

The peptide construct sets of the invention can be utilized to analyze peptide sequences, testing virtually any activity that is mediated by a protein or requires a protein interaction. For example, the peptide construct sets of the present invention can be used to identify epitope binding sites, as well as to identify preferred binding sites; and to identify kinase phosphorylation sites, as well as to identify preferred phosphorylation sites; and to identify protease cleavage sites, as well as analyzing proteolytic activity of proteases.

Further, the methods of the present invention allow the construction of peptide construct sets encompassing hundreds, thousands, and millions of proteins. Specifically, the peptide construct sets of the present invention may contain up to 5,000; 10,000; 25,000; 50,000; 100,000; 250,000; 500,000; 750,000; 1,000,000; 1,500,000; 2,000,000; 2,500,000; 5,000,000; 10,000,000 different peptides or more. Peptide construct sets comprising the human proteome are well within the scope of the present invention, and can be manufactured at low cost. For example, a library of peptide constructs representing an individual human's proteome could be constructed and used to screen for the presence of antibodies in sera; specifically, a peptide construct set comprising an individual's proteome or one or more reference proteomes could be used to screen for antibodies associated with cancers or autoimmune diseases.

In one preferred embodiment, a collection of messenger RNAs (mRNAs), produced by in vitro transcription of the set of oligonucleotide templates, is converted into peptide constructs by in vitro translation of the mRNAs, where the translated mRNA remains associated with the synthesized peptide of interest after translation via, e.g., a C-terminus binding moiety. This ensures that each peptide construct in the set will bear the correct identifying sequence irrespective of the number of different templates and peptides in the collection, thus the full collection of peptides can be formed in a single reaction volume. The complexity of the peptides within such a set of peptide constructs reflects the complexity of the original mRNAs produced, which in turn reflects the complexity of the oligonucleotides used for transcription. Once the mRNA-peptide constructs are produced, the mRNA portion can be reverse transcribed into cDNA to produce robust cDNA-peptide constructs. The peptide constructs may then be used in a variety of peptide assays or analyses. Once the assays have been performed, reacted (or transformed or modified) peptide constructs are separated from unreacted (or untransformed or unmodified) peptide constructs, and the cDNAs associated with the reacted (or unreacted) peptide constructs are sequenced, where the cDNA sequences identify the reacted (or unreacted) peptides.

In a second preferred embodiment, each peptide construct is made in a separate reaction volume via a novel "one-pot" reaction. The "one-pot" reaction combines a number of biochemical reactions so that they are carried out contemporaneously in the same reaction volume. Each reaction is adapted so that it can be carried out in a reaction environment that is compatible with the other reactions. Conveniently, the resulting 'one-pot' reaction can then be parallelized, for example by utilizing technologies that enable the formation of many separately partitioned reaction volumes in parallel. In preferred embodiments this is accomplished by the use of a microfluidic device according to the methods of U.S. Ser. No. 13/283,906, filed Oct. 28, 2011 and as described herein infra, or any other method(s), which can be used to provide multiple reaction volumes spatially isolated from one another, e.g. by an air gap, immiscible liquid or solid barrier, e.g., emulsion, microtiter plate. This approach enables large sets of constructs to be made efficiently. Thus, the present invention provides several exemplary embodiments that enable large sets of nucleic acid sequences of interest, that are specified in silico, to be converted into collections of peptide constructs. These peptide constructs can then be assayed in a multiplexed fashion.

FIG. 1 illustrates three paths of a simplified method 100 according to one embodiment of the present invention. The steps shown in simplified method 100 are described in further detail in this Detailed Description infra. At step 102, a DNA template is provided, and mRNA is produced by in vitro transcription at step 104. In one path of method 100, adaptors comprising a capture moiety are ligated to the mRNAs at step 106. At step 108, the mRNAs now comprising an adaptor are translated to form peptides, and at step 110, the peptides are attached to the mRNA to form peptide constructs. Once the peptide constructs are formed, analysis can be performed on the peptide portion of the constructs. At step 122, all peptide constructs are subjected to assay conditions where a portion of the peptides are transformed (or reacted or modified) via e.g. cleavage, phosphorylation or binding, depending on the nature of the assay. At step 124, the transformed peptide constructs are separated from the untransformed peptide constructs. In step 126, the nucleic acid portion of either the transformed (or modified) constructs or untransformed (or modified) constructs may be sequenced to determine the identity of the peptides in each population.

In another path of method 100, after steps 102 and 104, peptides are produced by in vitro translation at step 112. At step 114, adaptors comprising capture moieties are attached to the peptides, and at step 116, the adaptors are then ligated to nucleic acids to form peptide constructs. As before, analysis is performed by construct transformation in step 122, separation of the transformed and untransformed constructs in step 124 and identification by e.g. sequencing in step 126.

In yet another path of method 100, after steps 102 and 104, peptides are produced by in vitro translation at step 112. At step 118, adaptors comprising capture moieties are ligated to nucleic acids, and at step 120, the adaptors are attached to the peptides formed by the in vitro translation reaction to form peptide constructs. Again, once the constructs are formed, analysis is performed by construct transformation in step 122, separation of the transformed and untransformed constructs in step 124 and identification by e.g. sequencing in step 126.

Although there are three paths for peptide construct formation shown in FIG. 1, it should be noted that in the "one-pot" embodiments of the invention, the transcription, translation, ligation, and attachment steps are taking place contemporaneously. Thus, despite FIG. 1 portraying the reaction of the present invention in a sequential, step-wise fashion, the reactions that form the nucleic acid-peptide constructs in reality may occur simultaneously, via each of the exemplary paths.

Production of Oligonucleotides and In Vitro Transcription

Figure 2:
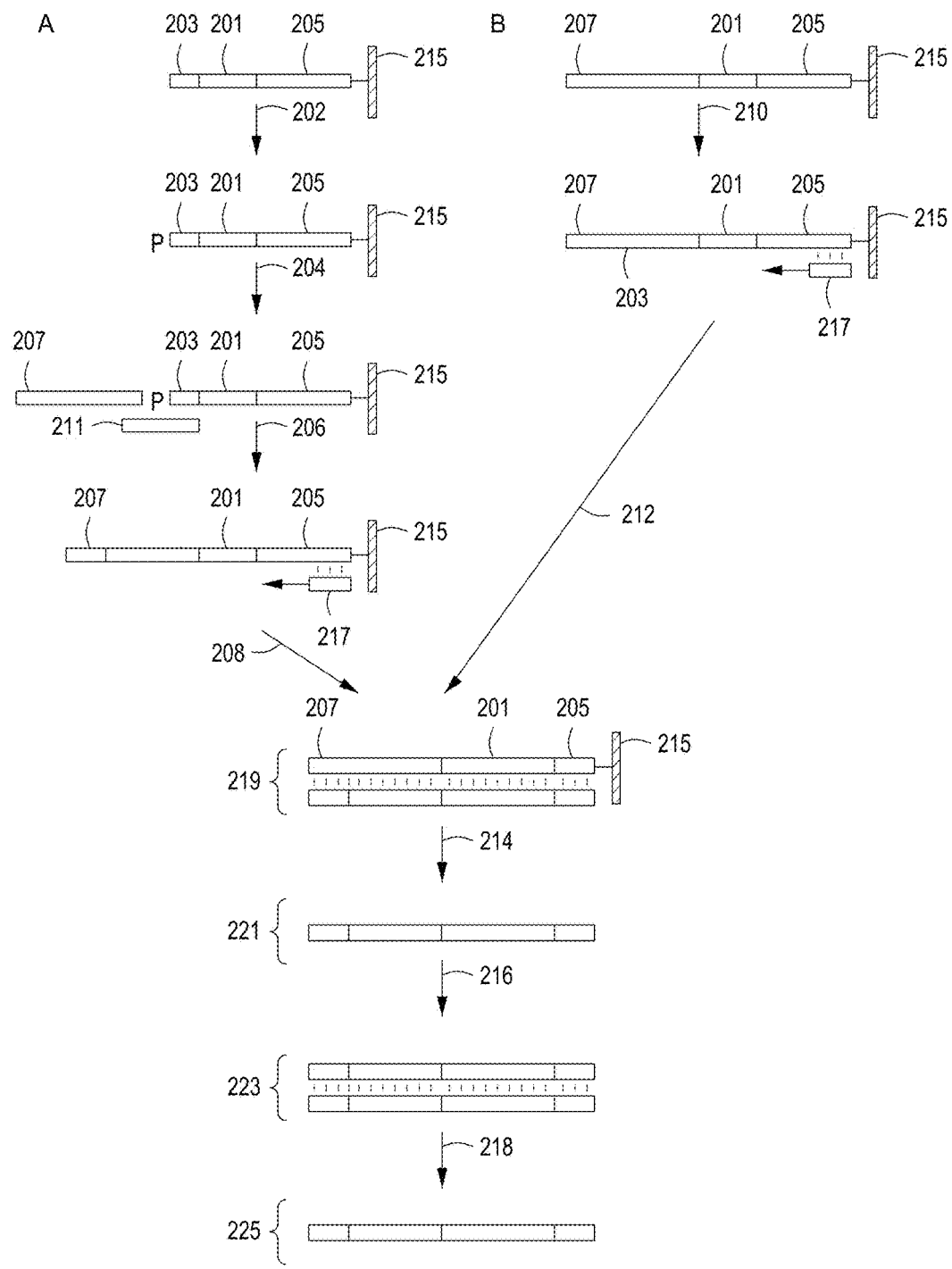
FIG. 2 illustrates exemplary methods for producing RNAs for use in synthesizing the peptide constructs of the invention.

FIG. 2 illustrates exemplary methods for synthesizing the set of oligonucleotides to be transcribed. In a preferred embodiment, illustrated in path A, a set of variable oligonucleotides is constructed using parallel chemical synthesis on the surface of high-complexity microarrays, and an additional common sequence oligonucleotide, synthesized separately, is ligated to the variable oligonucleotides to create transcription templates. The combination of synthesis and ligation enables the addition of 5' constant sequences to the array-synthesized variable sequences to efficiently create longer, sequence-defined oligonucleotides to be used for transcription and creation of the peptide constructs. For ease of description, the variable oligonucleotide is referred to as a "coding oligonucleotide" and the common oligonucleotide is referred to as a "promoter oligonucleotide", in reference to a primary feature that each oligonucleotide contributes to the final oligonucleotide after the two portions are joined. Generally, the coding oligonucleotide comprises the coding sequences for the peptides of interest, and the promoter oligonucleotide comprises nucleic acid sequences for the initiation of transcription and translation, common N- and C-terminal peptide tags, and the like. It should be noted that, in many embodiments and as described in more detail infra, the coding oligonucleotide will comprise non-coding sequences and the promoter oligonucleotide will comprise coding sequences, where such coding sequences most typically do not vary substantially from one peptide construct to another. Path B illustrates an alternative embodiment, wherein the entire oligonucleotide template can be created by parallel synthesis, provided that high fidelity synthesis of long enough oligonucleotides in achieved.

Returning to path A of FIG. 2, a single-stranded oligonucleotide encoding a peptide coding sequence 201 is synthesized on an array surface 215 and phosphorylated using T4 polynucleotide kinase. Many oligonucleotides can be synthesized and processed in parallel. In addition, each of the array-synthesized oligonucleotides has, e.g., universal sequences 203 and 205 at the 5' and 3' ends. Universal sequence 203 is complementary to a portion of a splint oligonucleotide 211 to be used in a splint ligation reaction. Universal sequence 205 may be used to code for, e.g., peptide tags, one or more primer hybridization sites, a region for ligation of a DNA adaptor, and the like, and combinations thereof.

In certain embodiments, the length of the coding sequence 201 may be, e.g., up to 30 nucleotides, coding for up to 10-mer peptides; in other embodiments the length of the coding sequence may be longer, e.g., up to 40, 60, 75, or 90 nucleotides, or longer, provided the synthesis techniques employed are capable of generating high quality oligonucleotides of such lengths. At step 202, the 5' end of the oligonucleotide on the array is phosphorylated so that a non-coding oligonucleotide can be ligated to the 5' end. At step 204, the non-coding oligonucleotide, 207, comprising a promoter region such as a T7 promoter region, and a ribosomal binding site (RBS) and, in some embodiments, N-terminal peptide tag, is added to the coding oligonucleotide on the array, along with splint oligonucleotide 211 and, e.g., T4 DNA ligase. Regions 207 may comprise additional sequences useful in the methods.

Generally, the oligonucleotides used for transcription may be created by synthesis methods known in the art. The oligonucleotides comprise a coding region, some portion of which varies amongst the oligonucleotides used for transcription, and promoter regions which typically do not vary, or vary in a more limited way, amongst the oligonucleotides used for transcription. As described thus far, one preferred method to obtain the oligonucleotides used for transcription is to synthesize the variable coding region on a microarray, and, once the variable coding region is synthesized, ligate an oligonucleotide comprising the promoter region, and optionally additional coding sequences, to the arrayed oligonucleotides.

Almost any technique for the generation of oligonucleotide arrays can be used, including but not limited to, production of arrays using the Affymetrix GeneChip technology (Affymetrix, Santa Clara, Calif.), including techniques disclosed in U.S. Pat. Nos. 7,736,906, 7,691,330, 7,547,775, 5,744,305, 5,677,195, 5,143,854 and U.S. Pat. Appln. Nos. 20100305006 and 20090192050; Agilent microarray technologies (Agilent Technologies, Inc., Santa Clara, Calif.), including but not limited to techniques disclosed in U.S. Pat. Nos. 7,642,097, 7,588,889, 656,740; 6,613,893; 6,599,693; 6,589,739; 6,587,579; 6,420,180; 6,387,636; 6,309,875; 6,232,072; 6,221,653; and 6,180,351 and U.S. Appl No. 20060078889; Illumina) micro array technology (Illumina, Inc., San Diego, Calif., including but not limited to synthesis techniques disclosed in disclosed in U.S. Pat. Nos. 6,942,968, 6,858,394, 6,770,441, 6,429,027; and other synthesis techniques such as those disclosed in U.S. Pat. Nos. 5,807,522, 5,700,637 and 5,445,934 and US Appln No. 20040259146.

Arrays can be produced on a planar surface, or on a series of discrete surfaces, e.g. beads, that together form an array. The oligonucleotides used to create the peptide constructs can be produced using any single-stranded or double-stranded oligonucleotide array. Alternatively, oligonucleotide templates can be prepared individually and pooled, and smaller pools can be combined into larger pools.

In some embodiments, the oligonucleotides synthesized on the array comprise in addition to the unique peptide coding sequence, regions encoding an affinity tag and stop codon at one end of the oligonucleotide and a primer region at the other end of the oligonucleotide. Where single-stranded oligonucleotides are used in construction of the array, the single-stranded oligonucleotides may also comprise a region complementary to a primer that is used to synthesize a complementary strand for use in the in vitro transcription and translation reactions.

The non-coding region of the oligonucleotide preferably comprises a promoter region at the 5'-end of the oligonucleotide followed by a ribosomal binding site (RBS), used to initiate the transcription and translation events to produce the peptide constructs. The non-coding region can be included in the array-synthesized oligonucleotide, or it can be attached using various techniques such as ligation.

In yet another embodiment, the oligonucleotides that are used to transcribe the RNA may be created as the result of multiple ligation events to increase the length of the oligonucleotide template to add additional features to the oligonucleotides and/or to increase the length of the peptide produced through in vitro transcription and translation. Ligation can be accomplished through the use of restriction enzyme digestion and ligation, or preferably by the use of splint ligation with splint oligonucleotides that are complementary to both the oligonucleotide associated with the array (having the coding region) and the oligonucleotide that is to be added to the array (having promoter regions and/or additional coding regions). For example, a promoter region can be added to all of the oligonucleotides on an array using splint ligation. Alternatively, different promoter regions can be added to different coding oligonucleotides (e.g., a subset of the coding oligonucleotides) to, e.g., allow for selective hybridization of splint oligonucleotides (and thus selective ligations) as a means to introduce additional sequence variation, facilitate separation at a later step and/or otherwise identify the peptide constructs from one another. Typically, promoter oligonucleotides will be the same or substantially similar for all peptide constructs in a set.

Additionally, a combination of array-based synthesis and ligation techniques may be used to create specific types of peptides for interrogation. For example, many proteins have various alternatively-spliced isoforms that vary only in the domains at the C-terminus or N-terminus, and the coding oligonucleotides can have the variable regions of these proteins synthesized directly on the array surface and the common domains of the proteins added to the array-based oligonucleotides via ligation. In a specific example, there are at least 27 alternatively-spliced Neural Cell Adhesion Molecule (NCAM) mRNAs produced, and the three main isoforms of NCAM vary only in their cytoplasmic domain. Thus, the ability to create longer oligonucleotide templates to use as templates for transcription and translation can provide tools to better elucidate the activity and protein interaction of the various forms of proteins, and give insight into regulation, e.g., for therapeutic development. Numerous other such uses of constructed regions having certain constant domains, e.g., the N-terminus, the C-terminus, active binding sites, enzymatic active regions, etc. are envisioned with the peptide constructs.

The design of the surface-immobilized oligonucleotides and ligation oligonucleotides—in particular for determination of appropriate primer, restriction site(s), ligation and/or sequences useful for amplification or isolation—may optionally utilize probe design algorithms, including but not limited to those algorithms described in Rouillard, et al., Nucleic Acid Res., 31(12):3057-62 (2003).

Returning to FIG. 2, upon ligation (step 206) of the promoter and coding oligonucleotides, the oligonucleotide on the array surface 215 comprises from 5' to 3': promoter sequence 207 comprising T7 promoter region, and ribosomal binding site (RBS), universal sequence 203, coding region 201 and universal sequence 205. In addition, the promoter oligonucleotide may comprise a sequence coding for a common peptide tag that will be positioned at the N-terminus of the peptides. The N-terminal peptide tag may be used to separate or purify the peptide constructs, to cleave the peptide constructs, and the like. Universal primer 217, which is complementary to universal sequence 205, is extended in step 208 by, e.g., primer extension using DNA polymerase to produce a double-stranded oligonucleotide 219 attached to array surface 215.

Single-stranded oligonucleotides 221 are eluted at step 214 from the array by denaturing double-stranded oligonucleotides 219. The eluted single-stranded oligonucleotides 221 are amplified by PCR at step 216 to make double-stranded oligonucleotides 223, and the resulting double-stranded oligonucleotides 223 are transcribed at step 218 into corresponding RNA templates 225 by T7 RNA polymerase. The RNA templates are then used in later steps to translate the peptides. In an alternative embodiment, the RNA templates are transcribed directly from the double-stranded oligonucleotides attached to the array surface. In this embodiment, elution step 214 is not performed. In vitro transcription is performed using techniques well known to those in the art. Examples of such methods include those disclosed in, e.g., Krieg, et al., Nucleic Acids Research 12:7057-7070 (1984); and Craig, et al., Nucleic Acids Research 20:4987-4995 (1992).

As described, in yet other embodiments the entire template can be created by synthesis, e.g., on an array, provided high fidelity synthesis is achieved. This alternative embodiment is illustrated in path B of FIG. 2, where the entire oligonucleotide to be transcribed is synthesized on a microarray su. The oligonucleotide to be transcribed shown in path B comprises the same functional regions as the oligonucleotide produced in path A: promoter region 207 comprising promoter region, RBS, and an optional N-terminal peptide tag region, universal sequence 203, coding region 201 and universal sequence 205. As in path A, a universal primer 217 is hybridized in step 210 to the oligonucleotides on the array and extended at step 212 using DNA polymerase to create double-stranded oligonucleotides 219. Single-stranded oligonucleotides 221 are eluted at step 214 and the eluted single-stranded oligonucleotides 221 are amplified by PCR to make double-stranded oligonucleotide transcription templates 223. The double-stranded oligonucleotide transcription templates 223 are transcribed at step 218 into RNAs by, e.g., T7 RNA polymerase.

In some aspects of the invention, linkers may be used to attach the oligonucleotides to the array surface. Numerous types of linkers can be used, and the linker will be selected based on the desired properties of the linker (length, flexibility) and other characteristics. Such linkers may comprise nucleotides, polypeptides, or a suitable synthetic material. In certain aspects, the oligonucleotides on the array may comprise a cleavable linker directly attached to the array substrate that allows the oligonucleotides to be separated from the substrate. In some aspects, the cleavable linker will be the same or identical for all of the oligonucleotides. In other aspects, certain subsets of oligonucleotides on the array substrate will have the same cleavable linker, where this cleavable linker differs from the cleavable linkers used with the other subsets of oligonucleotides on the same substrate surface. This allows certain constructs to be separated from the substrate when others are not. In some embodiments, using cleavable linkers, double-stranded oligonucleotides do not need to be denatured to release the oligonucleotides into solution for amplification; instead, the oligonucleotides can be cleaved from the surface of the array either before or after synthesis of the second strand of the oligonucleotide.

In an alternative approach to using synthesized oligonucleotides to generate templates, fragmented genomic DNA may be used to generate transcription templates. Genomic DNA can be fragmented by any number of methods, including sonication, nebulization, nuclease cleavage, or a combination of these methods. Fragmentation leads to the generation of DNA fragments, where fragments of a preferred size may be selected. DNA adaptors are then ligated to both ends of the DNA fragments. The DNA adaptor ligated to the 5' end typically comprises a promoter, e.g., a T7 promoter, and a ribosome binding site, although other sequences may be present as well, including sequences that code for peptide tags. The 3' adaptor preferably comprises a region to allow binding of a primer so that PCR amplification can be performed, as well as a region engineered for ligation, e.g., a region complementary to a region in a splint ligation oligonucleotide. As with the 5' DNA adaptor, the 3' adaptor may comprise other sequences, including sequences that code for peptide tags.

In Vitro Translation and Peptide Construct Formation—Scheme I

In one embodiment of the invention, the RNA transcripts produced as illustrated in FIG. 2 are used to generate the peptide constructs via a C-terminus binding moiety and ribosome-mediated coupling of the mRNA and the translated peptide. As discussed in FIG. 2, the oligonucleotides used to generate the RNA transcripts comprise a promoter region, a ribosome binding site (RBS) to enable translation, and an optional sequence coding for an N-terminal common peptide (for example, a TEV protease site for labeling as described in Tolbert and Wong, Agnew. Chem. Int. Ed., 41(12):2171-74 (2001)) at the 5'-end of the peptide coding sequence. In addition, the coding region of the ligated oligonucleotide may comprise one or more optional sequences such as a sequence coding for a C-terminal common peptide tag (for example, an affinity tag for purification), as well as a sequence available for ligation of an adaptor moiety at the 3'-end.

Figure 3:
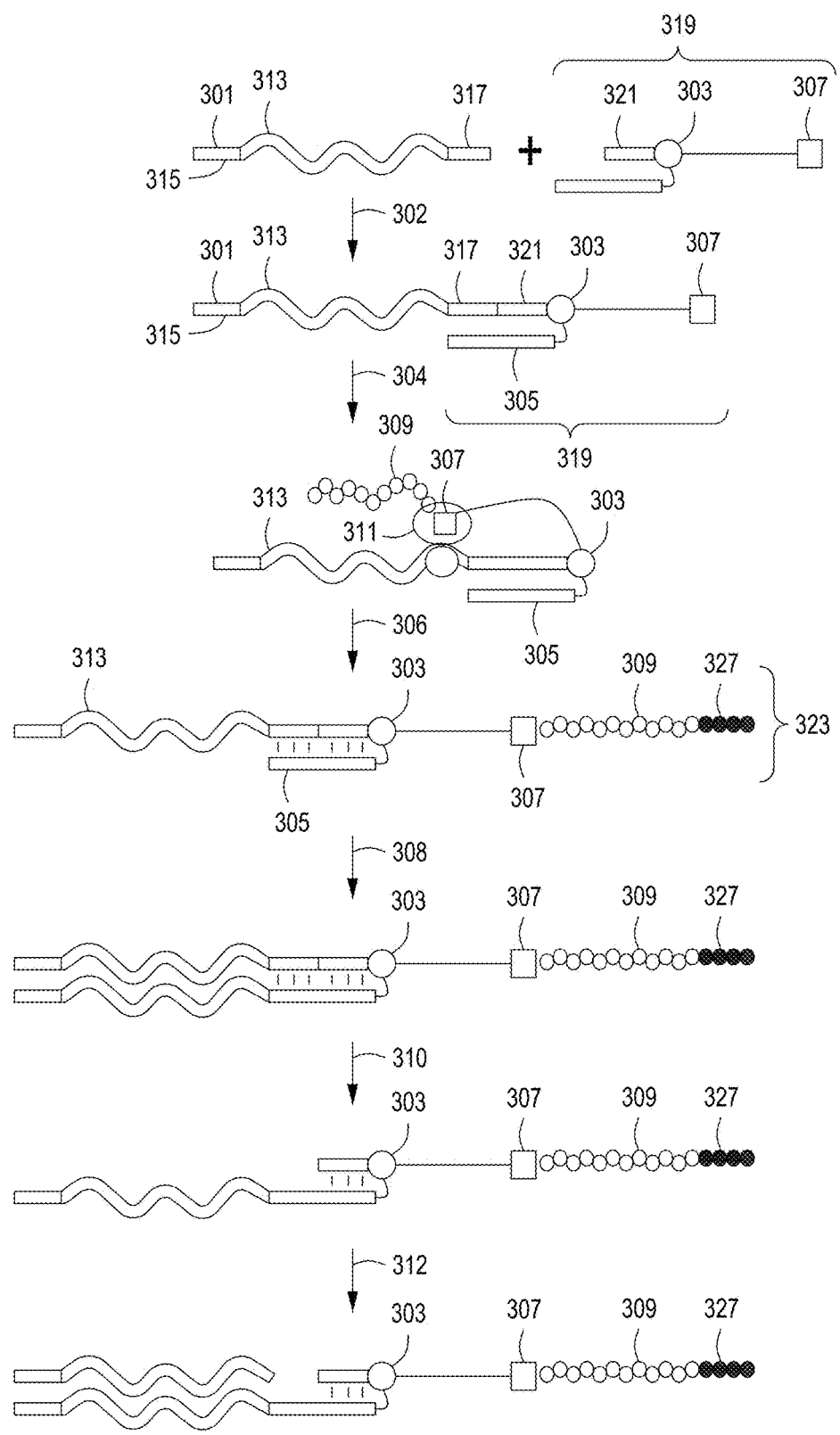
FIG. 3 illustrates an exemplary method for synthesizing the peptide constructs of the invention using the RNAs produced as illustrated in FIG. 2.

One embodiment is illustrated in FIG. 3. RNA transcript 301 comprises RBS 315, coding region 313 and a region 317 complementary to a portion of a first nucleotide region 305 of an adaptor moiety 319. At step 302, adaptor moiety 319 comprising a C-terminus binding moiety 307 and a first nucleotide region 305 attached to a second nucleotide region 321 via a linker moiety 303 is attached to the 3'-end of the RNA transcript 301 via template-directed ligation (see, e.g., U.S. Pat. No. 6,416,950 to Lohse and Kurz, et al., Chembiochem, 2:666-672 (2001), both of which are incorporated herein in their entirety). The C-terminus binding moiety 307 in preferred embodiments is puromycin, but other C-terminus binding moieties may be employed. The linker moiety 303 in preferred embodiments is a furocoumarin such as psoralen. Other members of this family include, but are not limited to, angelicin, isomers of psoralen, and derivatives of psoralen or angelicin. Common derivatives are imperatorin, xanthotoxin, bergapten and nodekenetin. The entire structure of the adaptor moiety can be made by chemical synthesis using a branching phosphoramidite. The linker 303 can also be a nucleotide in situations when the construct 309 is made as a branched DNA molecule.

During in vitro translation 304, ribosome 311 stalls when it reaches the DNA of first nucleotide region 305 of adaptor moiety 319 at the 3'-end of the mRNA 301. Stalling of ribosome 311 allows the puromycin residue 307 to enter the A-site of ribosome 311 and attach to the C-terminus of the translated peptide 309. The ribosome 311 then disassociates from the mRNA-peptide construct at step 306, resulting in the peptide construct shown at 323. At step 308, the mRNA portion of the peptide constructs is replaced by the corresponding cDNA through production of a cDNA-mRNA hybrid molecule via reverse transcription (see, e.g., U.S. Pat. No. 6,416,950 and Kurz, et al. supra). Next, optional treatment of the peptide constructs with, e.g., RNase H in step 310 degrades the RNA component of the peptide construct. Optionally, the single-stranded cDNA can be converted to double-stranded cDNA (the cDNA will be the identifying nucleic acid in a later sequencing step) by primer annealing and extension with DNA polymerase in step 312. Optionally, the newly-synthesized cDNA strand can be covalently attached to the adaptor moiety by ligation.

In addition to the features described thus far, the adaptor moiety may comprise other features that, e.g., enhance translation of the peptides and production of the peptide constructs. For example, nucleotide linker regions and/or other spacers may be incorporated along with the C-terminus binding moiety (e.g., puromycin) to provide flexibility of the adaptor moiety and an appropriate length for the puromycin sterically to be able enter the A site of the ribosome. Thus, in a preferred aspect, a linker portion is added to the adaptor moiety to provide flexibility and length, enabling the efficient production of high-quality, full-length mRNA labeled peptide constructs. In a specific example, the adaptor moiety comprises the following structure: $p(dA)_{10}$-$(C18)_5$-dCdC-Pu, where C18 is a polyethylene glycol (PEG) linker, and the PU is a puromycin residue. Five C18 linkers were found to result in a more flexible adaptor moiety and allowed for improved peptide construct yields. The 3'-puromycin oligonucleotide spacer has been found useful for the production of peptide constructs; similarly, $dA_{25}$ in combination with a Spacer 9 (Glen Research, Sterling, Va.) and dAdCdCP at the 5' terminus worked well to produce peptide constructs. In general, adaptor moieties longer than 40 nucleotides and shorter than 16 nucleotides showed greatly-reduced efficiency of peptide construct formation (see, e.g., Huang and Liu, Biochemistry, 46(35):10102-12 (2007), Epub 2007 Aug. 9).

Due to the stable nature of the peptide constructs, in certain assay systems the sets of peptide constructs may be utilized two or more times. The covalent linkage of the peptide to the cDNA (identifying nucleic acid) via the linker moiety (e.g., psoralen of the adaptor moiety) is a much stronger bond than that seen in transient protein-protein interactions, and thus many proteins and compounds used to interrogate the peptide constructs can be effectively removed or stripped to allow the constructs to be used in other interrogations.

In Vitro Translation and Peptide Construct Formation—Scheme II

Figure 4:
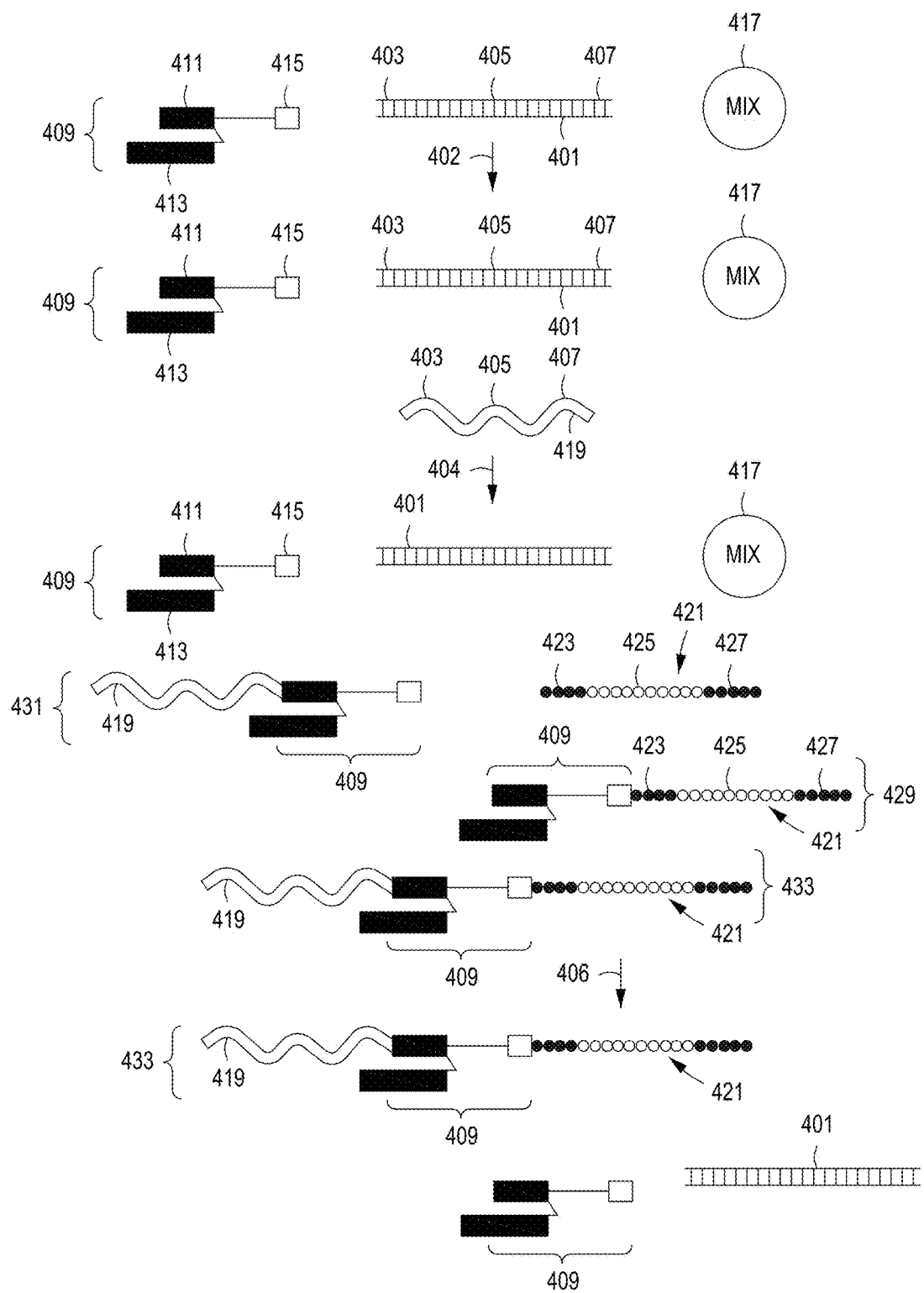
FIG. 4 illustrates an alternative exemplary method for synthesizing the peptide constructs of the invention.

In addition to the Scheme I ribosome-mediated formation of peptide constructs, peptide constructs may be formed in a "one-pot" reaction combining a number of biochemical reactions adapted to be carried out in the same reaction volume. FIG. 4 illustrates an exemplary method for the "one-pot", Scheme II approach. In preferred embodiments of the "one-pot" Scheme II, the order of reactions is relatively undefined. RNA must first be produced for the other reactions to take place, but once RNA is made it can be translated, or ligation of the adaptor can occur as the next step. Similarly, once the peptide is produced via in vitro translation, attachment via the capture moiety can occur to free adaptor followed by ligation, or to an adaptor that is already ligated to RNA.

FIG. 4 shows a DNA molecule 401, with a region 403 comprising a promoter and a ribosomal binding site, and, optionally, a sequence coding for an N-terminal tag. DNA 401 also comprises a coding or variable region 405 and a region 407 that codes for an amino acid capture tag sequence that is a substrate for a peptide modifying enzyme, e.g., SFP synthase (see, e.g., Zhou et al., ACS Chemical Biology, 2(5):337-46 (2007)). In addition to DNA 401, an adaptor 409, comprising first nucleic acid ligation region 411, second nucleic acid ligation region 413, and a capture moiety 415 is present, along with a reaction mix 417. Reaction mix 417 comprises the reagents for the biochemical reactions that take place in the 'one pot', including an RNA polymerase such as T7 RNA polymerase; nucleotides and cofactors to enable transcription of the DNA template; ribosomes, amino acids and cofactors to enable translation of the mRNA; a ligase (e.g. T4 DNA ligase); cofactors and a splint sequence to enable the ligation of the adaptor to the RNA; and an enzyme that catalyzes the attachment of the capture tag on the translated peptide to the capture moiety of the adaptor. In preferred embodiments, the capture moiety 415 is coenzyme A, the amino acid capture tag is a C-terminal S6 tag, and the enzyme that catalyzes the attachment of the S6 capture tag to the coenzyme A capture moiety is SFP synthase.

As the reaction in the 'one pot' progresses at step 402, in addition to DNA template 401, adaptor 409 and reaction mix 417, mRNA 419 that is being transcribed from the DNA template 401 is present in the mix. mRNA comprises region 403 comprising the ribosomal binding site, the coding region 405 and region 407 that codes for the amino acid capture tag sequence. As the reaction progresses further at step 404, in addition to DNA template 401, adaptor 409, reaction mix 417, and mRNA 419, peptide 421 that is translated from the mRNA is present in the mix. Peptide 421 is shown with three regions: amino acid capture tag 423, peptide sequence to be interrogated 425 and optional N-terminal tag region 427. Also being generated in the mix are mRNA 419 ligated to adaptor 409 via the via the nucleic acid regions 411 and 413 of adaptor 409 (this intermediary construct is shown at 431) (note that adaptor 409 is preferably ligated to the 3' end of the mRNA, but the adaptor 409 could be ligated to either end); peptide 421 attached via amino acid capture tag 423 to adaptor 409 via capture moiety 415 (this intermediary construct is shown at 429); and a peptide construct 433, comprising peptide 421, adaptor 409 and mRNA 419. Finally, as the "one-pot" reaction nears completion, peptide construct 433 is present in abundance. Subsequent to the completion of the "one-pot" reaction, the peptide constructs from many such reactions can be pooled together to form a complete set of peptide constructs. At this point, the RNA portion of the peptide constructs can be replaced by the corresponding cDNA through production of a cDNA-RNA hybrid via reverse transcription and RNase digestion of the RNA strand, as was described in Scheme I.

Note that in the Scheme II "one-pot" reaction—as opposed to the Scheme I embodiment—it is possible, if desired, to couple the peptide formed by the in vitro translation reaction with nucleotide sequences different than those that code for the peptide. With the Scheme II "one-pot" method, the peptide can be conjugated to any suitable nucleic acid that is present, e.g. via engineering of the first and second nucleic acid ligation sequences on the adaptor and of the identifying nucleic acid sequence. In most embodiments, the preferred nucleic acid sequence will be the encoding sequence. However, in other embodiments it is possible to use a variety of designs where a first sequence is used to encode the synthesized peptide and a second, distinct sequence is subsequently attached to the protein in order to, e.g., identify the peptide, or to manipulate it for further reactions.

One preferred aspect of the "one-pot" embodiment is use of phosphopantetheinyl transferase-catalyzed site-specific attachment of the co-enzyme A (CoA) portion of the adaptor (CoA as the capture moiety) to a serine residue engineered as part of a capture tag composing a portion of the translated peptide. (See, e.g., U.S. Pat. No. 7,192,735 to Lambalot, et al.; U.S. Pat. No. 7,666,612 to Johnsson, et al.; U.S. Pub. No. 2006/0216775 to Burkart, et al.; WO 2007/041689 to Walsh, et al.; Waichman, et al., Anal. Chem., 82:1478-85 (2010);

Wong, et al., J. Am. Chem. Soc., 130:12456-64 (2008); and Yin, et al., PNAS, 102(44):15815-20 (2005), all of which are incorporated by reference in their entirety herein.) In some embodiments, the phosphopantetheinyl transferase is SFP synthase, though other related PPTases may be employed. Also, in some embodiments the serine residue, engineered as part of the translated peptide, is present in the context of an S6 tag sequence; however, other sequences may be employed, including ybbR tags (see, e.g., Yin, et al., PNAS, 102(44):15815-20 (2005). Also, in alternative embodiments, other enzymatic or chemical reactions may be used to link the C- or N-terminal tag on the peptides.

While Scheme I is intrinsically parallel with many peptide constructs being formed in the same reaction volume, Scheme II is parallelized by concurrent processing of many, separate reaction volumes. Concurrent processing of many, separate reaction volumes may be accomplished by emulsion reactions, emulsion in combination with beads or in a microwell, microdroplet or microarray format such as the one described in Example, 6. Some degree of multiplexing of the "one-pot" reaction is possible within each reaction volume; that is, two or more proteins could be produced and tagged with different identifiers by using orthogonal sets of capture tags/capture moities.

Another difference between Scheme I and Scheme II is that in the Scheme II embodiments described, only fully translated peptides are coupled with the nucleic acids, as the S6 residue is on the C-terminus, whereas in Scheme I, peptide synthesis could be terminated at any amino acid position.

Exemplary Assays and Analyses

The peptide constructs of the invention can be utilized to analyze peptide sequences, testing virtually any activity that is mediated by a protein or requires a protein interaction. For example, a library of peptide constructs representing the human proteome can be used to screen for the presence of antibodies such as autoantibodies or antibodies associated with cancers in human sera. Such a comprehensive screen is beyond the capability of conventional assay systems. Similarly, a library of peptide constructs representing the proteomes or partial proteomes of diverse pathogens can be used to detect and estimate the abundance of antibodies reactive to pathogens in human sera. Further, assays utilizing the peptide constructs of the present invention can be used to identify epitope binding sites, as well as to identify preferred binding sites; to identify kinase phosphorylation sites, as well as to identify preferred phosphorylation sites; and to identify peptides that are substrates for proteases, as well as to analyze protease activity. To exemplify the potential applications of the invention, example assays are described in more detail below.

It is a distinct advantage of the invention that the individual peptides present in the peptide constructs of the invention can be detected through detection of the identifying nucleic acid, e.g., by sequencing the identifying nucleic acid (typically cDNA) associated with the peptide of interest in any particular peptide construct. The ability to identify the peptides in the peptide constructs of the invention by sequencing the identifying nucleic acids allows for very high throughput screening of the peptides using the cost effective mechanisms of sequencing, and is far more sensitive and scalable than direct peptide detection.

In one exemplary assay, the peptide constructs of the invention are used to test for protease activity. Generally, the peptide constructs used for determination of protease activity comprise identifying nucleic acids (cDNA or RNA molecules) attached to the C-terminus of the peptides of interest, with an affinity group (for example, a peptide capture tag or a biotin residue) attached at the N-terminus. When the peptide constructs are treated with a protease, peptides that are substrates for the protease will be cleaved and will lose the affinity group at the N-terminus. Therefore, only uncleaved peptides are captured with a capture moiety capable of binding to the N-terminal affinity tag. Employing such an affinity tag and capture moiety allows the peptide constructs having cleaved peptides to be separated from those with non-cleaved peptides. The identifying nucleic acids attached to the cleaved peptides are isolated and sequenced using highly-parallel, next-generation DNA sequencing. Alternatively, the nucleic acids with uncleaved peptides could be isolated and sequenced, though in some assays this would require many more constructs to be sequenced so in these cases it would be less preferred.

Figure 5:
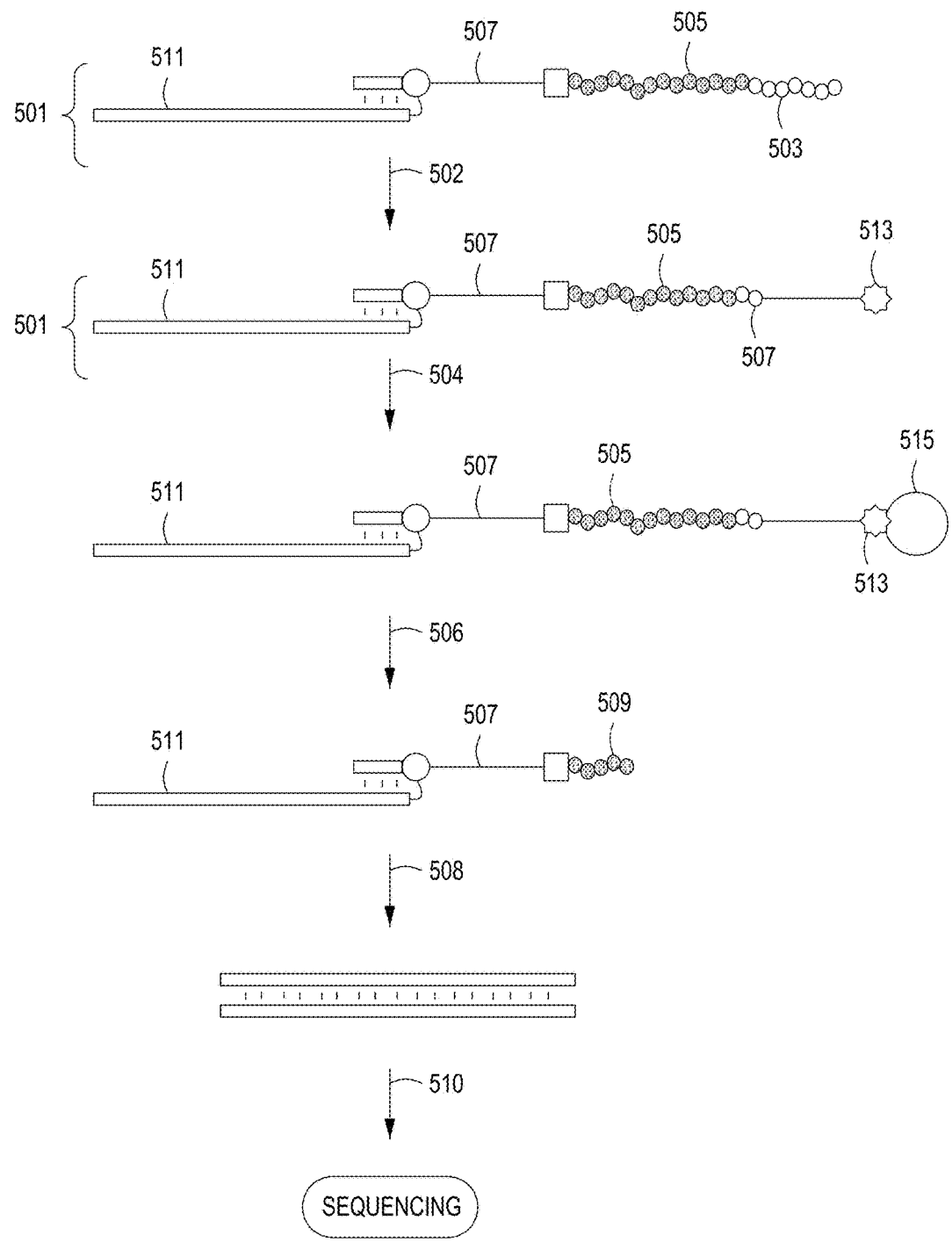
FIG. 5 illustrates an exemplary protease assay using the peptide constructs of the invention.

One embodiment of an exemplary protease assay is illustrated in FIG. 5. In this assay system, a pool of peptide constructs is synthesized, for example, by methods as shown in FIGS. 3 and/or 4. Each peptide construct 501 comprises a cDNA identifier 511 linked to a peptide comprising a test peptide 505 (the variable portion of the translated peptide), and a peptide sequence 503 that is a substrate for TEV protease, (namely, ENLYFQCA (SEQ ID NO:7)). Upon TEV protease cleavage at step 502, peptide sequence 503 is cleaved leaving an N-terminal cysteine-alanine (CA) 507 on each peptide construct. The N-terminal cysteine residue 507 is then modified with an affinity tag to allow capture on a solid support. In one preferred embodiment this is achieved using native chemical ligation by molecules containing thioesters, such as biotin-PEG-thioesters 513 (described in, e.g., Tolbert and Wong, Angew. Chem. Int. Ed., 41(12): 2171-73 (2002)). The biotinylated peptides can be captured at step 504 using streptavidin-coated magnetic beads 515. At step 506, the captured peptide constructs are treated with a solution containing a protease of interest. Peptide constructs having peptides that are suitable substrates for the protease are cleaved and released from the streptavidin-coated magnetic beads. Alternatively, the protease cleavage reaction can be performed in solution before capture by the beads, followed by capture of uncleaved peptide constructs on magnetic beads. In either case, the uncleaved peptide constructs are immobilized on the beads and cleaved peptide constructs are released, facilitating separation of the two populations.

Numerous binding pairs can be used to separate reacted (transformed or modified) peptide constructs from unreacted (untransformed or unmodified) peptide constructs in the assays of the present invention. These include but are not limited to, streptavidin and short streptavidin binding peptides such as StrepTag (Schmidt, et al., J. Mol. Bio., 255: 753-66 (1996); Schmidt and Skerra, J. Chromatog. A., 676:337-345 (1994); Skerra and Schmidt, Meth. in Enz., 326:271-304 (2000)), StrepTag II (Schmidt and Skerra, Nat. Protoc., 2:1528-35 (2007); Voss and Skerra, Protein Eng., 10(8):975-82 (1997)), and HPQ motifs (Gissel et al., J. of Peptide Science 1(4):217-226 (1995); Helms et al., JBC, 282(13):9813-24 (2007)); oligo histidine peptide tags and His6 binding groups (Kneusel et al., Procedures for the Analysis and Purification of His-tagged Proteins, in *Nucleic Acid Protocols Handbook*, p. 921 (2000) (Humana Press); Smith et al., Gene, 67:31-40 (1988)); FLAG peptide tags and His6 or His5 peptide groups (see, e.g., Kozlov, Combinatorial Chem. And High Throughput Screening, 11:24-35 (2008)); biotin and streptavidin, biotin and avidin, antibody-antigen pairs, and the like. Additionally, selective covalent linkage of peptide constructs to solid supports is possible.

For example, N-terminal cysteine residues of cleaved peptides can be covalently coupled to thioester modified solid surfaces.

Alternatively, a chemically-reactive species (e.g., an aldehyde tag), label or other binding agent may be added in the construction of the peptide constructs. For example, introduction of a sulfatase consensus sequence recognized by the formylglycine-generating enzyme results in site-specific introduction of aldehyde groups into the peptide constructs. This consensus sequence can be between 6-13 amino acids, and the smallest such "aldehyde tags" are no larger than a His6 tag. Enzymatic modification at a sulfatase motif by formylglycine generating enzyme (FGE) generates a formylglycine (fGly) residue, which allows site-specific attachment of a capture agent or other moiety of interest to the peptide by covalent capture on hydrazine- or oxime-labeled oligo templates. This modification is reversible, and thus the introduction of this tag into the peptide constructs allows aldehyde-tagged peptides to be reversibly modified with multiple epitopes. Examples of aldehyde tags for use in the present invention are described in, e.g., US2008/0187956; Dierks and Frese, Chem. BioChem., 10:425-427 (2009); Wu, et al., www.pnas.org_cgi_doi_10.1073_pnas.807820106; Rush and Bertozzi, J. Am. Chem. Soc., 9:130:37, (2008); Landgrebe et al., Gene, 316: 47-56 (2003); Carrico, Nat. Chem. Biology, 3:6 (2007), each of which is incorporated by reference in its entirety for teaching useful tags and their use in peptide modification. Additionally, N-terminal formyl-methionine that is generated during translation initiation on all peptides can be specifically cleaved from peptides to expose the N-terminal cysteine. Two enzymes are required to remove formyl-methionine: peptide deformylase and methionine aminopeptidase. The resulting N-terminal cysteine residue can be used for peptide modification with an affinity residue (e.g., a biotin residue) or for direct immobilization on solid surfaces.

Returning to FIG. 5, the identifying nucleic acids (in this example, cDNAs) are then used as templates for amplification at step 508, with sequencing adaptors added during amplification. The amplified identifying nucleic acids are then sequenced at step 510, preferably using a next-generation DNA sequencing instrument. The sequence information obtained from sequencing the identifying nucleic acids (a) identifies which peptides were cleaved by the protease, and (b) provides information regarding the relative abundance of the cleaved peptides.

Various methods of sequence identification or determination can be used with the methods of the inventions. Sequencing methods that enable the parallel yet separate determination of sequences of many individual template molecules in the population are preferred. Such so-called 'next-generation' sequencing technologies are digital in nature, generating sequences that are based on single molecules (or clones thereof). The advantage of a digital sequence readout for the assays or analyses of the present invention is that a large number of peptide constructs can be analyzed simultaneously in a single assay, and a quantitative measure of the frequency of each peptide can be obtained based on the frequency the sequence of the identifying nucleic acid appears in the readout. In some methods of the invention, the sequence of at least fifty thousand identifying nucleic acids are determined in parallel, in other methods the sequence of at least one hundred thousand identifying nucleic acids are determined in parallel, in some methods the sequence of at least five hundred thousand identifying nucleic acids are determined in parallel, and in some methods the sequence of at least one million, ten million, one hundred million, one billion, ten billion, one hundred billion or more identifying nucleic acids are determined in parallel.

Exemplary methods for sequence identification or determination include, but are not limited to, hybridization-based methods, such as disclosed in e.g., Drmanac, U.S. Pat. Nos. 6,864,052; 6,309,824; and 6,401,267; and Drmanac et al, U.S. patent publication 2005/0191656; sequencing-by-synthesis methods, e.g., U.S. Pat. Nos. 6,210,891; 6,828,100; 6,969,488; 6,897,023; 6,833,246; 6,911,345; 6,787,308; 7,297,518; 7,462,449 and 7,501,245; US Publication Application Nos. 20110059436; 20040106110; 20030064398; and 20030022207; Ronaghi, et al, Science, 281: 363-365 (1998); and Li, et al, Proc. Natl. Acad. Sci., 100: 414-419 (2003); ligation-based methods, e.g., U.S. Pat. Nos. 5,912,148 and 6,130,073; and U.S. Pat. Appln Nos. 20100105052, 20070207482 and 20090018024; nanopore sequencing e.g., U.S. Pat. Appln Nos. 20070036511; 20080032301; 20080128627; 20090082212; and Soni and Meller, Clin Chem 53: 1996-2001 (2007)), as well as other methods, e.g., U.S. Pat. Appln Nos. 20110033854; 20090264299; 20090155781; and 20090005252; also, see, McKernan, et al., Genome Res., 19:1527-41 (2009) and Bentley, et al., Nature 456:53-59 (2008), all of which are incorporated herein in their entirety for all purposes.

In another exemplary assay, the peptide construct sets of the invention are used to test for the ability of certain peptides to undergo post-translational modifications. After a protein is synthesized, the posttranslational modifications of certain amino acids in the protein extends the range of functions of the protein by attaching other biochemical functional groups such as acetate, phosphate, lipid, or carbohydrate groups; by changing the chemical nature of an amino acid (e.g., citrullination); or by making structural changes, such as the formation of disulfide bridges. Also, enzymes may remove amino acids from the N-terminal end of the protein or cleave elsewhere in the peptide chain. For instance, the peptide hormone insulin is cut twice after disulfide bonds are formed, and a propeptide is removed from the middle of the chain; the resulting protein consists of two polypeptide chains connected by disulfide bonds. In another example, many proteases begin as zymogens that are then modified into an active form of the peptide via cleavage. Other modifications, like phosphorylation, are part of common mechanisms for controlling the behavior of a protein, such as activating or inactivating an enzyme.

Figure 6:
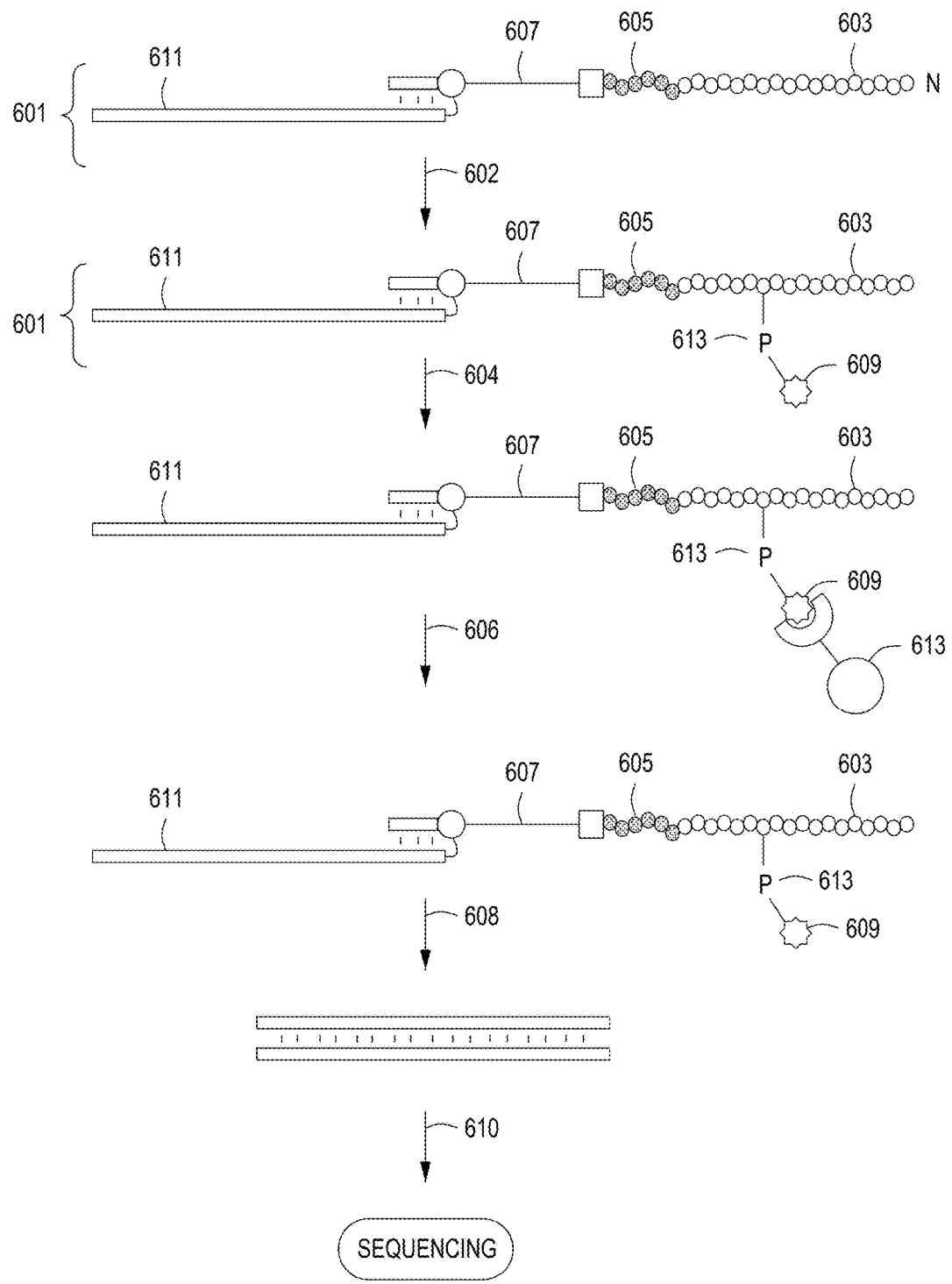
FIG. 6 illustrates an exemplary kinase assay using the peptide constructs of the invention.

In one specific example, the peptide construct sets of the invention are used to test for kinase activity. In this assay system, an example of which is illustrated in FIG. 6, a set of peptide constructs 601 comprising identifying nucleic acids (preferably c-DNA) 611 and test peptides 603 is synthesized as illustrated in FIG. 3 or 4. When the peptide construct set is treated at step 602 with a kinase enzyme, peptides that are substrates of the kinase will be phosphorylated (shown at 613).

The phosphate groups on the peptide constructs may then be labeled with an affinity molecule 609 (for example, a biotin residue) to enable capture of phosphorylated peptide constructs on a solid support 613, e.g. streptavidin coated magnetic beads, facilitating separation of phosphorylated and non-phosphorylated peptides (here, the phosphorylation and labeling are shown as one step). Alternatively, an affinity capture agent that recognizes the phosphorylated peptide directly, such as anti-phosphotyrosine antibody, can be used to capture the phosphorylated peptide. For example, biotinylated anti-phosphotyrosine antibodies can be immobilized on streptavidin coated magnetic beads and used to capture phosphorylated peptide constructs. Once the phosphorylated peptide constructs are captured on the beads, either directly or indirectly, they can be separated from non-phosphorylated peptide constructs. Once separated, the identifying nucleic acid portions of captured phosphorylated peptide constructs are used as templates for amplification at step 608, with sequencing adaptors added during amplification. The amplified identifying nucleic acids are sequenced at step 610 using, e.g., a next-generation DNA sequencing instrument. The sequence information obtained from sequencing the identifying nucleic acids (a) identifies which peptides were phosphorylated, and (b) the relative abundance of each phosphorylated peptide construct. Optionally, prior to amplification in step 608, the captured peptide constructs can be released into solution, e.g. using a competitive binder such as a phenyl phosphate solution or other competitive binder that has a chemical structure similar to a phosphorylated tyrosine residue. This can be used to increase the specificity of the assay by excluding peptide constructs non-specifically bound to the solid support.

In phosphorylation assays, many different methods can be used for labeling the phosphate groups, for example, modified ATP molecules that contain a biotin residue or other affinity group attached to a gamma-phosphate group or a chemically reactive group (e.g, a thiol group in gamma-ATP-thiophosphate). During the phosphorylation reaction, the biotin residue is transferred together with the gamma-phosphate group to the peptide substrate (see, e.g., Green et al, J. Am. Chem. Soc., 129(1):10-11 (2007); Wang, Anal. Chem., 77(17):5770-5774 (2005)). A second approach involves specific labeling of phosphate residues on peptides (see, e.g., Shults et al., ChemBioChem, 8:933-942 (2007); U.S. Pat. No. 7,803,751).

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric.

Example 1: Model System for Protease Substrate Generation and Screening

A model system was created to test the utility of the peptide constructs of the present invention in a protease assay. The model peptides used were GLVPRGSAG (SEQ ID NO:1), a target of commercially available thrombin (EMD Biosciences, San Diego, Calif.) and AGDDDDKAG (SEQ ID NO:2), a target of commercially available enterokinase (New England Biolabs, Ipswitch, Mass.). The protease recognition sites are shown in bold in the peptide sequences.

In addition to the peptide sequence of interest, peptide tags were chosen to be included in each peptide construct: Tag 1 at the N-terminus of all peptides, to be used in the protease substrate screening assay for peptide construct capture, and Tag 2 at the C-terminus as a tool to select for full-length peptides. FLAG (DYKDDDDK) (SEQ ID NO:3) and AU1 (DTYRYI) (SEQ ID NO:4) were analyzed for use as a C-terminal peptide Tag 2 for peptide construct purification. Inclusion of Tag 2 allowed properly expressed peptides to be affinity purified via antibody capture of the Tag 2 peptide. This is particularly useful because it rejects constructs with peptides truncated during translation, as well as constructs with peptides that have incorrect sequences because of a translational frame shift resulting from errors in DNA synthesis. In both cases, Tag 2 is not correctly displayed at the C-terminus and the peptides will not be captured by anti-Tag 2 antibody. A potential disadvantage of an extra C-terminal peptide sequence is that the tag itself can be a substrate for some proteases, thus affecting the assay (for example, the FLAG tag is a substrate for enterokinase). Therefore AGNASASA (SEQ ID NO:5) and GNASASA (SEQ ID NO:6) peptides were also used as C-terminal tags because they are less likely to be substrates for proteases.

Analysis of the sequence data generated from the assay can be used to identify and remove undesired sequences, i.e., those resulting from DNA templates with mutations. In this sense, an in silico purification can be carried out post-assay. This assumes Scheme I was used to prepare the peptide constructs, so that each peptide construct comprises a peptide and the particular mRNA used for translation or a cDNA copy of that message.

Figure 7:
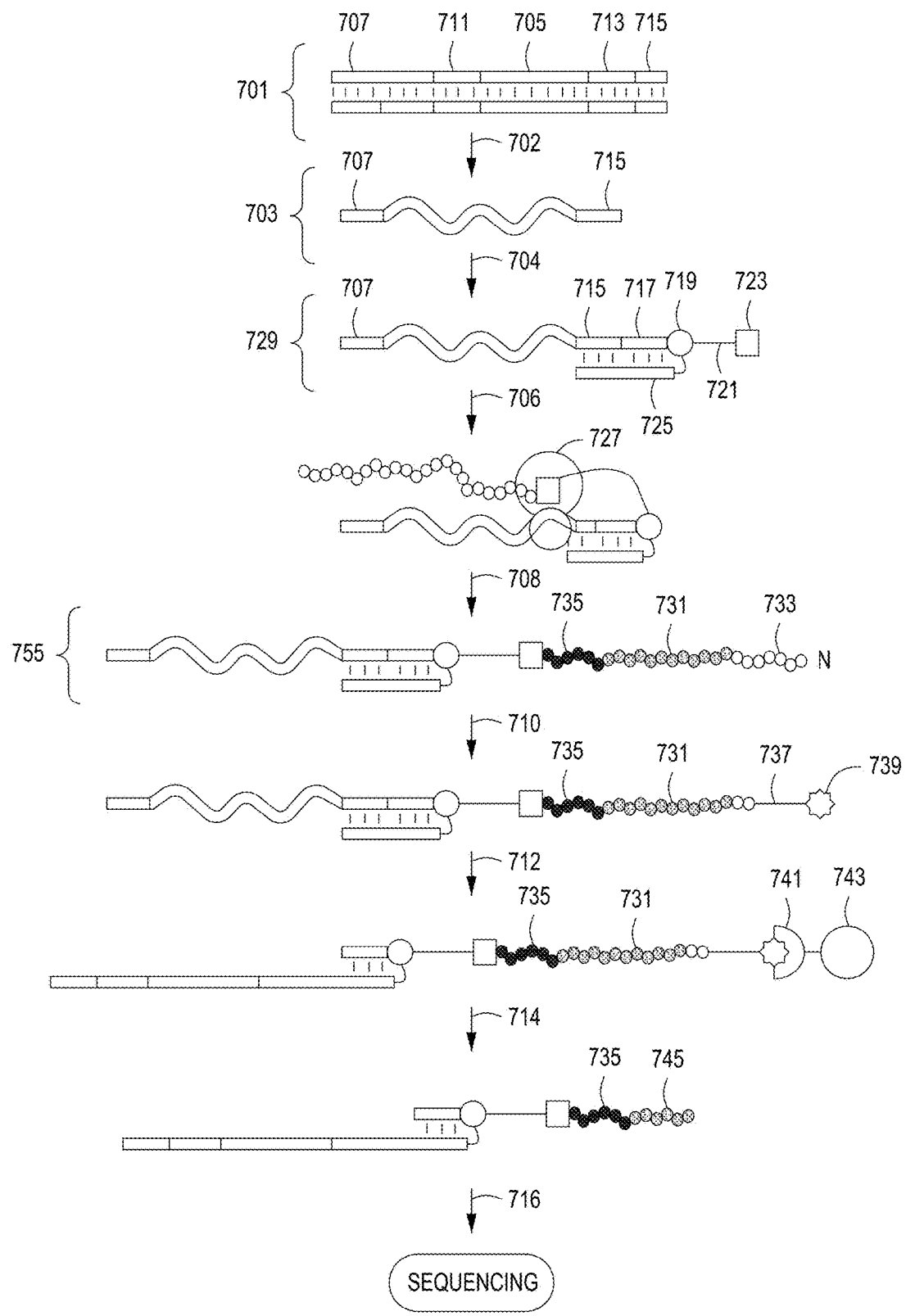
FIG. 7 illustrates embodiments for the production of constructs of the invention as described in detail in Example 1.

The preparation of the peptide construct sets for the protease assay is illustrated in FIG. 7. Briefly, a custom DNA oligonucleotide pool 701 encoding the peptides of a peptide construct set was custom synthesized on an array by conventional DNA synthesis. Following synthesis, oligonucleotides were deprotected and purified using standard techniques for oligo synthesis.

All DNA oligonucleotides 701 comprised a region 705 coding for the peptide sequences of interest (variable region) as well as common regions coding for a T7 promoter 707, a ribosomal binding site 709 (as described in He, et al., Methods Mol Biol., 484:193-205 (2008) and Tao, et al, Metab. Eng., 8(6):523-33 (2006)), N- and C-terminal peptide tags 711, 713, and a region 715 used for ligation of a DNA adaptor. The pool of oligonucleotides 701 was used to synthesize the corresponding pool of mRNAs 703 through in vitro transcription at step 702. Efficient in vitro transcription from the double-stranded oligonucleotides was performed using AmpliScribe T7-Flash (Epicentre Biotechnologies, Madison, Wis.), and the resulting RNA products were isolated by gel electrophoresis and purified using commercial kits (Qiagen, Valencia, Calif.).

An adaptor moiety was attached to the 3'-end of all RNAs via template-directed ligation (see, e.g., Kurz, et al., Chembiochem, 2(9):666-72 (2001)). The adaptor moiety consisted of DNAs 717, 725 that were cross-linked via a psoralen residue 719, as described in Pieles and Englisch, Nucleic Acids Res., 17(1):285-99 (1989), followed by gel-purification of the obtained product. The oligonucleotide 725 was made with a 5'-psoralen residue for crosslinking to oligo 717 using Psoralen C2 modifier (Glen Research). The adaptor moiety further comprised a long polyethylene glycol linker 721 attached at one end to the psoralen residue 719 and at the other end to a 3'-puromycin residue 723. The adaptor moiety was made as p(dA)8dTdA-(PEG)n-dCdC-Pu with a 5'-phosphate modification and a 3'-puromycin (Pu) residue using chemical phosphorylation and 3'-puromycin CPG reagents. A polyethylene glycol (PEG) linker 721 was introduced between oligonucleotide 717 and the 3'-puromycin residue 723 by coupling consecutive Spacer C9 or Spacer C18 modifiers (Glen Research). Next, the adaptor moiety was ligated to the 3'-end of RNA using template directed ligation with T4 DNA ligase as described earlier. A part of oligonucleotide 725 was complementary to the 3'-end of RNA 715 and served as a template for ligation.

An adaptor moiety was attached to the 3'-end of all RNAs via template-directed ligation (see, e.g., Kurz, et al., Chembiochem, 2(9):666-72 (2001). The adaptor moiety comprised two DNA segments 717 and 725, a long polyethylene glycol linker 721 bearing a 3'-puromycin residue 723, and a psoralen residue 719 linking the three. The oligonucleotide 725 was synthesized with a 5'-psoralen residue and cross-linked to oligo 717 as described in Pieles and Englisch, Nucleic Acids Res., 17(1):285-99 (1989), using Psoralen C2 modifier (Glen Research). The resulting product was gel-purified.

The RNA-adaptor moiety intermediates were subjected to in vitro translation at step 706, where a peptide comprising regions 733, 731 and 735 is synthesized. Ribosome 727 stalls when it reaches the DNA fragment at the 3'-end of the RNA template, allowing the puromycin residue 723 to enter the A-site of the ribosome and be incorporated into the C-terminus of the peptide forming the peptide construct. At step 708 the ribosome 727 disassociates from the newly-synthesized peptide, and the peptide construct 755 is released. Each peptide in the peptide construct set had a custom peptide region 731 and two peptide tags 733, 735: a FLAG peptide (DYADDDDK) (SEQ ID NO:3); AGNA-SASA (SEQ ID NO:5) or GNASASA (SEQ ID NO:6) at the C-terminus 735 and a modified TEV protease cleavage site (ENLYFQCA) (SEQ ID NO:7) at the N-terminus 733. The C-terminal FLAG tag 735 was used to purify correctly-translated, full-length peptides using anti-FLAG antibody-coated magnetic beads (step not shown). Note that although a Scheme I embodiment of peptide construct formation was employed in this Example, a Scheme II embodiment could have been employed as well.

A labeling molecule comprising a biotin residue 739 attached to a carbonyl thioester via a polyethylene glycol linker 737 was synthesized and attached in step 710 to the N-terminus of the peptides using a protocol similar to a native peptide ligation (see, e.g., Tolbert and Wong, Methods Mol. Biol., 283:255-66 (2004)). Briefly, the peptide constructs were treated with TEV protease to expose N-terminal cysteine residues, washed, and treated with 20 mM Biotin-PEG$_4$-Thioester precursor solution in 200 mM MPAA buffer, pH 7.0.

Following biotinylation, the peptide constructs were immobilized at step 712 on magnetic beads 743 coated with streptavidin molecules 741 and converted to cDNA-peptide constructs by reverse transcription followed by RNAse H-induced RNA degradation (see U.S. Pat. No. 6,416,950 and Kurz, et al. supra). The peptide constructs were treated at step 714 with a solution containing a protease of interest. Here HCV protease, furin, caspase-3, enterokinase and thrombin were each tested. The peptide constructs containing a cleavage site for proteases were cleaved (resulting in a protease cleavage fragments 745), and thereby released from the beads into solution. The non-cleaved peptide constructs were separated from the cleaved peptide constructs by removal of the magnetic beads 743. The identifying nucleic acids associated with the cleaved peptide constructs were sequenced using a next-generation DNA sequencing instrument. Alternatively, the protease cleavage can be carried out prior to immobilizing the peptide constructs, and protease cleavage products identified by capturing uncleaved peptide constructs on magnetic beads after the cleavage reaction and sequencing DNA from the solution containing cleaved peptide constructs (not shown).

In order to improve the efficiency of synthesis of the peptide constructs, the design of the adaptor moiety was optimized. Such optimization resulted in a several-fold increase in efficiency of conversion of the RNA-adaptor moiety intermediates into RNA-peptide conjugates over published methods. The efficiency of conversion was checked by gel-electrophoresis, where RNA-adaptor constructs with various PEG linker lengths were tested for efficiency of production of the peptide constructs. Favorable efficiency was observed for an adaptor with a polyethylene glycol linker consisting of five C18 modifiers while control constructs comprising $(dA)_{27}dCdC$-Pu and $(dA)_{21}(C9)_3$CdC-Pu produced constructs less efficiently.

Peptide constructs were analyzed by denaturing polyacrylamide gel electrophoresis (PAGE) to check for the efficiency of biotinylation at their N-termini and to check the efficiency of cleavage of a biotinylation peptide treated with an appropriate protease. The result demonstrated excellent efficiency both of the biotinylation reaction and of the cleavage reaction of the protease on the appropriate peptide substrate.

Figure 8:
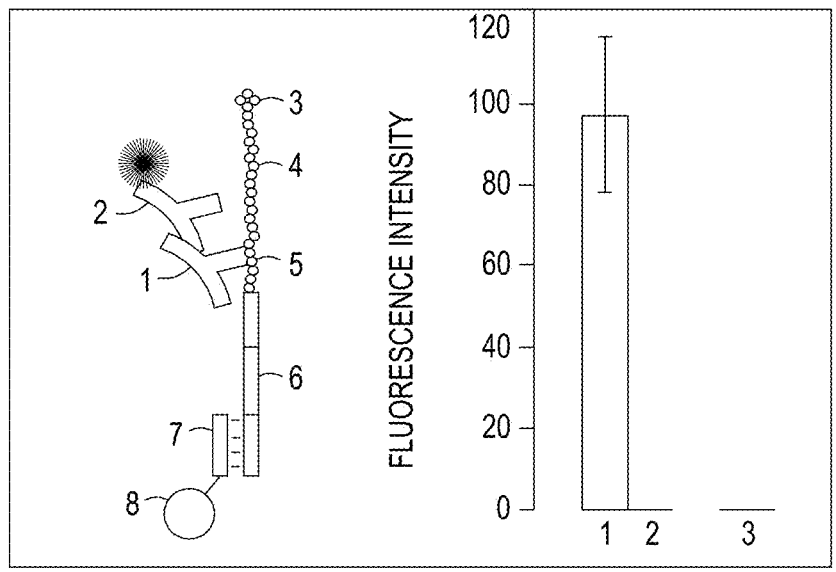
FIGS. 8A and 8B illustrate the efficiency of transcription and the efficiency and specificity of the protease cleavage, respectively, using the methods and constructs of FIG. 7.
Figure 8:
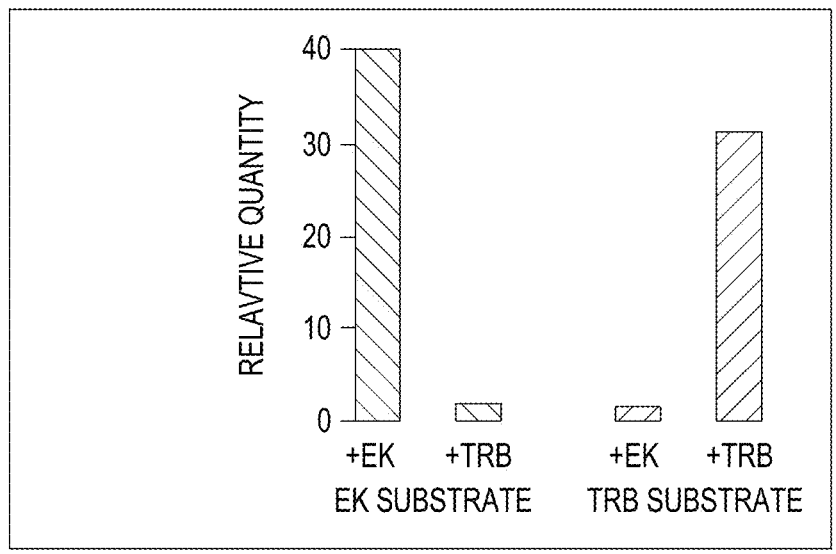

Translation efficiency also was determined and the results are shown in FIG. 8A. The presence of fully translated peptides in the peptide constructs was confirmed by detection of the C-terminal tag (5) by specific antibodies (1) and (2). Peptide constructs were captured using beads (8) with immobilized DNA (7) complementary to a common region (6) of the oligonucleotide portion of the peptide constructs. The beads were imaged using a DM6000B automated fluorescence microscope and imaging system (Leica). Bar 1 on the plot represents in vitro translation in the presence of Pu-modified template coding for a peptide of interest, bar 2 is in vitro translation without template, bar 3 is Pu-modified template without in vitro translation.

The results of the protease assay were verified by gel electrophoresis. Individual peptide constructs were cleaved by proteases and the reaction products were analyzed by PAGE. When treated with enterokinase, the peptide construct comprising the enterokinase substrate was cleaved; however, neither the control nor the peptide construct comprising the thrombin substrate were cleaved. Similarly, then treated with thrombin, the peptide construct comprising the thrombin substrate was cleaved; however neither the control nor the peptide construct comprising the enterokinase substrate was cleaved. FIG. 8B is a bar plot representing qPCR quantification of the cleaved peptide constructs in a representative protease assay. Peptide construct comprising substrates for enterokinase or thrombin were each treated with either enterokinase or thrombin. The cleaved peptide constructs were separated from the uncleaved, and the identifying RNA portion of the peptide conjugate was used to form cDNA by reverse transcription. The relative cDNA quantities were calculated from qPCR Ct values and used to assess the relative levels of cleavage. The graph illustrates the assay data obtained by using substrates for enterokinase and thrombin synthesized from individual oligonucleotides obtained from IDT Technologies (Coralville, Iowa).

Example 2: Composition of a Set of Custom Peptide Protease Substrates

One peptide construct set was designed and used in an assay system to analyze protease cleavage sites within a viral genome. For this purpose, a 2,600-plex peptide construct set was created based on the methods developed and constructs produced in Example 1, though as noted in Example 1, the peptide construct sets could have been created using a Scheme II embodiment as an alternative to Scheme I. The construct set was designed to test the substrate specificity of NS3 (hepacivirin) protease of hepatitis C virus.

The HCV viral genome is a single-stranded, 9.5 kb long RNA molecule that is translated into a single polyprotein of about 3,000 amino acids. The NS3 (hepacivirin) protease of HCV is responsible for the cleavage at the NS3/NS4A, NS4A/NS4B, NS4B/NS5A, and NS5A/NS5B sites of the polyprotein (Kwong, et al., Antiviral Res., 41(1):67-84 (1999)). It is essential for viral replication and the formation of infectious viral particles, and thus has been considered as one of the most attractive targets for anti-HCV therapy (see, e.g., Hahm, et al., J. Virol. 69(4):2534-9 (1995); Lahm, et al., Br J. Cancer. 65(3):341-6 (1992); Li, et al., Proc. Natl. Acad. Sci. USA., 102(49):17717-22 (2005)). Yet substrate specificity of the NS3 HCV protease is poorly studied. Only four peptide substrates have been reported and listed in the MEROPS protease database (Rawlings, et al, Nucleic Acids Res., 34 (Database issue):D270-2 (2006)): MEECSQHL (SEQ ID NO:8); TTPCSGSW (SEQ ID NO:9); VVCCSMSY(SEQ ID NO:10); and EVVTSTWV (SEQ ID NO:11), where P1-P1' positions are shown in bold (Blight, et al., Antivir Ther. 3(Suppl 3):71-81 (1998)). No substrate preferences have been reported thus far.

The model peptide construct set used to analyze potential substrates contained two groups of 8-mer peptide substrates. The first group consisted of 1,502 overlapping peptides derived from the sequence of the HCV single polyprotein with a step of two amino acids between peptides in the set. The second group (1,030 peptides) included variations of the four known substrates: SEQ ID NO:8, SEQ ID NO:9, SEQ ID NO:10 and SEQ ID NO:11 (Shiryaev, et al., J. Biol. Chem. 282(29):20847-53 (2007)). Positive and negative controls (68 peptides) were also tested to monitor the assay performance. Positive controls contained cleavage sites for the following commercially available proteases: thrombin, enterokinase, NS2B-NS3 proteases of Dengue and West Nile viruses, caspase-3, and furin. Negative controls included G10, A10, (GA)5, (AG)5 peptides, and no peptide.

The oligonucleotides encoding the peptides of interest were synthesized by conventional DNA synthesis (IDT Technologies, Coralville, Iowa) and/or using an Expedite 8909 DNA synthesizer using reagents from Glen Research (Sterling, Va.). This pool of oligonucleotides was successfully transcribed in vitro to yield a pool of corresponding RNAs. Characterization of the RNA pool via reverse transcription followed by sequencing showed a drop out rate of ~0.15% and an effect of G content on relative sequence abundance of ~1.5 fold at 20% incorporation.

Next, biotin-modified peptide constructs were generated using the methods described in Example 1. Peptide constructs were captured on streptavidin beads and the identifying oligonucleotides from the constructs captured on the beads were sequenced. DNA sequences observed, which corresponded to a peptide in the peptide construct set, indicated that the corresponding peptide construct was made. The frequency with which each DNA sequence occurred also provided an estimate of the abundance of each peptide construct in the pool.

The N-terminal biotinylated peptide constructs immobilized on magnetic beads were treated with NS3 HCV protease (AnaSpec, Fremont, Calif.), or with control proteases. Each treatment was carried out in a different reaction tube. A sample that was treated with a buffer was used as a negative control (i.e., a no protease control). Cleaved DNA molecules were collected from each sample and sequenced following the attachment of adaptor sequences by PCR.

Figure 9:
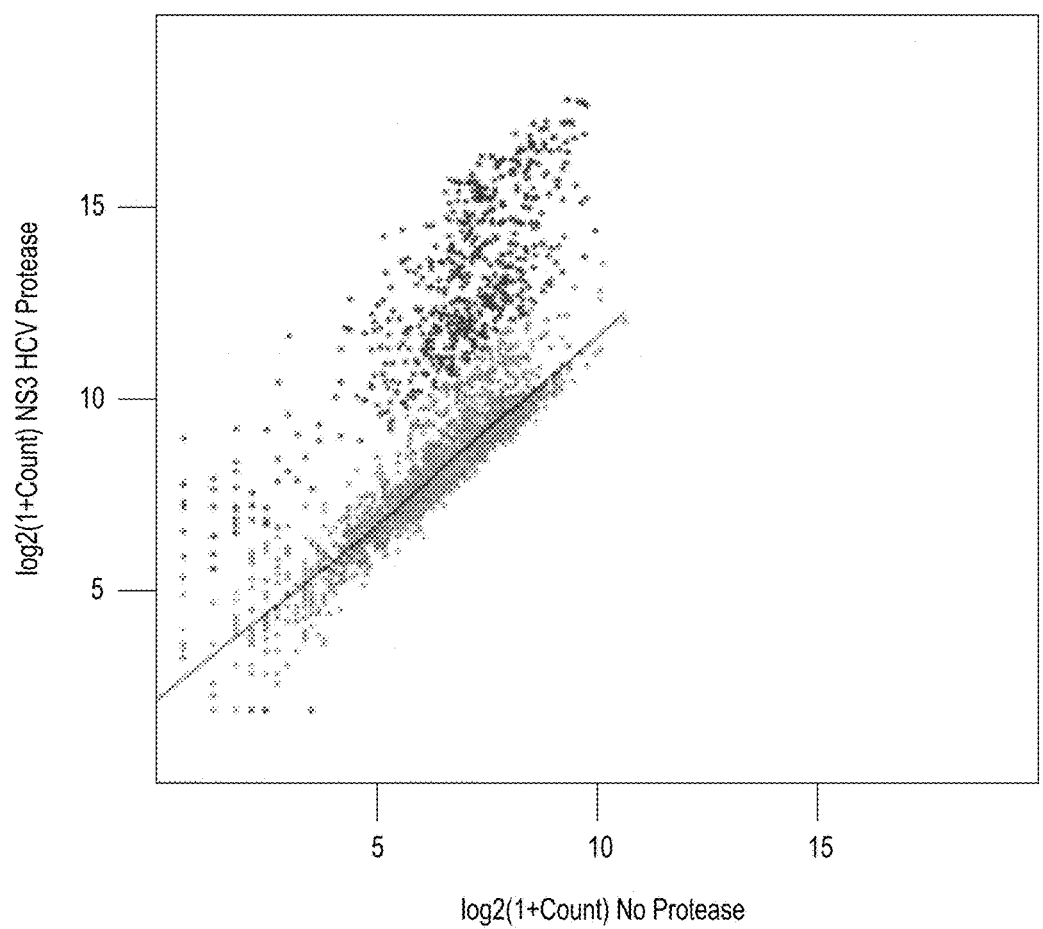
FIG. 9 illustrates a scatter plot of peptide abundances in NS3 HCV protease treated (Y-axis) and untreated constructs (X-axis).
Figure 10:
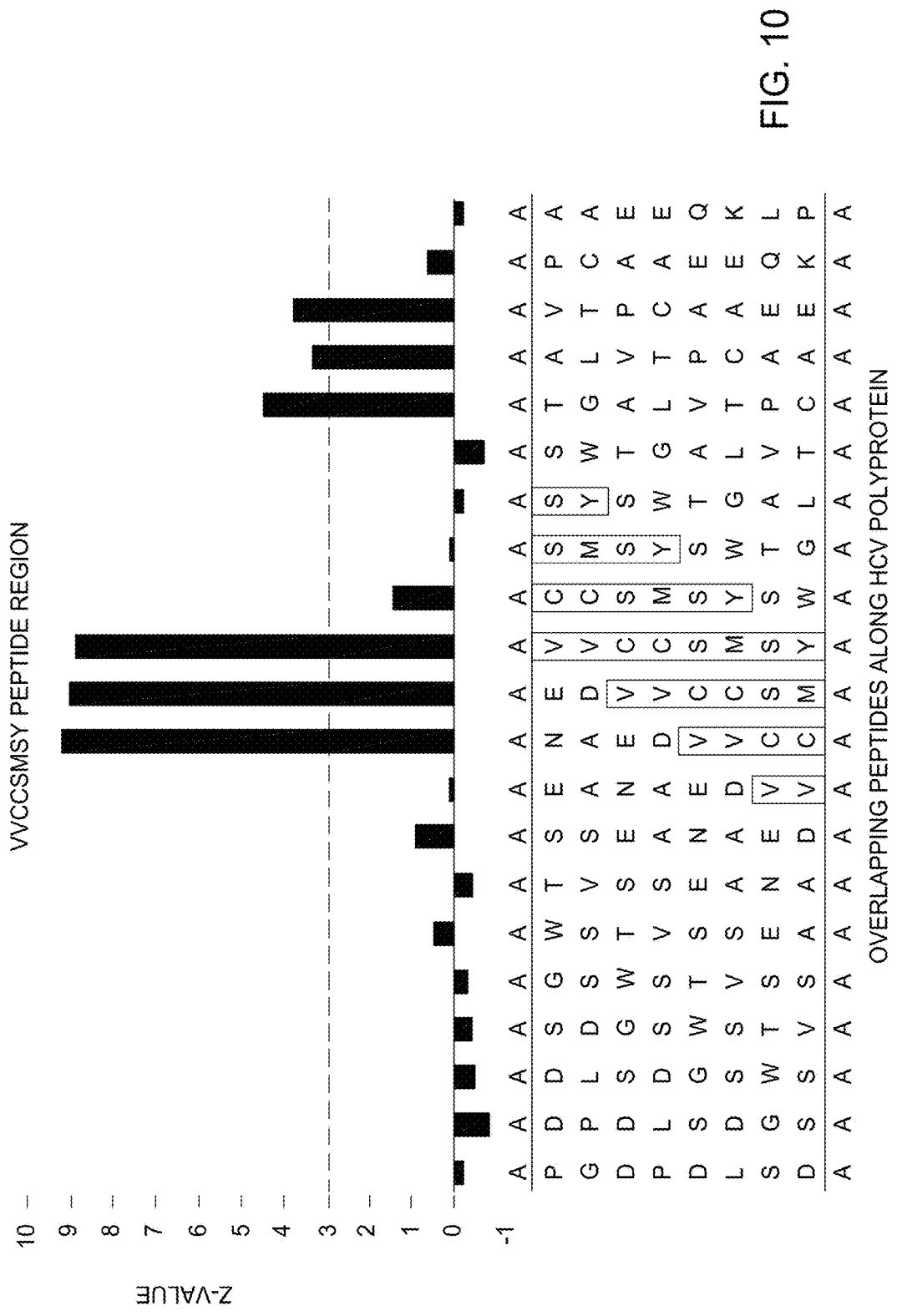
Figure 11:
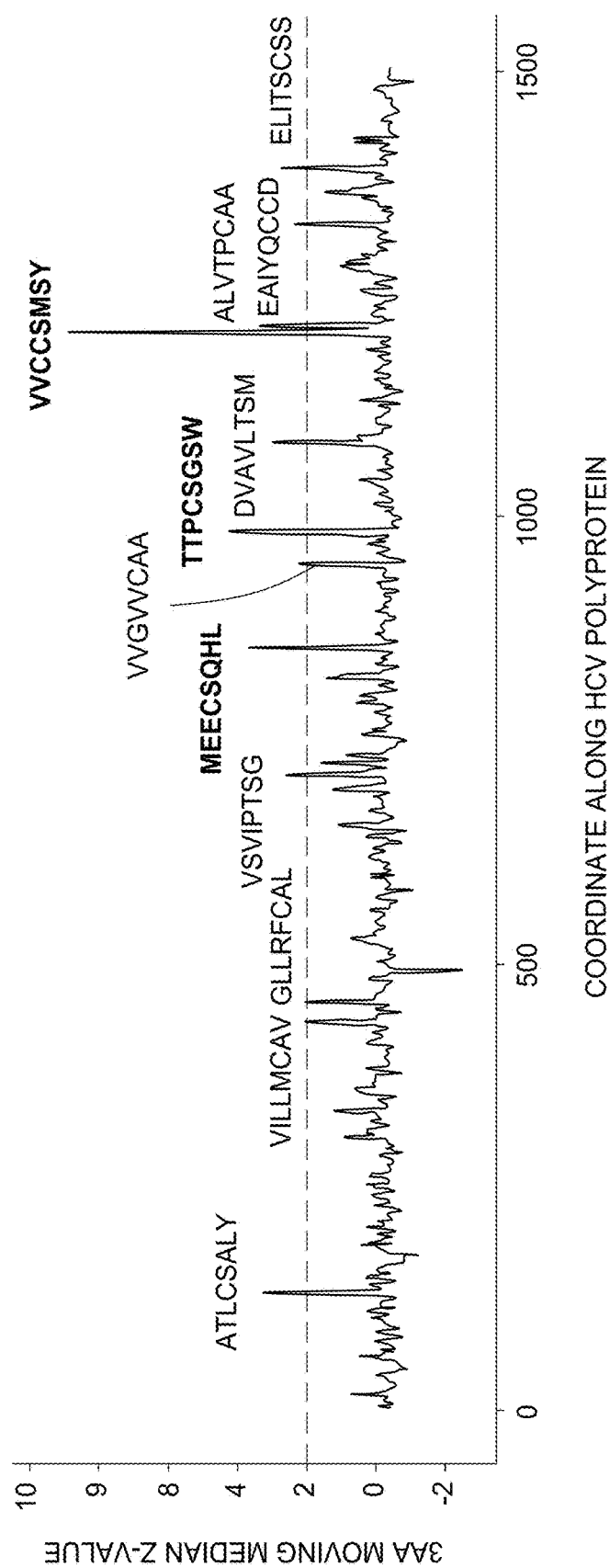
FIG. 11 illustrates a map of peptide cleavage sites identified by assaying overlapping 8-mer peptides of HCV polyprotein (SEQ ID NOS:22, 23, 24, 25, 8, 26, 9, 27, 10, 28, 12, and 29, in order of appearance from left to right).

FIGS. 9-11 illustrate the results obtained after treatment of the 2,600-plex peptide construct set with NS3 HCV protease. FIG. 9 illustrates a scatter plot of peptide abundances in HCV NS3 protease treated (Y-axis) and untreated control (X-axis). Peptide abundances were determined by counting the number of sequencing reads corresponding to each cDNA sequence coding for a given peptide. The dark points represent peptides that have a statistically significant change in abundance due to protease treatment. Statistical significance was calculated from analysis of distribution of residuals of loess fit. Z-values were assigned by estimating robust standard deviation of residuals (using median absolute deviation) and z=3 (p<0.0014) was chosen as a cutoff.

FIG. 10 illustrates relative amount of cleaved peptide determined from sequencing counts obtained for a set of 21 overlapping 8-mer peptides representing a part of HCV polyprotein around a known HCV NS3 protease cleavage site (VVCCSMSY (SEQ ID NO: 10)). The Y-axis represents the z-value for each peptide. The dotted line represents z-value=3. Because the peptide sequences overlap, two or more adjacent peptides may contain sufficient recognition sequence to be cleaved. Peptide sequences are written vertically. The known HCV NS3 protease recognition site is boxed. The letter "A" at the beginning and the end of each peptide's amino acid sequence represents alanine residues from the flanking common regions at the N- and C-termini. From left to right in FIG. 10, the 8-mer peptide sequences are SEQ ID NOs: 30-40, SEQ ID NO: 10, and SEQ ID NOs: 41-49.

FIG. 11 illustrates a map of peptide cleavage sites identified by assaying 1,502 overlapping 8-mer peptides covering the entire 3,011 amino acid sequence of HCV polyprotein. The data were filtered by requiring each set of 3 consecutive sequences to have a median z-score of ≥2. Bold peptide sequences represent three published HCV NS3 protease cleavage sites, while other peptide sequences represent new sites that were identified and fit the general requirements for the HCV NS3 protease cleavage. Peptide EAIYQCCD (SEQ ID NO: 12) represents a peptide substrate that does not fit the known HCV NS3 protease consensus. From left to right in FIG. 11, the 8-mer peptide sequences are SEQ ID NOs: 22-25, SEQ ID NO: 8, SEQ ID NO: 26, SEQ ID NO: 9, SEQ ID NO: 27, SEQ ID NO: 10, SEQ ID NO: 28, SEQ ID NO: 12, and SEQ ID NO: 29.

This assay provided a clear functional validation of the use of peptide constructs of the invention, as cleavage of 3 of the 4 known sites published in the MEROPS database was detected. Interestingly, the undetected site, EVVTSTWV (SEQ ID NO:11), is known to be cleaved only in cis, i.e, via an intramolecular cleavage event, and therefore would not be expected to be detected in the assay system. Therefore this assay system identified, in a single experiment, all known trans-cleavage sites of the NS3 HCV protease in the HCV polyprotein. In addition, several other new cleavage sites were identified and appear to fit the cleavage consensus sequence.

Thus, the approach using the peptide constructs of the invention allowed the efficient and cost-effective generation of a detailed proteolytic cleavage map of a large polyprotein representing a viral proteome. The approach also quantified the impact on protease cleavage efficiency of varying substrate sequence. For example, each position in the consensus sequence was varied by systematically substituting all 20 amino acids at each position. All the variants were present in the same peptide construct pool and therefore were assayed simultaneously. The ability to conduct the assay simultaneously on all substrates in the same pool, rather than in separate individual reactions, removes a significant source of experimental variability, and improves the ability to compare signals between peptides in the same experiment.

Example 3: Peptide Constructs Generated from Fragmented Genomic DNA

The constructs and assay systems of the invention were also used to perform proteomic analysis of the genome of an organism, the yeast Saccharomyces cerevisiae. Genomic DNA from *S. cerevisiae* was sheared using adaptive focused acoustics technology for DNA shearing (Covaris), and then size selected to obtain random DNA fragments of approximately 100 base pairs. Custom DNA adaptors were attached to create constructs such as those illustrated in FIG. 7 at 701.

A genomic DNA library was created with approximately 100 bp fragment size from *S. cerevisiae* genomic DNA, and it was determined by sequencing that the initial DNA pool covered ~93% of the genome. A set of peptide constructs was created from the genomic DNA library using the methods described in Example 1, although, again, a Scheme II "one-pot" embodiment may have been employed as well. Upon sequence analysis following production of the peptide constructs, the peptide construct set was determined to cover ~75% of the entire yeast genome. Because the fragmented library contains regions from both coding and non-coding regions of the genome, a significant portion of genomic fragments contained stop codons leading to reduced genome representation in the set of peptide constructs.

To analyze the performance of the whole yeast peptide construct set using the protease assay format described in Examples 1 and 2, the construct set was treated with thrombin protease. Sequence analysis demonstrated a significant enrichment of peptides containing thrombin cleavage sites, indicating that the peptide constructs as produced were functional and useful for further analysis of yeast peptides of interest.

Example 4: Model System for Kinase Substrate Generation and Screening

A model system was created to test the ability of the methods and assay systems of the present invention to produce and utilize kinase substrate constructs, and to detect phosphorylation events. The model peptides used were GEAIYAAPFA (SEQ ID NO:13), a target of commercially available ABL1 tyrosine kinase (New England Biolabs, Ipswich, Mass.) and AGYIYGSFKG (SEQ ID NO:14), a target of commercially available SRC tyrosine kinase (Millipore, Billerica, Mass.). The kinase phosphorylation sites are shown in bold in the peptide sequences.

In addition to the peptide sequence of interest, a peptide tag was introduced into each construct at the N-terminus to be used in the kinase substrate screening assay for peptide construct capture.

Figure 12:
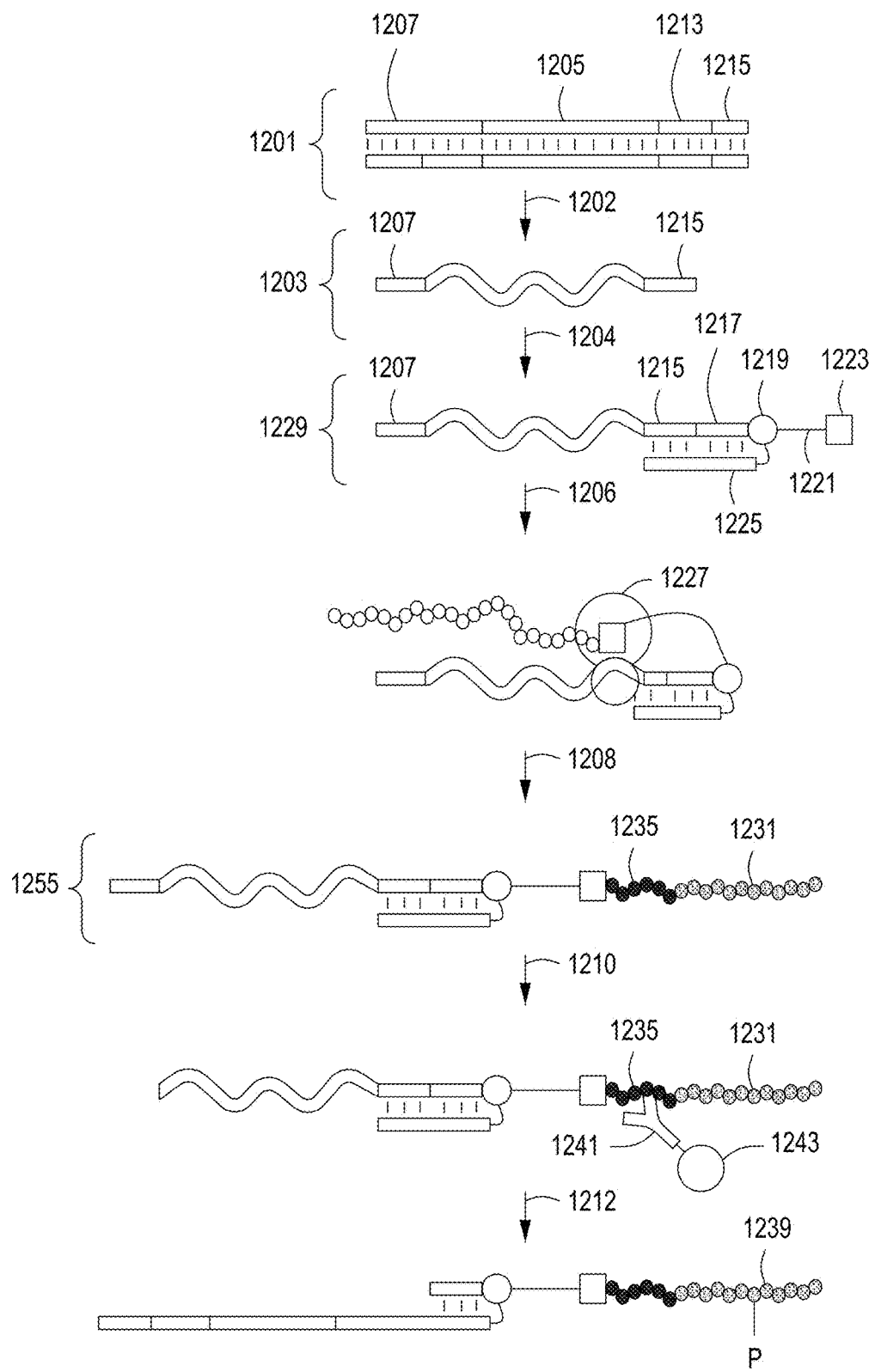
FIG. 12 illustrates a specific example of the production of peptide constructs of the invention as described in detail in Example 4.

The production of the peptide constructs for the kinase assay is illustrated in FIG. 12. A model peptide construct comprising a peptide substrate for Abl kinase (GEAIYAAPFA (SEQ ID NO:13)) and a cDNA identifying nucleotide was prepared individually. Briefly, a DNA template 1201 comprising DNA encoding the model peptide was synthesized by conventional DNA synthesis (IDT Technologies, Coralville, Iowa). The DNA template 1201 contained a region 1205 coding for the custom peptide sequence (peptide substrate for Abl kinase (GEAIYAAPFA (SEQ ID NO:13)) and the regions that are typically shared in multiplex experiments, e.g., coding for the T7 promoter 1207, a ribosomal binding site 1209 (as described in He, et al., supra, and Tao, et al., supra), a C-terminal peptide tag 1213, and a region 1215 used for ligation of a DNA adaptor. The oligonucleotide template 1201 was used to synthesize the corresponding RNA 1203 through in vitro transcription 1202. Efficient in vitro transcription from a double-stranded DNA template was performed using AmpliScribe T7-Flash (Epicentre Biotechnologies, Madison, Wis.), and the resulting RNA product was isolated by gel electrophoresis and purification using commercial kits (Qiagen, Valencia, Calif.).

An adaptor was attached to the 3'-end of the RNA via a template-directed ligation process 1204 (Kurz, et al., supra). The adaptor consisted of the two DNAs 1217 and 1225 cross-linked via a psoralen residue 1219, a long polyethylene glycol linker 1221, and a 3'-puromycin residue 1223, as described above for the protease assay system (see FIG. 7). The circle in the picture represents a crosslinked psoralen residue 1219, and the square represents a 3'-puromycin residue 1223.

This intermediate construct was subjected to in vitro translation 1206. The ribosome 1227 stalls when it reaches the DNA fragment at the 3'-end of an RNA template, allowing the puromycin residue to enter the A-site of the ribosome and get incorporated into the C-terminus of the peptide. The process 1208 resulted in formation of a peptide construct 1255. The peptide construct 1255 comprised a custom peptide region 1231 and a peptide tag 1235 (for example a FLAG (DYKDDDK) tag (SEQ ID NO:3) or a GNASASA tag (SEQ ID NO:6)), at the C-terminus to be used for purification or analysis of constructs with fully translated peptides, as well as the mRNA used to translate the peptide. Using a representative sample of the product from 1208, peptide constructs were captured by their C-terminal tag (1235 in FIGS. 12 and 13A) with magnetic beads (1305 in FIG. 13A) containing immobilized anti-FLAG antibodies (1304 in FIG. 13A). PAGE analysis of the constructs eluted from the beads confirmed that constructs comprising full-length peptides were formed in high abundance relative to truncated constructs (data not shown).

Following translation, the RNA portion of the construct was replaced by cDNA-using reverse transcription followed by RNAse H induced RNA degradation (Kurz et al., supra). Next, the peptide construct was purified by capture on DNA-affinity beads with an immobilized oligonucleotide complementary to the ribosome binding site present in the cDNA. This ensures that any peptides that were translated in step 1206 but not bound to puromycin in step 1208 will be excluded from the pool. The captured constructs were eluted from the beads and used in a kinase substrate screening assay resulting in the phosphylation of a subset of the peptide constructs (1210).

Figure 13:
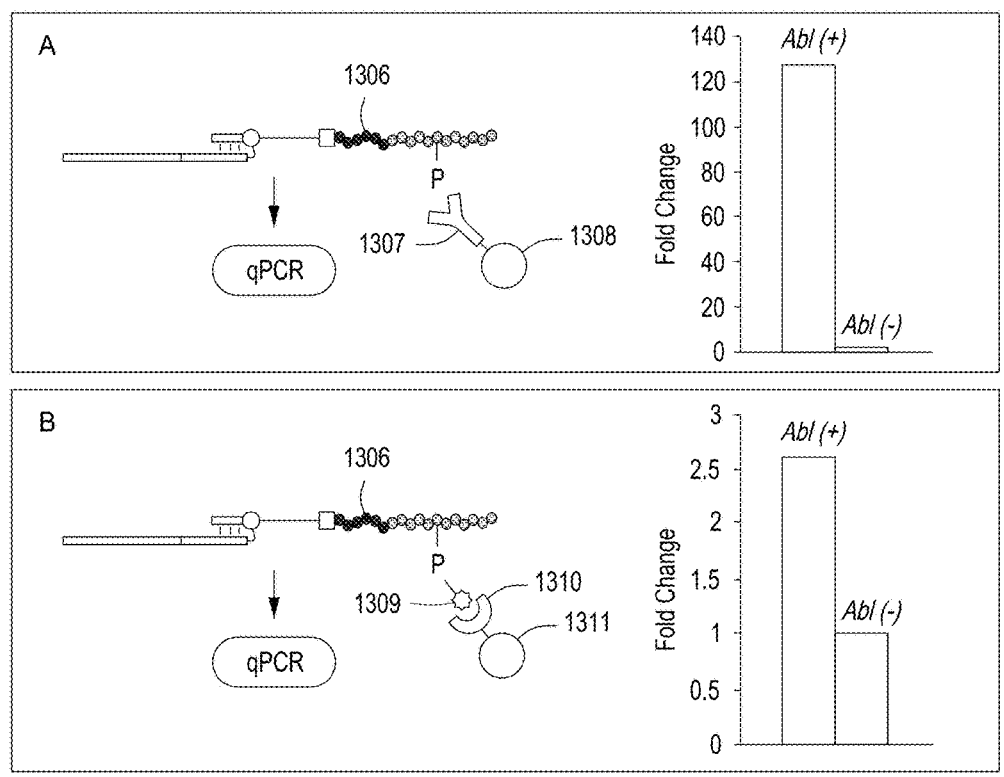
FIG. 13A illustrates an alternative exemplary embodiment of capture of a peptide fusion construct and results obtained in a kinase assay.
FIG. 13B illustrates yet another exemplary embodiment of capture of a peptide fusion construct and results obtained in a kinase assay.

Results illustrating the kinase substrate screening process using an individual substrate are shown in FIG. 13. In FIG. 13A, the left panel is a representative illustration showing direct capture of phosphorylated peptide constructs (1306) using anti-phosphonotyrosine antibodies (1307) immobilized on magnetic beads (1308). In the right panel FIG. 13B, results of the kinase assay (Abl kinase) using peptide constructs containing the Abl substrate (GEAIYAAPFA (SEQ ID NO:13)) are shown. The peptide constructs containing phosphorylated peptides were eluted from the beads using a solution of phenyl phosphate and quantitated by qPCR. The Y-axis of the bar plot shows the relative qPCR signal $\{2^{[Ct(untreated)-Ct(test)]}\}$, where Ct(test) is the Ct value obtained for the kinase-treated or untreated preparation. The qPCR signal was significantly higher (~120-fold) for the kinase-treated preparation, relative to the untreated preparation.

The left panel of FIG. 13B is a representative illustration showing indirect capture of phosphorylated peptide constructs (1306) using a method similar to the one described in Shults, et al., supra. Peptides containing phosphorylated tyrosine residues (1306) were labeled with a biotin residue (1309) and captured with streptavidin (1310) immobilized on magnetic beads (1311). The right panel of FIG. 13B shows the results of the Abl kinase assay. The assay was performed as described in herein supra except for a variation in the capture method. The peptide constructs containing phosphorylated peptides was eluted from the beads in water by heating at 95° C. for 5 minutes and quantitated by qPCR. The Y-axis at the bar plot shows the relative qPCR signal $\{2^{[Ct(untreated)-Ct(test)]}\}$, where Ct(test) is the Ct value obtained for the kinase-treated or untreated preparation. The qPCR signal was ~2-fold higher for the kinase-treated preparation, relative to the untreated preparation.

A 3,243-plex set of 10-mer peptide constructs was designed and synthesized in the same manner as the single Abl substrate construct described, supra. A recently published study (Shults et al., supra) describes the use of a 900-plex set of individually synthesized peptides with content derived from several sources: known kinase phosphorylation consensus sequences, randomized sequences based on peptide library data or consensus sequences, and phosphorylation site databases. The authors reported finding one or more specific kinase substrates from the peptide set for 17 out of 26 kinases tested. This set was used as a starting point for the design of the 3,243-plex model set. All well-performing peptides from the 900-plex set were included and additional peptide targets were incorporated based on more recent literature data (see, e.g., Amanchy, et al., J. Proteome Res., 7:3900-10 (2008); Jalal, et al., Science Signaling, 2:54 (2009); and Bohmer, et al., British Journal of Haematology, 144:127-30 (2009)) as well as the most current data from phosphoroproteomics databases (Hornbeck, et al., Proteomics, 4:1551-1561 (2004); Olsen et al., Cell, 127:635-648 (2006); and Yang, et al., Bioinformatics, 24:114-120 (2008)).

The length of all peptides was adjusted to 10-mers with the addition of extra glycine (G) or alanine (A) residues at the termini. The entire sequences of three phosphoproteins were also added (Cortactin, FLT3, and Src proteins; 550, 993, and 536 amino acids, respectively) all of which contain several known phosphorylation sites (Hornbeck, et al., Proteomics, 4:1551-61 (2004)). Each phosphoprotein was represented by overlapping peptides with a step of two amino acids (266, 489, and 260 peptides). Mutation sets for the consensus sequence for Abl (GEAIYAAPFA (SEQ ID NO:13)) and for FLT3 (NEYFYQNFDE (SEQ ID NO:15) (Hornbeck, et al., supra) were also included in the set (each position in these consensus sequences was changed to all remaining 19 natural amino acids while the rest of the sequence remained constant). The series of controls used were based on three tyrosine substrates and three serine substrates, in which each reactive group (D, E, K, Y, S,) was individually mutated for evaluation of the specificity of the phosphate modifying EDC chemistry (Shults, et al., supra).

The following tyrosine kinases have been used for experiments with the 3,243-plex peptide construct set: Src (p60), Abl, Lck, Flt3, Kit, Jak2. Results are described below for Src and Abl kinases, and preliminary analysis reveals distinct patterns of phosphorylation for the additional four tyrosine kinases Lck, Flt3, Kit, and Jak2. To enrich for peptide constructs that had been phosphorylated, the kinase-treated and untreated peptide constructs were exposed to beads comprising anti-phosphotyrosine antibody. Unbound peptide constructs were washed away, and captured phosphorylated constructs were eluted with phenyl phosphate. Phosphorylated peptide constructs were collected from each sample, and the identifying oligonucleotides were amplified and sequenced. These experiments demonstrated the ability to generate large peptide sets, identify kinase phosphorylation sites and study kinase substrate specificity using the methods of the present invention.

Figure 14:
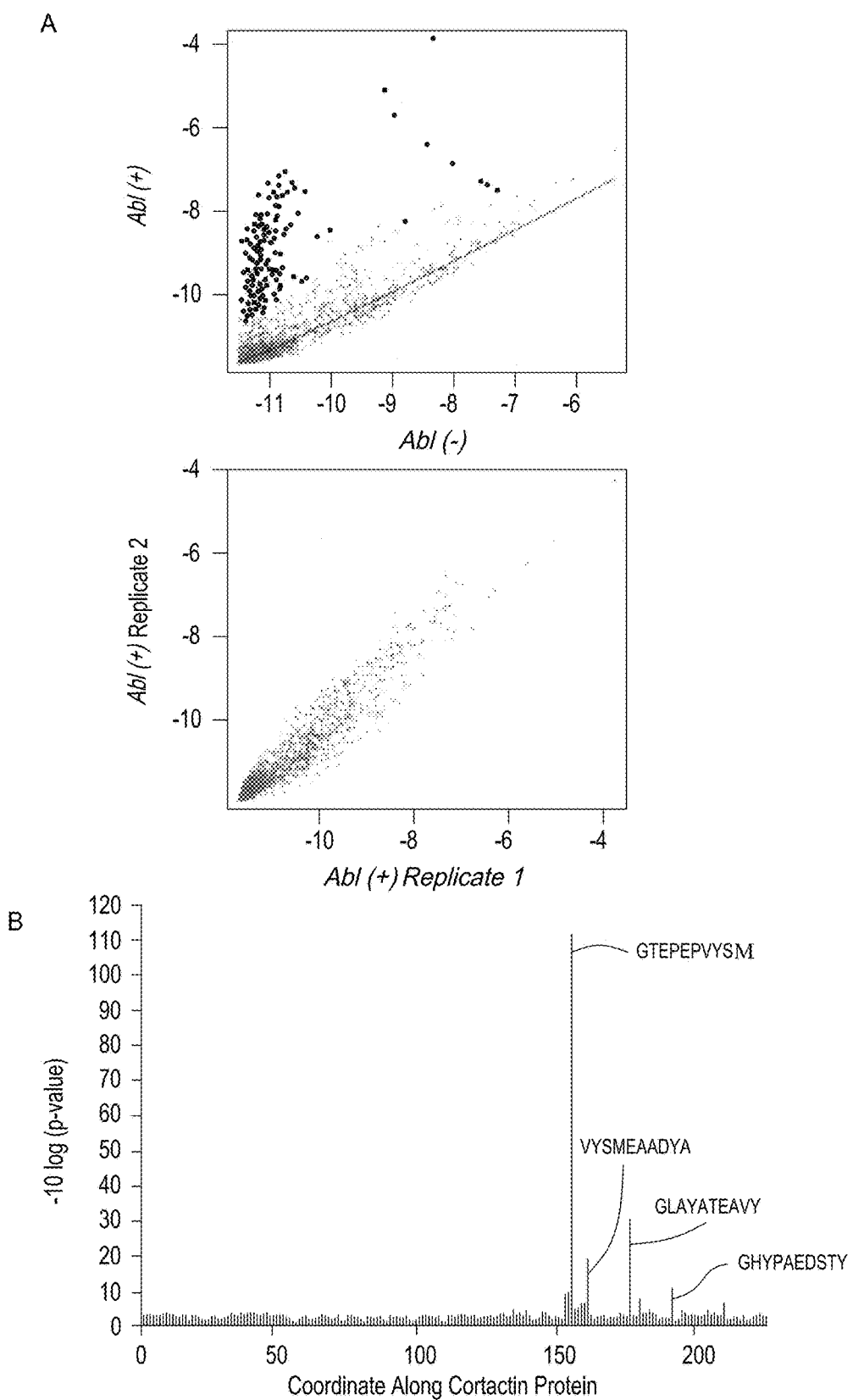
FIG. 14A shows two scatter plots showing results obtained using the methods of the invention.
FIG. 14B shows results from a kinase assay after treatment of peptides derived from cortactin protein sequence with Src kinase.
Figure 15:
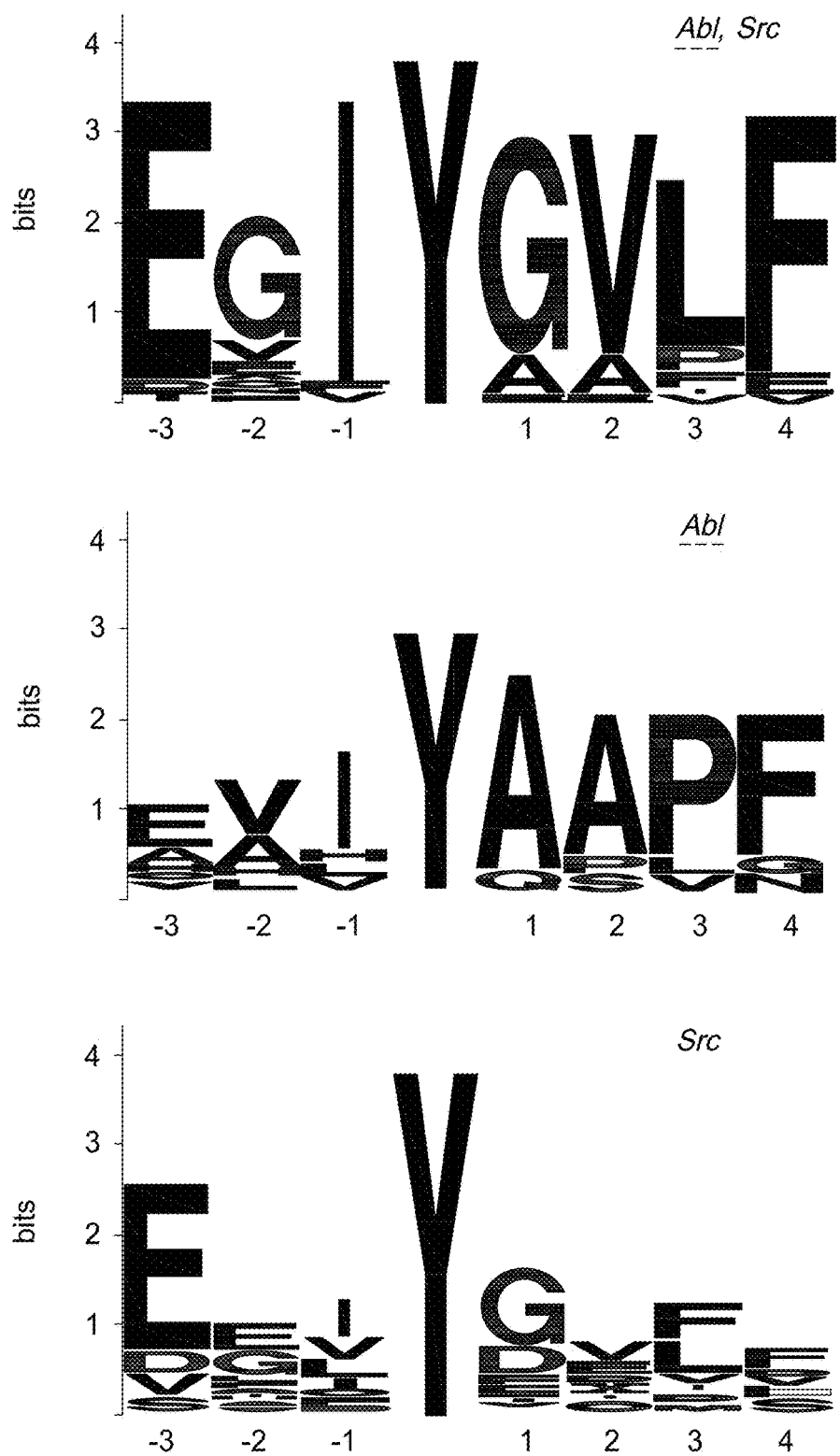
FIG. 15 shows consensus sequences for Abl and Src kinases derived from analysis of kinase assay data.

Representative examples of the assay results for Abl and Src kinases are shown in FIGS. 14 and 15. The pool included 1,557 peptides that contain no tyrosine residues, serving as a large pool of negative controls in the experiments that measure only phosphorylation by tyrosine kinases. None of the 1557 negative peptides were detected in the assays, indicating a very low false positive rate FIG. 14A shows results obtained after treatment of the peptide construct set with Abl kinase. The upper panel is a scatter plot of peptide construct abundances in Abl kinase-treated (Y-axis) and untreated controls (X-axis). The relative peptide construct abundances were determined by comparing sequencing counts of cDNAs corresponding to these peptide constructs. The bold points represent peptides that have a statistically-significant change in abundance due to kinase treatment. Statistical significance was calculated from analysis of loess fit residuals in four independent replicate experiments. The p-values were assigned by modeling residuals as independent normal variables. To adjust for multiple hypotheses testing, false discovery rate (FDR) was computed using the Benjamini and Hochberg procedure (Benjamini and Hochberg, J. of the Royal Statistical Society, Series B (Methodological), 57:289-300 (1995)). The cutoff was chosen at FDR<0.1 which corresponds to nominal p-value <0.005. The lower panel is a comparison of two experimental replicates of the pool treated with Abl kinase (R=0.97). Additionally, comparison of two negative control samples resulted in R=0.98 (not shown).

FIG. 14B shows results obtained after treatment of the peptide construct set with Src kinase. The Y-axis represents −10 Log(p-value) for individual peptides along the Cortactin protein (X-axis). The data shown is a subset of the pool consisting of 268 overlapping peptide sequences derived from the sequence of the protein cortactin (550 amino acids) with a step of two amino acids (119 peptides contained tyrosine residues). Cortactin, a central regulator of actin cytoskeleton dynamics (Lua and Low, B. C. FEBS Lett, 579:577-585 (2005)), is a well-studied phosphoprotein containing multiple phosphorylation sites, three of which are sites known to be recognized by the Src p60 kinase and are described in the PhosphoSite database (Hornbeck, et al., supra). Two of the three Src phosphorylation sites (GLAYATEAVY (SEQ ID NO: 16) and GHYPAEDSTY (SEQ ID NO: 17)) were detected, both of which have been identified by in vitro and in vivo studies (Huang, et al., J. Biol Chem, 273:25770-76 (1998) and Lua and Low, supra). Two more sites were identified (GTEPEPVYSM (SEQ ID NO: 18) and VYSMEAADYR (SEQ ID NO: 19)), which are not known phosphorylation sites of Src. However, several in vivo global studies using mass spec analysis have identified one of these phosphorylation sites (GTEPEPVYSM (SEQ ID NO: 18)) in vivo (Jørgensen, et al., Science, 326:1502-09 (2009) and Heibeck, et al. J Proteome Res, 8:3852-61 (2009)) and this phosphorylated tyrosine is a key regulatory point of cortactin in response to stress (Stuible, et al., J Biol Chem, 283:15740-46 (2008)). Therefore, the screen identified two of the three known Src phosphorylation sites and also found two additional phosphorylation sites, one of which provides the first in vitro evidence of the kinase responsible for modifying this residue in Cortactin. It is possible that the third known site that was not detected (QVSSAYQKTV (SEQ ID NO: 20)) needs additional amino acids beyond the 10-mer peptide format (see, e.g., Kennelly and Krebs, J Biol Chem, 266:15555-58 (1991)) or an additional in vivo co-factor for the Src kinase that was not present in the in vitro assay system.

FIG. 15 shows the analysis of consensus sequences for Abl and Src kinases. The methods of the present invention were used to quickly and systematically assess the importance of every amino acid at each position for substrate specificity. The top consensus panel is based on peptide sequences that were identified as substrates for both Abl and Src kinases. The middle consensus panel is based on peptide sequences that were identified as substrates for Abl only, and the bottom consensus panel is based on peptide sequences that were identified as substrates for Src only. In the top panel, a motif for both Abl and Src kinases was identified that is consistent with published data and known in vivo substrates (Songyang, et al., Nature, 373:536-39 (1995) and Rychlewski, et al., J Mol Biol, 336:307-11 (2004)) by varying every position of an Abl substrate (GEAIYAAPFA (SEQ ID NO:13)). For example, a strong requirement for isoleucine at the −1 position was observed, with valine or leucine also tolerated at this position. The bottom two panels reveal the Src p60 kinase phosphorylates substrates highly similar to Abl, yet distinct differences in substrate preferences were seen. Src p60 has a strong preference for acidic residues at −2 and −3 positions, while Abl tolerates more residues at these sites (V, A, H, L). Furthermore, at sites +1 and +2, Abl prefers substrates with AA while Src p60 phosphorylates motifs with a G present at the +1 site (compare Abl and Src only panels). These data correlate well with published in vitro measurements of phosphorylation rates, showing Abl preferentially phosphorylates YAA while Src prefers YG (Songyang, supra and Tinker, et al., Anticancer Res., 12:123-27 (1992)).

The results demonstrate that the peptide constructs may be used to detect phosphorylation events. If a more complex pool of peptides is used, the kinase treated and untreated preparations may be sequenced e.g., using a next-generation DNA sequencing instrument to determine which peptide sequences are enriched in the kinase treated population.

Example 5: Antibody Profiling

The methods and peptide construct sets of the invention can be used in binding assays, for example antibody profiling. Custom peptide construct sets are designed that represent epitopes derived from pathogen sequences, and these custom peptide construct sets are used to screen serum samples for antibodies that bind specifically, thus identifying exposure to said pathogens. Similarly, methods of the invention are applicable to the detection and analysis of autoimmune diseases. There is a large range of such diseases, each characterized by the set of autoantigens targeted by the antibodies present. Identifying the targeted antigens therefore can be used as a diagnostic tool to identify the nature of the disease. The ability to define not only the protein antigens, but the specific peptide epitopes targeted further enables the differentiation of subgroups of patients with varying prognoses.

The methods of the invention provide much higher resolution analysis than current assays, such as antigen-based ELISA assays and peptide microarrays. While peptide arrays are well established as a tool for antibody profiling, current arrays are limited to relatively small numbers of peptides and therefore can only query a few antigens at a time. No technology currently exists that can map peptide epitopes at high resolution across a large number of antigens in parallel. In contrast, the methods of the present invention are capable of producing large defined sets of peptide constructs, making it possible to query a significant fraction of the human proteome in a single experiment.

The methods of the invention also make it possible to study the population dynamics of the antibody complement present in patients, which is likely to yield important new insights into autoimmune disease. There is significant and immediate medical need for a technology with these capabilities.

As an example, the following set of 16 proteins, covering 4,683 amino acids, is represented by a set of ~2,260 peptide constructs with peptide sequences that are tiled across all the protein sequences in steps of 2 amino acids: Rheumatoid Factor (Fc region of human IgG) (~129aa)—Rheumatoid Arthritis; SS-A (Ro protein) (538aa)—Sjögren's Syndrome, Lupus; SS-B (La protein) (408aa)—Sjögren's Syndrome, Lupus; Scl-70 (DNA Topoisomerase I) (765aa)—Systemic Scleroderma; Jo-1 (Histidyl tRNA synthetase) (509aa)—Polymyositis, Dermatomyositis; U1 snRNP (U1 snRNP proteins 70 kDa, A, C) (437, 282, 159aa)—Mixed Connective Tissue Diseases, Lupus, Sjögren's Syndrome, Scleroderma, Polymyositis; Sm/Smith Antigen (snRNP proteins B/B', D1, D2, D3, E, F, G) (240, 119, 118, 126, 92, 86, 76aa)—Lupus; CenpB (80 kDa centromere protein B) (599aa)—Systemic Sclerosis.

In a first general assay format, antibodies from a patient sample are immobilized on a support, e.g., by capturing IgG antibodies from serum using an anti-IgG column. Next, the immobilized antibodies are exposed to the peptide construct set. This is typically be done using appropriate blocking and washing procedures well known in the art that are used to improve specificity. Bound peptides constructs are eluted, and sequencing is used to identify peptides that were captured.

In a second general assay format, the peptide constructs are attached to a solid support, e.g., via biotin (as has been used previously, e.g., in the protease assay supra) or via a cleavable linker. The peptide constructs are then exposed to the sample (for example, serum or some fraction of serum containing antibodies). This typically is done using appropriate blocking and washing procedures well known in the art that are used to improve specificity. In a preferred embodiment, the antibody-peptide construct complexes are then separated from the surface by cleavage of the cleavable linker. The released complexes are then captured on a second solid support via the antibody (e.g., on an anti-IgG column). This is used to separate unbound from bound peptide conjugates. The bound conjugates are then released and their cognate nucleic acids are sequenced.

Alternatively, the first capture step can be repeated to increase specificity, i.e., the antibodies are re-captured on a second set of peptide constructs. In this embodiment, after the first step the antibodies alone are released while the constructs remain attached to the surface. Preferably, this is done in a way that differentially releases specifically bound antibodies, for example, by using relatively gentle elution methods that leave a large fraction of non-specifically bound antibodies attached to the surface. The first capture step is then repeated and after this second capture the antibody-peptide conjugate complexes are separated from the surface by cleavage of the cleavable linker. The released complexes are then captured in a third capture step on a solid support via the antibody (e.g., on an anti-IgG column). This is used to separate unbound from bound peptide conjugates. The bound conjugates are then released and their cognate nucleic acids are sequenced.

In each method, reference or control samples may be processed in parallel to assist in differentiating specific from non-specific binding. Because immunoassays are well established as a technology, there are many variations on how such an assay can be implemented that will be apparent to one skilled in the art, including variations in the type and order of specific steps and introducing methods for increasing sensitivity and specificity by reducing the amount of non-specific binding (e.g., by using different types of proteins, including antibodies, as blockers).

Example 6: Production of a Single Peptide Construct by a "One-Pot" Reaction

A Scheme II "one-pot" reaction was used to generate a single species of peptide construct suitable for use in a protease assay as described in Example 2. This reaction may be parallelized in tubes or microtiter plates for small- to medium-sized sets of template oligonucleotides with one nucleic acid template species per reaction vessel, i.e., tube or well. Large sets of oligonucleotide templates are enabled by using a microfluidic partitioning strategy in conjunction with an oligonucleotide array as described infra.

A double-stranded DNA template 401 was developed by primer extension of two oligonucleotides synthesized by conventional methods. The resulting dsDNA was amplified by PCR and purified by MinElute PCR purification kit (QIAGEN), and adjusted to 500 nM.

A CoA-modified adaptor 409 was produced from a 5'-phosphorylated short hairpin oligonucleotide that contained an amino modified nucleotide in the loop and a 9 nucleotide 3'-overhang with a complementary sequence to the 3'-end of RNA template to be transcribed from the dsDNA template. The hairpin oligonucleotide was modified with NHS-PEG8-Maleimide (Thermo Scientific) and Coenzyme A (Calbiochem). After gel-purification, the CoA-modified oligonucleotide was adjusted to 100 µM.

The peptide construct was formed by incubation at 37° C. for 2 hours in 10 µL of reaction mixture with 1× PURExpress solution (NEB), 50 nM dsDNA template, 10 µM CoA-modified oligonucleotide, 8 units of Murine RNase inhibitor (NEB), 200 units of T4 DNA ligase (NEB) and 1 µM Sfp (NEB). After construct formation, the mRNA portion of the peptide construct was reverse transcribed to cDNA using M-MuLV reverse transcriptase (NEB). The mRNA portion was digested with RNase H (Invitrogen), RNase A and RNase T1 (Amgen).

The resulting peptide constructs comprising the translated peptide, corresponding cDNA, and intervening adaptor were captured on silica beads derivatized with oligonucleotides binding to the RBS region of the cDNA. The peptide portion of each construct comprised a test peptide, in this case a substrate for the protease thrombin, as well as an N-terminal tag region (substrate for the protease TEV) used for further modification of the construct. The N-terminal tag was cleaved with TEV to expose an N-terminus glycine residue. which was then biotinylated using Biotin-PEG12-NHS ester (Thermo Scientific). The biotinylated peptide constructs were eluted from beads by heating at 95° C. in water. This method produced a single species of biotinylated peptide construct, suitable for performing the protease assays described supra; however, it can be extended to a set of many peptide constructs by employing a reaction partitioning strategy as discussed in the next Example.

Example 7: Generating a Pool of Peptide Constructs Using Parallel "One-Pot" Reactions The Scheme II "one-pot" reaction described herein may be used in conjunction with a microfluidic reaction-partitioning strategy and an oligonucleotide template array to generate a large set of peptide-cDNA constructs suitable for performing a highly multiplexed protease assay.

Figure 16:
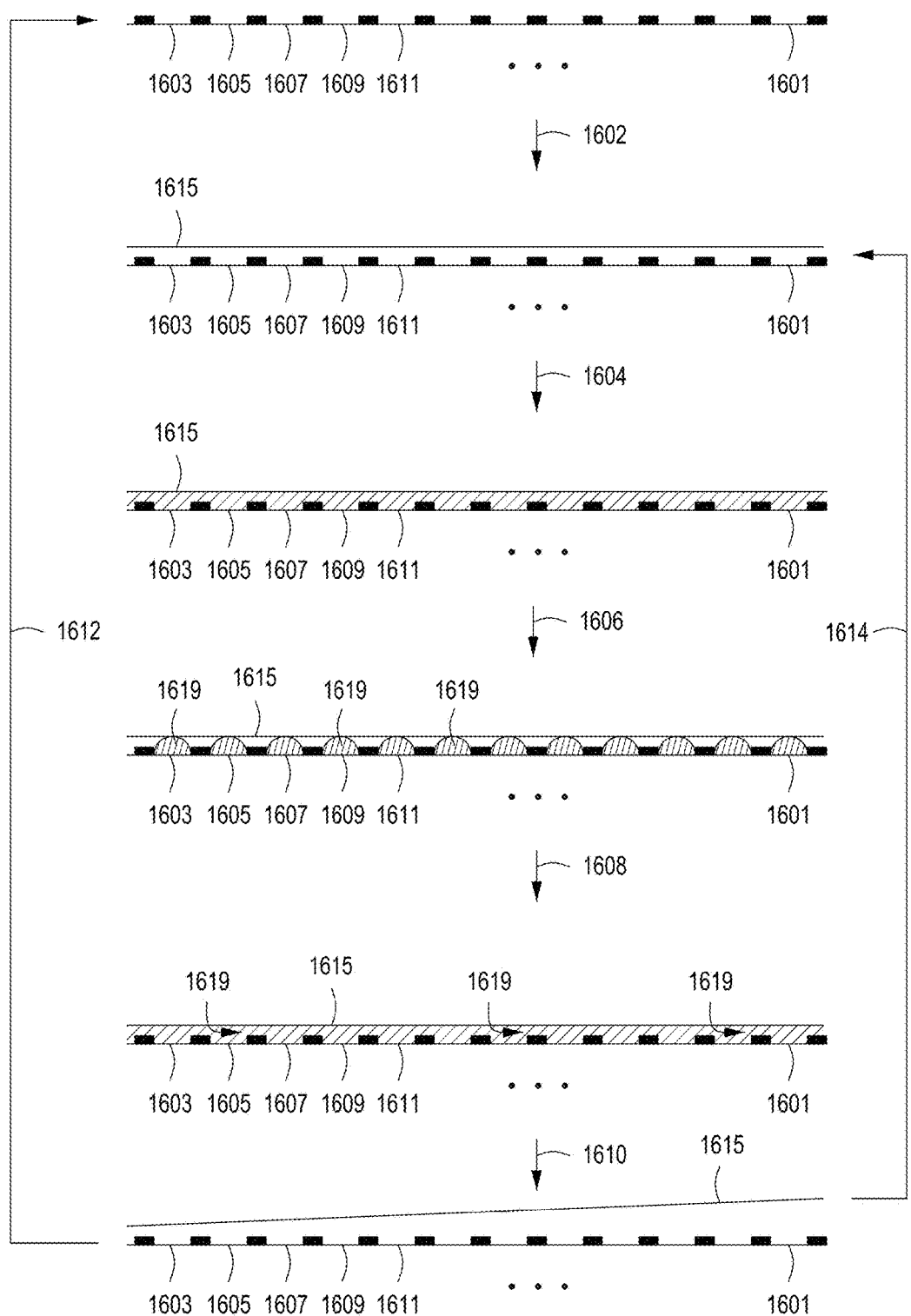
FIG. 16 presents a simplified representation of one embodiment for performing many 'one pot' peptide construct synthesis in parallel.

A microfluidic partitioning array is fabricated according to the methods of U.S. Ser. No. 13/283,906, filed Oct. 28, 2011, incorporated herein in its entirety. This array, in preferred embodiments, is designed with a pattern of features having the same spatial layout as the features on a commercially available custom-content oligonucleotide array. FIG. 16 is a simplified graphic illustrating one method of performing "one-pot" peptide construct synthesis in parallel. An oligonucleotide array 1601 is shown having features 1603, 1605, 1607, 1609 and so on, where each feature typically comprises oligonucleotides coding for a single species of peptide, where typically the oligonucleotides in different features will code for different peptides. At step 1602, a partitioning array 1615 and the oligonucleotide array 1601 are brought into registration using a modifier photolithographic mask aligner and clamped together with a well defined gap between the two array surfaces to form a sealed flow-cell (details not shown). The flow cell is filled at step 1604 with reaction mix 1617, as described in Example 5 and in conjunction with FIG. 4, comprising a cell-free translation and transcription mix (PURExpress, NEB), T4 Ligase, SFP synthase, as well as an adaptor containing the coenzyme A capture moiety.

At step 1606, a portion of the liquid is withdrawn forming isolated reaction volumes at the location of each feature on the oligonucleotide array. Other methods of reaction partitioning could be applied here to the same effect, that is, producing an array of reaction partitions where each partition encompasses one or more features on the oligonucleotide array. The assembly comprising both the oligonucleotide array 1601 and the partitioning array 1615 and the clamping apparatus is incubated at 37° C. for 2 hours. Within each reaction partition, the "one-pot" reaction, comprising transcription, translation, adaptor ligation, and peptide construct formation 1619 occurs. These component reactions may occur simultaneously or sequentially depending on the kinetics of each as has been discussed supra. Because, in preferred embodiments, each reaction volume encompasses the contents of a single feature on the oligonucleotide array—nominally a single species of DNA—transcription nominally produces a single species of messenger RNA, translation of which yields a single species of peptide. A single species of peptide fusion construct is then produced comprising the single peptide species and the RNA that encodes its sequence. At the end of the incubation time period, the flow cell is flushed at step 1608 with a buffer solution containing EDTA or another reagent to quench further enzymatic reactions and the contents of each reaction volume are combined into a single pool. Further purification and modification is possible using RBS bead capture or any of the other methods described supra. After flushing the peptide constructs and reaction mix from the oligonucleotide array/partitioning array assembly at step 1610, the assembly may be reused to synthesize more of the peptide constructs (step 1612).

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims. In the claims that follow, unless the term "means" is used, none of the features or elements recited therein should be construed as means-plus-function limitations pursuant to 35 U.S.C. § 112, ¶6.

The invention claimed is:

1. A method of identifying a substrate of an enzyme, comprising:
   (a) contacting a set of peptide constructs with an enzyme, wherein each peptide construct of the set comprises a peptide portion and an identifying nucleic acid portion that identifies the peptide portion, wherein the identifying nucleic acid portion of each peptide construct comprises a polynucleotide sequence or complement thereof encoding the peptide portion of the peptide construct, and wherein the peptide portion of at least one of the peptide constructs is acted upon by the enzyme;
   (b) separating the at least one peptide construct comprising the peptide portion that is acted upon by the enzyme from peptide constructs comprising peptide portions that are not acted upon by the enzyme;
   (c) enriching the at least one peptide construct comprising the peptide portion that is acted upon by the enzyme; and
   (d) sequencing all or a portion of the identifying nucleic acid portion of the at least one peptide construct enriched in step (c) comprising the peptide portion that is acted upon by the enzyme, thereby identifying the peptide portion that is acted upon by the enzyme as a substrate for the enzyme.

2. The method of claim 1, wherein the enzyme is a kinase and wherein the peptide portion of the at least one peptide construct is phosphorylated by the kinase.

3. The method of claim 2, wherein the kinase comprises a plurality of kinases.

4. The method of claim 2, wherein the enriching step is carried out by capturing the peptide portion that is phosphorylated by the kinase.

5. The method of claim 4, wherein the capturing is carried out by using an immobilized capture agent for the phosphorylated peptide portion.

6. The method of claim 5, wherein the capture agent comprises a phospho-specific antibody.

7. The method of claim 2, further comprising a step of labeling the peptide portion that is phosphorylated by the kinase with an affinity tag, wherein the affinity tag is capable of being captured by an immobilized capture agent specific for the affinity tag.

8. The method of claim 7, wherein the labeling step is catalyzed by the kinase.

9. The method of claim 2, wherein each peptide construct of the set further comprises an affinity tag capable of being captured by a capture agent specific for the affinity tag.

10. The method of claim 2, wherein in step (b) a single peptide construct comprising a peptide portion that is phosphorylated by the kinase is separated from peptide constructs comprising peptide portions that are not phosphorylated by the kinase.

11. The method of claim 2, wherein in step (b) a plurality of peptide constructs comprising peptide portions that are phosphorylated by the kinase are separated from peptide constructs comprising peptide portions that are not phosphorylated by the kinase.

12. The method of claim 2, further comprising a step of analyzing all or a portion of the identifying nucleic acid portions of the peptide constructs separated in step (b) comprising peptide portions that are not phosphorylated by the kinase, thereby identifying the peptide portions that are not phosphorylated by the kinase.

13. The method of claim 2, wherein the sequencing of step (d) comprises performing digital sequencing, nucleic acid sequencing, or any combination thereof.

14. The method of claim 1, wherein the enzyme is a protease and wherein the peptide portion of the at least one peptide construct is cleaved by the protease.

15. A method of assaying kinase activity in a sample, comprising:

(a) contacting a sample with a set of peptide constructs, wherein each peptide construct of the set comprises a peptide portion and an identifying nucleic acid portion that identifies the peptide portion, wherein the identifying nucleic acid portion of each peptide construct comprises a polynucleotide sequence or complement thereof encoding the peptide portion of the peptide construct, and wherein the peptide portion of at least one of the peptide constructs is phosphorylated by a kinase in the sample;

(b) separating the at least one peptide construct comprising the peptide portion that is phosphorylated by the kinase from peptide constructs comprising peptide portions that are not phosphorylated by the kinase;

(c) enriching the at least one peptide construct comprising the peptide portion that is phosphorylated by the kinase; and (d) sequencing all or a portion of the identifying nucleic acid portion of the peptide construct enriched in step (c) comprising the peptide portion that is phosphorylated by the kinase, thereby identifying the peptide portion that is phosphorylated by the kinase, wherein phosphorylation of the identified peptide portion by the kinase indicates activity of the kinase in the sample.

16. The method of claim 15, wherein the kinase comprises a plurality of kinases.

17. The method of claim 15, wherein each peptide construct of the set further comprises an affinity tag capable of being captured by a capture agent specific for the affinity tag.

18. The method of claim 15, further comprising a step of analyzing all or a portion of the identifying nucleic acid portions of the peptide constructs separated in step (b) comprising peptide portions that are not phosphorylated by the kinase, thereby identifying the peptide portions that are not phosphorylated by the kinase.

19. The method of claim 15, wherein the sequencing of step (d) comprises performing digital sequencing, nucleic acid sequencing, or any combination thereof.

20. The method of claim 15, wherein the peptide portion of at least one of the peptide constructs is not phosphorylated by the kinase and is used as a control.

21. The method of claim 15, wherein:
the kinase is a first kinase;
in step (a), the peptide portion of the at least one peptide construct is a substrate for the first kinase, and the set further comprises at least one peptide construct of which the peptide portion is phosphorylated by a second kinase;

step (b) further comprises separating the at least one peptide construct comprising the peptide portion that is phosphorylated by the second kinase from peptide constructs comprising peptide portions that are not phosphorylated by the second kinase;

step (c) further comprises enriching the at least one peptide construct comprising the peptide portion that is phosphorylated by the second kinase; and step (d) further comprises sequencing all or a portion of the identifying nucleic acid portion of the peptide construct enriched in step (c) comprising the peptide portion that is phosphorylated by the second kinase, thereby identifying the peptide portion that is phosphorylated by the second kinase, wherein phosphorylation of the identified peptide portion by the second kinase indicates activity of the second kinase in the sample.

22. The method claim 21, further comprising comparing the peptide portion that is phosphorylated by the first kinase in the sample and the peptide portion that is phosphorylated by the second kinase in the sample.

23. The method of claim 15, wherein:
the sample is a first sample;
step (a) further comprises contacting a second sample with the set of peptide constructs, wherein the peptide portion of at least one of the peptide constructs is phosphorylated by a kinase in the second sample;

step (b) further comprises separating the at least one peptide construct comprising the peptide portion that is phosphorylated by the kinase in the second sample from peptide constructs comprising peptide portions that are not phosphorylated by the kinase in the second sample;

step (c) further comprises enriching the at least one peptide construct comprising the peptide portion that is phosphorylated by the kinase in the second sample; and step (d) further comprises sequencing all or a portion of the identifying nucleic acid portion of the peptide construct enriched in step (c) comprising the peptide portion that is phosphorylated by the kinase in the second sample, thereby identifying the peptide portion that is phosphorylated by the kinase in the second sample, wherein phosphorylation of the identified peptide portion by the kinase indicates activity of the kinase in the second sample.

24. The method claim 23, further comprising comparing the peptide portion that is phosphorylated by the kinase in the first sample and the peptide portion that is phosphorylated by the kinase in the second sample.

* * * * *

SEQUENCE LISTING

```
<160> NUMBER OF SEQ ID NOS: 49

<210> SEQ ID NO 1
<211> LENGTH: 9
<212> TYPE: PRT
<213> ORGANISM: Artificial Sequence
<220> FEATURE:
<223> OTHER INFORMATION: Peptide tag

<400> SEQUENCE: 1

Gly Leu Val Pro Arg Gly Ser Ala Gly
1               5

<210> SEQ ID NO 2
<211> LENGTH: 9
<212> TYPE: PRT
<213> ORGANISM: Artificial Sequence
<220> FEATURE:
<223> OTHER INFORMATION: Peptide tag

<400> SEQUENCE: 2

Ala Gly Asp Asp Asp Asp Lys Ala Gly
1               5

<210> SEQ ID NO 3
<211> LENGTH: 8
<212> TYPE: PRT
<213> ORGANISM: Artificial Sequence
<220> FEATURE:
<223> OTHER INFORMATION: Peptide tag

<400> SEQUENCE: 3

Asp Tyr Lys Asp Asp Asp Asp Lys
1               5

<210> SEQ ID NO 4
<211> LENGTH: 6
<212> TYPE: PRT
<213> ORGANISM: Artificial Sequence
<220> FEATURE:
<223> OTHER INFORMATION: Peptide tag

<400> SEQUENCE: 4

Asp Thr Tyr Arg Tyr Ile
```

```
1               5

<210> SEQ ID NO 5
<211> LENGTH: 8
<212> TYPE: PRT
<213> ORGANISM: Artificial Sequence
<220> FEATURE:
<223> OTHER INFORMATION: Peptide tag

<400> SEQUENCE: 5

Ala Gly Asn Ala Ser Ala Ser Ala
1               5

<210> SEQ ID NO 6
<211> LENGTH: 7
<212> TYPE: PRT
<213> ORGANISM: Artificial Sequence
<220> FEATURE:
<223> OTHER INFORMATION: Peptide tag

<400> SEQUENCE: 6

Gly Asn Ala Ser Ala Ser Ala
1               5

<210> SEQ ID NO 7
<211> LENGTH: 8
<212> TYPE: PRT
<213> ORGANISM: Artificial Sequence
<220> FEATURE:
<223> OTHER INFORMATION: Peptide tag

<400> SEQUENCE: 7

Glu Asn Leu Tyr Phe Gln Cys Ala
1               5

<210> SEQ ID NO 8
<211> LENGTH: 8
<212> TYPE: PRT
<213> ORGANISM: Artificial Sequence
<220> FEATURE:
<223> OTHER INFORMATION: Peptide tag

<400> SEQUENCE: 8

Met Glu Glu Cys Ser Gln His Leu
1               5

<210> SEQ ID NO 9
<211> LENGTH: 8
<212> TYPE: PRT
<213> ORGANISM: Artificial Sequence
<220> FEATURE:
<223> OTHER INFORMATION: Peptide tag

<400> SEQUENCE: 9

Thr Thr Pro Cys Ser Gly Ser Trp
1               5

<210> SEQ ID NO 10
<211> LENGTH: 8
<212> TYPE: PRT
<213> ORGANISM: Artificial Sequence
<220> FEATURE:
<223> OTHER INFORMATION: Peptide tag

<400> SEQUENCE: 10

Val Val Cys Cys Ser Met Ser Tyr
1               5
```

<210> SEQ ID NO 11
<211> LENGTH: 8
<212> TYPE: PRT
<213> ORGANISM: Artificial Sequence
<220> FEATURE:
<223> OTHER INFORMATION: Peptide tag

<400> SEQUENCE: 11

Glu Val Val Thr Ser Thr Trp Val
1               5

<210> SEQ ID NO 12
<211> LENGTH: 8
<212> TYPE: PRT
<213> ORGANISM: Artificial Sequence
<220> FEATURE:
<223> OTHER INFORMATION: Peptide tag

<400> SEQUENCE: 12

Glu Ala Ile Tyr Gln Cys Cys Asp
1               5

<210> SEQ ID NO 13
<211> LENGTH: 10
<212> TYPE: PRT
<213> ORGANISM: Artificial Sequence
<220> FEATURE:
<223> OTHER INFORMATION: Peptide tag

<400> SEQUENCE: 13

Gly Glu Ala Ile Tyr Ala Ala Pro Phe Ala
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Peptide tag

<400> SEQUENCE: 14

Ala Gly Tyr Ile Tyr Gly Ser Phe Lys Gly
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Peptide tag

<400> SEQUENCE: 15

Asn Glu Tyr Phe Tyr Gln Asn Phe Asp Glu
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Peptide tag

<400> SEQUENCE: 16

Gly Leu Ala Tyr Ala Thr Glu Ala Val Tyr
1               5                   10

```
<210> SEQ ID NO 17
<211> LENGTH: 10
<212> TYPE: PRT
<213> ORGANISM: Artificial Sequence
<220> FEATURE:
<223> OTHER INFORMATION: Peptide tag

<400> SEQUENCE: 17

Gly His Tyr Pro Ala Glu Asp Ser Thr Tyr
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Peptide tag

<400> SEQUENCE: 18

Gly Thr Glu Pro Glu Pro Val Tyr Ser Met
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Peptide tag

<400> SEQUENCE: 19

Val Tyr Ser Met Glu Ala Ala Asp Tyr Arg
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Peptide tag

<400> SEQUENCE: 20

Gln Val Ser Ser Ala Tyr Gln Lys Thr Val
1               5                   10

<210> SEQ ID NO 21
<211> LENGTH: 6
<212> TYPE: PRT
<213> ORGANISM: Artificial Sequence
<220> FEATURE:
<223> OTHER INFORMATION: Peptide tag

<400> SEQUENCE: 21

Glu Asn Leu Tyr Phe Gln
1               5

<210> SEQ ID NO 22
<211> LENGTH: 8
<212> TYPE: PRT
<213> ORGANISM: Artificial Sequence
<220> FEATURE:
<223> OTHER INFORMATION: Peptide tag

<400> SEQUENCE: 22

Ala Thr Leu Cys Ser Ala Leu Tyr
1               5
```

```
<210> SEQ ID NO 23
<211> LENGTH: 8
<212> TYPE: PRT
<213> ORGANISM: Artificial Sequence
<220> FEATURE:
<223> OTHER INFORMATION: Peptide tag

<400> SEQUENCE: 23

Val Ile Leu Leu Met Cys Ala Val
1               5

<210> SEQ ID NO 24
<211> LENGTH: 8
<212> TYPE: PRT
<213> ORGANISM: Artificial Sequence
<220> FEATURE:
<223> OTHER INFORMATION: Peptide tag

<400> SEQUENCE: 24

Gly Leu Leu Arg Phe Cys Ala Leu
1               5

<210> SEQ ID NO 25
<211> LENGTH: 8
<212> TYPE: PRT
<213> ORGANISM: Artificial Sequence
<220> FEATURE:
<223> OTHER INFORMATION: Peptide tag

<400> SEQUENCE: 25

Val Ser Val Ile Pro Thr Ser Gly
1               5

<210> SEQ ID NO 26
<211> LENGTH: 8
<212> TYPE: PRT
<213> ORGANISM: Artificial Sequence
<220> FEATURE:
<223> OTHER INFORMATION: Peptide tag

<400> SEQUENCE: 26

Val Val Gly Val Val Cys Ala Ala
1               5

<210> SEQ ID NO 27
<211> LENGTH: 8
<212> TYPE: PRT
<213> ORGANISM: Artificial Sequence
<220> FEATURE:
<223> OTHER INFORMATION: Peptide tag

<400> SEQUENCE: 27

Asp Val Ala Val Leu Thr Ser Met
1               5

<210> SEQ ID NO 28
<211> LENGTH: 8
<212> TYPE: PRT
<213> ORGANISM: Artificial Sequence
<220> FEATURE:
<223> OTHER INFORMATION: Peptide tag

<400> SEQUENCE: 28

Ala Leu Val Thr Pro Cys Ala Ala
1               5

<210> SEQ ID NO 29
```

```
<211> LENGTH: 8
<212> TYPE: PRT
<213> ORGANISM: Artificial Sequence
<220> FEATURE:
<223> OTHER INFORMATION: Peptide tag

<400> SEQUENCE: 29

Glu Leu Ile Thr Ser Cys Ser Ser
1               5

<210> SEQ ID NO 30
<211> LENGTH: 8
<212> TYPE: PRT
<213> ORGANISM: Artificial Sequence
<220> FEATURE:
<223> OTHER INFORMATION: Peptide tag

<400> SEQUENCE: 30

Pro Gly Asp Pro Asp Leu Ser Asp
1               5

<210> SEQ ID NO 31
<211> LENGTH: 8
<212> TYPE: PRT
<213> ORGANISM: Artificial Sequence
<220> FEATURE:
<223> OTHER INFORMATION: Peptide tag

<400> SEQUENCE: 31

Asp Pro Asp Leu Ser Asp Gly Ser
1               5

<210> SEQ ID NO 32
<211> LENGTH: 8
<212> TYPE: PRT
<213> ORGANISM: Artificial Sequence
<220> FEATURE:
<223> OTHER INFORMATION: Peptide tag

<400> SEQUENCE: 32

Asp Leu Ser Asp Gly Ser Trp Ser
1               5

<210> SEQ ID NO 33
<211> LENGTH: 8
<212> TYPE: PRT
<213> ORGANISM: Artificial Sequence
<220> FEATURE:
<223> OTHER INFORMATION: Peptide tag

<400> SEQUENCE: 33

Ser Asp Gly Ser Trp Ser Thr Val
1               5

<210> SEQ ID NO 34
<211> LENGTH: 8
<212> TYPE: PRT
<213> ORGANISM: Artificial Sequence
<220> FEATURE:
<223> OTHER INFORMATION: Peptide tag

<400> SEQUENCE: 34

Gly Ser Trp Ser Thr Val Ser Ser
1               5

<210> SEQ ID NO 35
<211> LENGTH: 8
```

<212> TYPE: PRT
<213> ORGANISM: Artificial Sequence
<220> FEATURE:
<223> OTHER INFORMATION: Peptide tag

<400> SEQUENCE: 35

Trp Ser Thr Val Ser Ser Glu Ala
1               5

<210> SEQ ID NO 36
<211> LENGTH: 8
<212> TYPE: PRT
<213> ORGANISM: Artificial Sequence
<220> FEATURE:
<223> OTHER INFORMATION: Peptide tag

<400> SEQUENCE: 36

Thr Val Ser Ser Glu Ala Asn Ala
1               5

<210> SEQ ID NO 37
<211> LENGTH: 8
<212> TYPE: PRT
<213> ORGANISM: Artificial Sequence
<220> FEATURE:
<223> OTHER INFORMATION: Peptide tag

<400> SEQUENCE: 37

Ser Ser Glu Ala Asn Ala Glu Asp
1               5

<210> SEQ ID NO 38
<211> LENGTH: 8
<212> TYPE: PRT
<213> ORGANISM: Artificial Sequence
<220> FEATURE:
<223> OTHER INFORMATION: Peptide tag

<400> SEQUENCE: 38

Glu Ala Asn Ala Glu Asp Val Val
1               5

<210> SEQ ID NO 39
<211> LENGTH: 8
<212> TYPE: PRT
<213> ORGANISM: Artificial Sequence
<220> FEATURE:
<223> OTHER INFORMATION: Peptide tag

<400> SEQUENCE: 39

Asn Ala Glu Asp Val Val Cys Cys
1               5

<210> SEQ ID NO 40
<211> LENGTH: 8
<212> TYPE: PRT
<213> ORGANISM: Artificial Sequence
<220> FEATURE:
<223> OTHER INFORMATION: Peptide tag

<400> SEQUENCE: 40

Glu Asp Val Val Cys Cys Ser Met
1               5

<210> SEQ ID NO 41
<211> LENGTH: 8
<212> TYPE: PRT

```
<213> ORGANISM: Artificial Sequence
<220> FEATURE:
<223> OTHER INFORMATION: Peptide tag

<400> SEQUENCE: 41

Cys Cys Ser Met Ser Tyr Ser Trp
1               5

<210> SEQ ID NO 42
<211> LENGTH: 8
<212> TYPE: PRT
<213> ORGANISM: Artificial Sequence
<220> FEATURE:
<223> OTHER INFORMATION: Peptide tag

<400> SEQUENCE: 42

Ser Met Ser Tyr Ser Trp Thr Gly
1               5

<210> SEQ ID NO 43
<211> LENGTH: 8
<212> TYPE: PRT
<213> ORGANISM: Artificial Sequence
<220> FEATURE:
<223> OTHER INFORMATION: Peptide tag

<400> SEQUENCE: 43

Ser Tyr Ser Trp Thr Gly Ala Leu
1               5

<210> SEQ ID NO 44
<211> LENGTH: 8
<212> TYPE: PRT
<213> ORGANISM: Artificial Sequence
<220> FEATURE:
<223> OTHER INFORMATION: Peptide tag

<400> SEQUENCE: 44

Ser Trp Thr Gly Ala Leu Val Thr
1               5

<210> SEQ ID NO 45
<211> LENGTH: 8
<212> TYPE: PRT
<213> ORGANISM: Artificial Sequence
<220> FEATURE:
<223> OTHER INFORMATION: Peptide tag

<400> SEQUENCE: 45

Thr Gly Ala Leu Val Thr Pro Cys
1               5

<210> SEQ ID NO 46
<211> LENGTH: 8
<212> TYPE: PRT
<213> ORGANISM: Artificial Sequence
<220> FEATURE:
<223> OTHER INFORMATION: Peptide tag

<400> SEQUENCE: 46

Ala Leu Val Thr Pro Cys Ala Ala
1               5

<210> SEQ ID NO 47
<211> LENGTH: 8
<212> TYPE: PRT
<213> ORGANISM: Artificial Sequence
```

```
<220> FEATURE:
<223> OTHER INFORMATION: Peptide tag

<400> SEQUENCE: 47

Val Thr Pro Cys Ala Ala Glu Glu
1               5

<210> SEQ ID NO 48
<211> LENGTH: 8
<212> TYPE: PRT
<213> ORGANISM: Artificial Sequence
<220> FEATURE:
<223> OTHER INFORMATION: Peptide tag

<400> SEQUENCE: 48

Pro Cys Ala Ala Glu Glu Gln Lys
1               5

<210> SEQ ID NO 49
<211> LENGTH: 8
<212> TYPE: PRT
<213> ORGANISM: Artificial Sequence
<220> FEATURE:
<223> OTHER INFORMATION: Peptide tag

<400> SEQUENCE: 49

Ala Ala Glu Glu Gln Lys Leu Pro
1               5
```